United States Patent [19]
Ohyama et al.

[11] Patent Number: 5,747,448
[45] Date of Patent: May 5, 1998

[54] DERIVATIVES OF CYCLODEPSIPEPTIDE PF 1022

[75] Inventors: Makoto Ohyama; Maki Ohishi; Yumiko Okada, all of Odawara; Masao Koyama, Yokohama; Shinjiro Sumi; Yasushi Murai, both of Odawara; Masayuki Takagi; Tadaaki Okada, both of Yokohama; Osamu Sakanaka, Odawara; Toshio Yoneta, Odawara; Katsuharu Iinuma, Odawara; Seiji Shibahara, Yokohama, all of Japan

[73] Assignee: Meiji Seika Kaisha, Ltd., Tokyo, Japan

[21] Appl. No.: 505,213

[22] PCT Filed: Feb. 18, 1994

[86] PCT No.: PCT/JP94/00252

§ 371 Date: Sep. 8, 1995

§ 102(e) Date: Sep. 8, 1995

[87] PCT Pub. No.: WO94/19334

PCT Pub. Date: Sep. 1, 1994

[30] Foreign Application Priority Data

Feb. 19, 1993 [JP] Japan ................... 5-029498
Feb. 19, 1993 [JP] Japan ................... 5-029505

[51] Int. Cl.$^6$ .................. A61K 38/15; C07K 11/02
[52] U.S. Cl. ............... 514/11; 514/9; 530/317; 530/323; 530/328
[58] Field of Search ................ 530/317, 323, 530/328; 514/9, 11

[56] References Cited

U.S. PATENT DOCUMENTS 5,116,815  5/1992  Takagi et al. ................... 514/11
5,514,773  5/1996  Nishiyama et al. ............. 530/317

OTHER PUBLICATIONS

Kanaoka et al. 'Bassianolide, A New Insecticidal Cyclodepsipeptide From Beauveria Bassiana and Verticillium Lecanii', Agric. Biol. Chem. 42(3) pp. 629–635, 1978.

Isogai et al. 'Bassianilide: Syntheses of its Analogs and NMR Studies', Peptide Chemistry (ed. N. Izumiya), Protein Research Foundation, pp. 167–170, 1979.

Ivanov et al. 'Syntheic and Natural Cyclodepsipeptides', in Peptides pp. 337–350, 1965.

*Primary Examiner*—Douglas W. Robinson
*Assistant Examiner*—Anish Gupta
*Attorney, Agent, or Firm*—Larson & Taylor

[57] ABSTRACT

Novel PF 1022 derivatives—cyclodepsipeptides represented by the below-described formula (I)—and acid addition salts thereof, which have been synthesized according to the present invention, have anthelmintic activities against various parasitic worms which are parasitic on human bodies, domestic animals and pet animals. They are therefore useful as anthelmintics for the prevention or treatment of parasitic infections.

Formula (I):

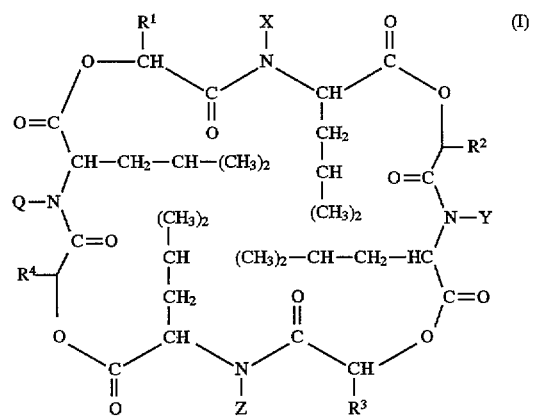

wherein $R^1$, $R^2$, $R^3$, $R^4$, Q, X, Y and Z have been defined herein.

12 Claims, No Drawings

DERIVATIVES OF CYCLODEPSIPEPTIDE PF 1022

TECHNICAL FIELD

The present invention relates to novel derivatives having a cyclo-tetradepsipeptide skeletal structure in common to PF 1022, which is a cyclodepsipeptide and has anthelmintic activities, and having excellent anthelmintic activities; and also to anthelmintic agent containing the derivatives. The novel PF 1022 derivatives according to the present invention show excellent anthelmintic activities against worms parasitic on animals and therefore are useful as anthelmintic agent.

BACKGROUND ART

The PF 1022 substance is a cyclodepsipeptide which was found as a result of a study on anthelmintic compounds against fowl roundworms [see Japanese Patent Application Laid-Open (Kokai) No. HEI 3-35796, European Patent Application Publication No. 0382173A2 and "J. Antibiotics", 45, 692(1992)]. In addition, the PF 1022 substance is a fermentation product, which is produced by the culture of a filamentous fungus PF1022 strain (deposited under FERM BP-2671 with National Institute of Bioscience and Human-Technology Agency in Tsukuba-shi under the provisions of the Budapest Treaty) belonging to Agonomycetales and is a cyclodepsipeptide represented by the following formula (A):

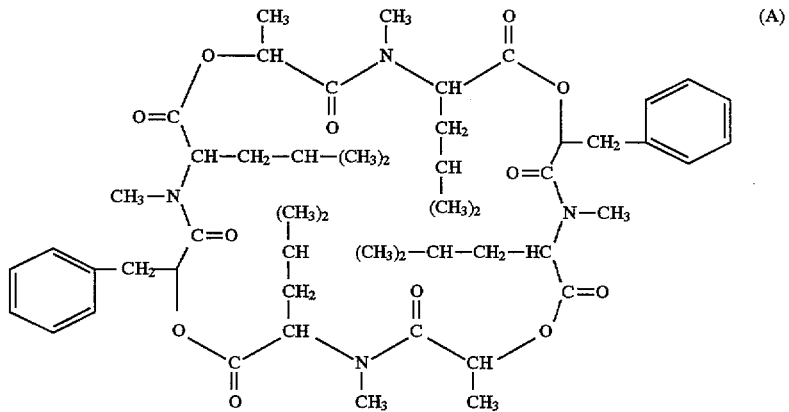

(A)

The PF 1022 substance is a depsipeptide which is formed of L-N-methylleucine [$(CH_3)_2$—CH—$CH_2$—CH(NH—$CH_3$)COOH], D-lactic acid [$CH_3$—CH(OH)COOH] and D-phenyllactic acid [$C_6H_5$—$CH_2$—CH(OH)COOH] via ester-bonds and amido-bonds and which can also be represented by the following formula (A'):

Cyclo-(L-MeLeu-D-Lac-L-MeLeu-D-PhLac-L-MeLeu-D-Lac-L-MeLeu-D-PhLac)  (A')

wherein MeLeu is an N-methylleucine residue represented by the following formula:

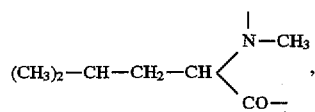

Lac is a lactic acid residue represented by the following formula:

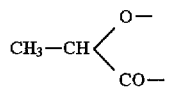

and PhLac is a phenyllactic acid residue represented by the following formula:

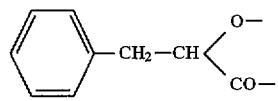

By the culture of the above filamentous fungus PF 1022 strain, the PF 1022B substance of the following formula (B), the PF1022C substance of the formula (C), the PF 1022D substance of the formula (D) and the PF 1022E substance of the formula (E) are produced in addition to the above PF 1022 substance. They have anthelmintic activities and were isolated by the present inventors [see Japanese Patent Application No. HEI 3-163085, now Japanese Patent Application Laid-Open (Kokai) No. HEI 5-170749; but concerning PF 1022E, Japanese Patent Application No. HEI 4-279094 (filed Oct. 19, 1992 but not yet laid open)].

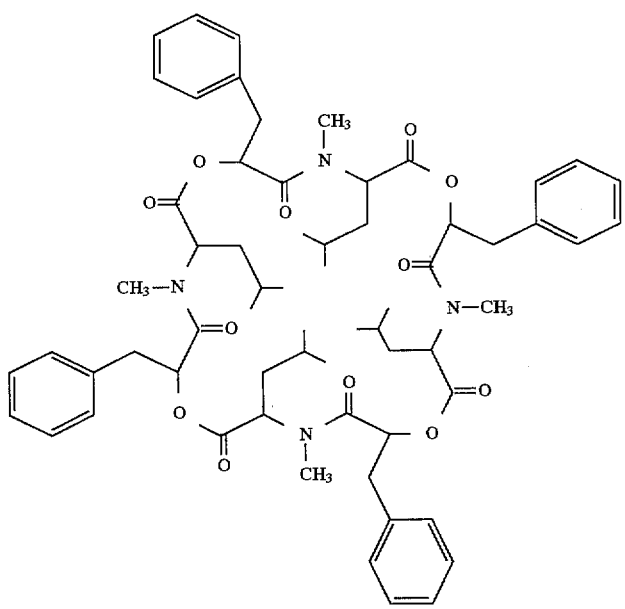
PF 1022B substance
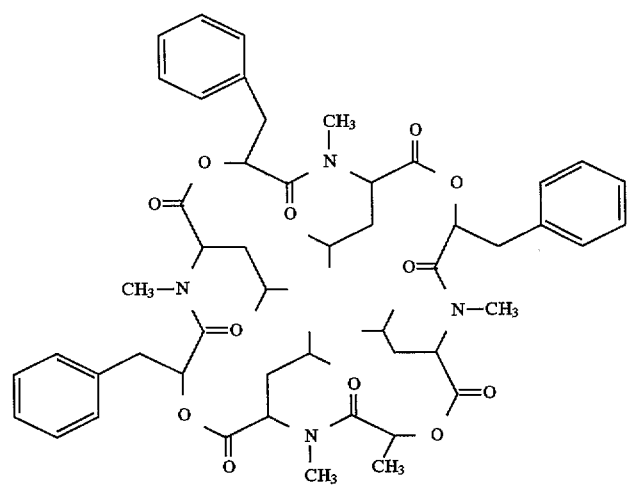
PF 1022C substance
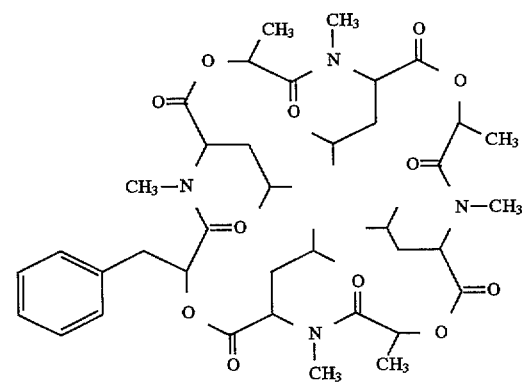
PF 1022D substance

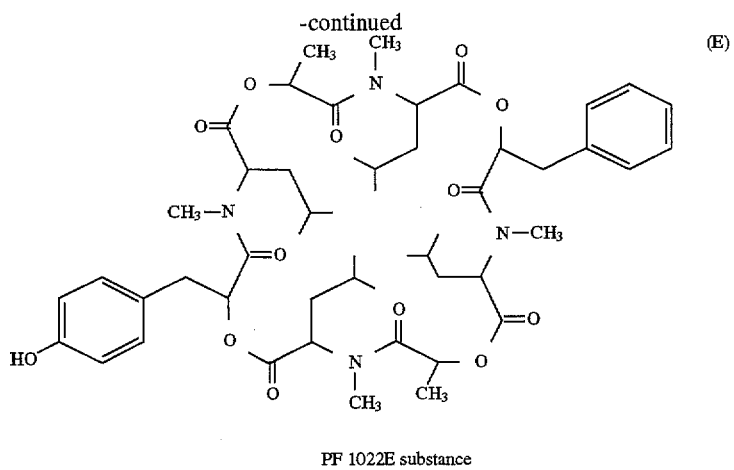

PF 1022E substance

Incidentally, the PF 1022E substance is a novel compound which has not been reported yet.

The above-described PF 1022 substance and PF 1022B to E substances all possess anthelmintic activities and have a marked structural characteristic in that they have a large cyclo-tetradepsipeptide structure as a basic skeleton, and that they have, as side chains, not only four N-methyl groups and four isobutyl groups but also 0–3 methyl group(s) and 1–4 benzyl group(s) and contain eight asymmetric carbon atoms in their molecules. In the skeletal cyclodepsipeptide structure of the group of these PF 1022 substances, a 24-membered ring is formed via 4 ester bonds and 4 amide-bonds. This structure can be presumed to play an important role on the development of biological activities.

So-called helmintic infections cause serious damage to the human and animal health and also to agriculture. There is a steady demand toward novel and useful substances having anthelmintic activities and also advantageous preparation processes for such anthelmintically active substances. Paying attention to such a demand, the present inventors studied with a view toward preparing and providing novel substances related to the PF 1022 substance.

The PF 1022 substance is a fermentation product of the above-described filamentous fungus. Makoto Ohyama et al. proposed, as a process of preparing the PF 1022 substance by total synthesis, a process which comprises the steps shown in the following reaction route map (A) [see Japanese Patent Application No. HEI 4-131139 (filed: May 22, 1992) and Japanese Patent Application Laid-Open No. HEI 5-320148 (laid open: Dec. 31 1993)].

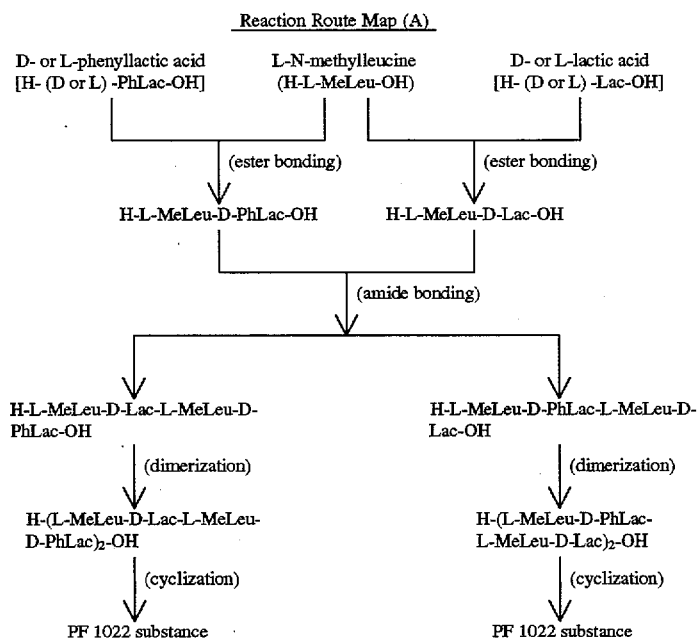

Incidentally, as one example of hitherto known totally synthetic processes for preparation of cyclodepsipeptides, the process reported in "Agric. Biol. Chem." 43(5), 1079–1083(1979), which is related to total synthesis of enniatin C, can be given.

DISCLOSURE OF THE INVENTION

With a view to providing novel cyclodepsipeptides which have a cyclo-tetradepsipeptide skeletal structure in common to the PF 1022 substance but exhibit anthelmintic activities superior to the PF 1022 substance, the present inventors have conducted a variety of research. As a result, it has been found that a series of novel derivatives or related products of the PF 1022 substance can each be synthesized either by hydrogenating, in the presence of a rhodium catalyst under mild reaction conditions, one or more phenyl groups in the plural benzyl groups of the PF 1022 substance or the PF 1022B substance or the PF 1022E substance so as to form cyclohexyl group(s), or by chemically modifying the phenyl groups through substitution reaction. It has also been found that a series of novel derivatives of the PF 1022 substance can each be prepared in accordance with total synthesis procedures by using L-N-methylleucine (L-MeLeu) or L-leucine in combination with an α-hydroxycarboxylic acid, particularly a D- or L-lactic acid derivative, which may contain a substituent on its β-carbon atom, and then condensing the carboxyl group of the leucine compound with the α-hydroxyl group of the lactic acid compound through an ester bond, condensing the carboxyl group of the resultant esterified product with the amino group of the leucine compound through an amide bond, continuing further condensation of the condensation product as needed, thereby to synthesize a chain-like tetradepsipeptide, followed by cyclizing the tetradepsipeptide.

A series of novel PF 1022 derivatives synthesized as described above by the present inventors can generically be represented by the below-described formula (I). It has been ascertained by animal tests that these synthesized novel derivatives have useful anthelmintic activities.

In a first aspect of the present invention, there is thus provided a cyclodepsipeptide, namely a PF 1022 derivative represented by the following formula:

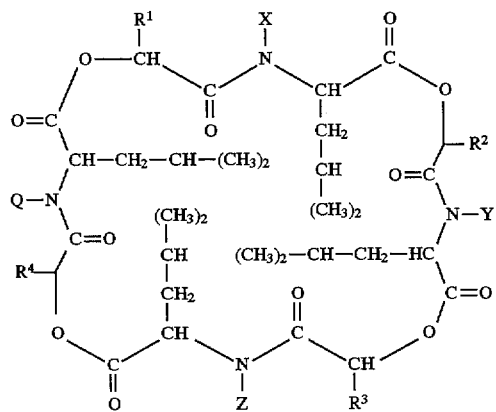

wherein (i) $R^2$ and $R^4$ are each a cyclohexylmethyl group or benzyl group, $R^1$ and $R^3$ are each a methyl group or cyclohexylmethyl group or benzyl group, and X, Y, Z and Q are each a methyl group, provided that at least one of $R^1$, $R^2$, $R^3$ and $R^4$ is a cyclohexylmethyl group, or (ii) $R^1$, $R^2$, $R^3$ and $R^4$ are each a linear or branched alkyl group containing 1 to 11 carbon atoms and may be the same or different from each other, and X, Y, Z and Q are each a methyl group, or (iii) $R^1$ and $R^3$ are each a linear or branched alkyl group containing 1 to 11 carbon atoms and may be the same or different from each other, and $R^2$ and $R^4$ are each an unsubstituted benzyl group, and X, Y, Z and Q are each a methyl group, provided that $R^3$ is not a methyl group when $R^1$ is a methyl group, or (iv) $R^1$, $R^2$ and $R^3$ are each a linear or branched alkyl group containing 1 to 11 carbon atoms and may be the same or different from each other and $R^4$ is a benzyl group bearing or not bearing substituent(s) on the phenyl nucleus of the benzyl group, and X, Y, Z are Q are each a methyl group, or (v) both of $R^1$ and $R^3$ are methyl groups while both of $R^2$ and $R^4$ are benzyl groups, and at least one of X, Y, Z and Q is hydrogen but the remainders thereof are all methyl groups, or (vi) $R^1$, $R^3$, X, Y, Z and Q are all methyl groups, $R^2$ is a benzyl group bearing or not bearing substituent(s) on the phenyl nucleus of the benzyl group and $R^4$ is a benzyl group bearing substituent(s) on the phenyl nucleus of the benzyl group.

BEST EMBODIMENTS FOR WORKING THE INVENTION

The above-described novel PF 1022 derivative of the formula (I) embraces therein, as preferred embodiments, such hydrogenated derivatives of the PF 1022 substance, as represented by below-described formula (I-i-a); such hydrogenated derivatives of the PF 1022B substance, as represented by the below-described formula (I-i-b); cyclodepsipeptides of the below-described formula (I-ii), cyclodepsipeptides of the below-described formula (I-iii), cyclodepsipeptides of the below-described formula (I-iv), cyclodepsipeptides of the below-described formula (I-v), cyclodepsipeptides of the below-described formula (I-vi-a) and cyclodepsipeptides of the below-described formula (I-vi-b).

(1) Hydrogenated derivatives of the PF 1022 substance, as represented by the following formula:

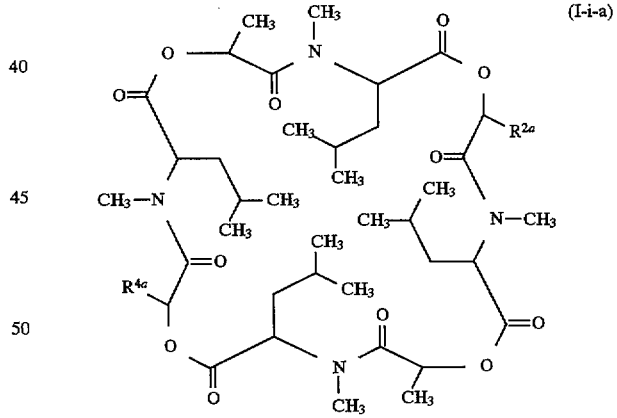

wherein $R^{2a}$ and $R^{4a}$ are each a cyclohexylmethyl or benzyl group, provided that at least one of $R^{2a}$ and $R^{4a}$ is a cyclohexylmethyl group.

(2) Hydrogenated derivatives of the PF 1022B substance, as represented by the following formula:

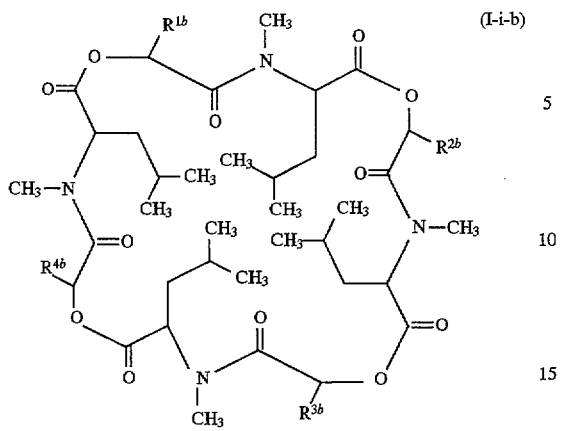

(I-i-b)

wherein $R^{1b}$, $R^{2b}$, $R^{3b}$ and $R^{4b}$ are each a cyclohexylmethyl group or benzyl group, provided that at least one of $R^{1b}$, $R^{2b}$, $R^{3b}$ and $R^{4b}$ is a cyclohexylmethyl group.

(3) Cyclodepsipeptides represented by the following formula:

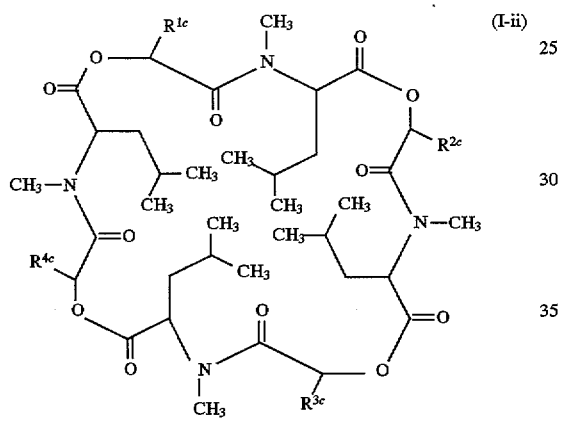

(I-ii)

wherein $R^{1c}$, $R^{2c}$, $R^{3c}$ and $R^{4c}$ are each a linear or branched alkyl group containing 1 to 11 carbon atoms, particularly an alkyl group containing 1 to 6 carbon atoms and may be the same or different from each other.

(4) Cyclodepsipeptides represented by the following formula:

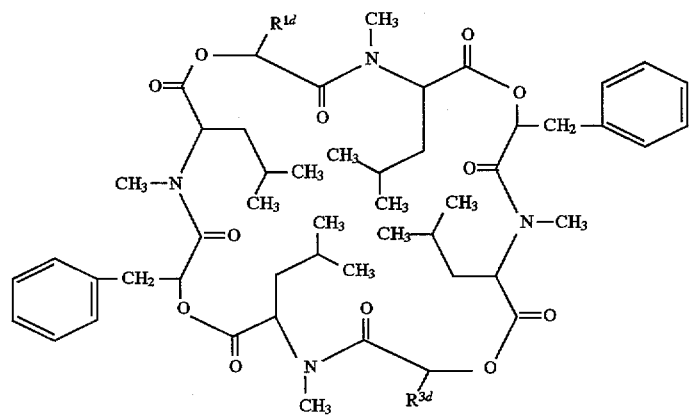

(I-iii)

wherein $R^{1d}$ and $R^{3d}$ are each a linear or branched alkyl group containing 1 to 11 carbon atoms, particularly an alkyl group containing 1 to 6 carbon atoms, and may be the same or different from each other, provided that $R^{1d}$ and $R^{3d}$ do not stand for methyl groups at the same time.

(5) Cyclodepsipeptides represented by the following formula:

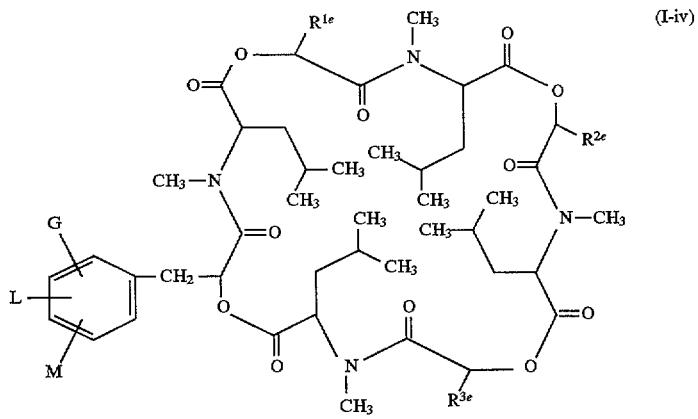

wherein $R^{1e}$, $R^{2e}$ and $R^{3e}$ are each a linear or branched alkyl group containing 1 to 11 carbon atoms, particularly an alkyl group containing 1 to 6 carbon atoms and may be the same or different from each other, and G, L and M denote independently a hydrogen or a substituent, particularly a halo group, hydroxyl group, an alkoxy group, a lower alkenyloxy group, a phenyl-lower alkoxy group, an alkylcarbonyloxy group, tetrahydropyranyloxy group or trityloxy group.

(6) Cyclodepsipeptides represented by the following formula:

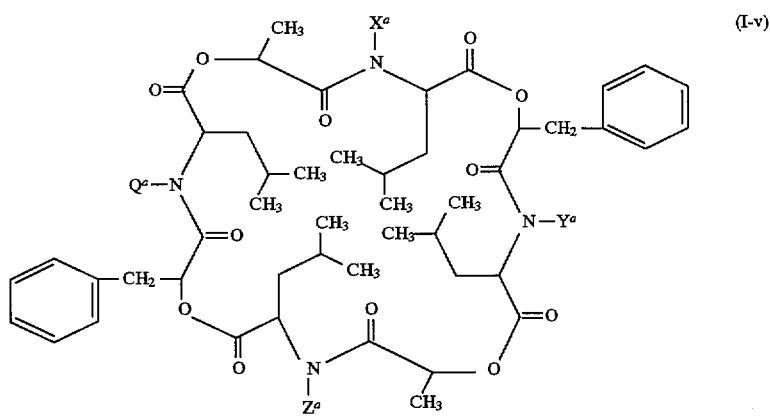

wherein at least one of $X^a$, $Y^a$, $Z^a$ and $Q^a$ is a hydrogen and the reminders thereof are all methyl groups; and preferably either $X^a$ and $Z^a$ are methyl groups while $Y^a$ and $Q^a$ are hydrogens, or $X^a$ and $Z^a$ are hydrogens while $Y^a$ and $Q^a$ are methyl groups.

(7) Cyclodepsipeptides represented by the following formula:

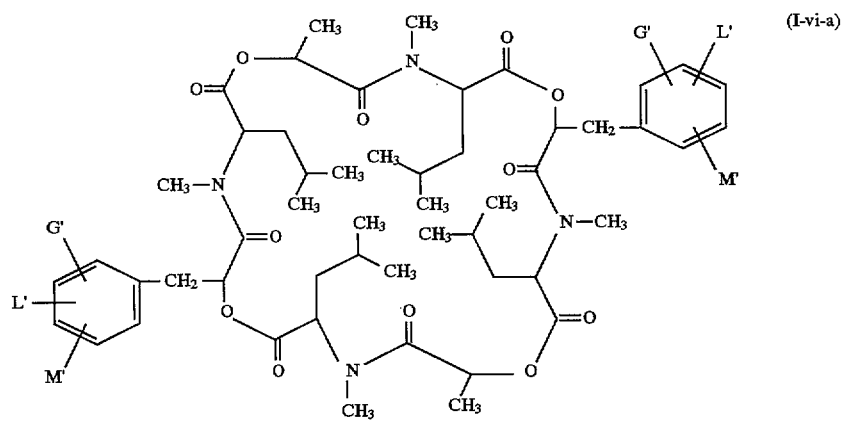

wherein G',L' and M' denote independently a substituent, particularly a halo group, hydroxyl group, an alkoxy group, a lower alkenyloxy group, a phenyl-lower alkoxy group, an alkylcarbonyloxy group, tetrahydropyranyloxy group or trityloxy group.

(8) Cyclodepsipeptides represented by the following formula:

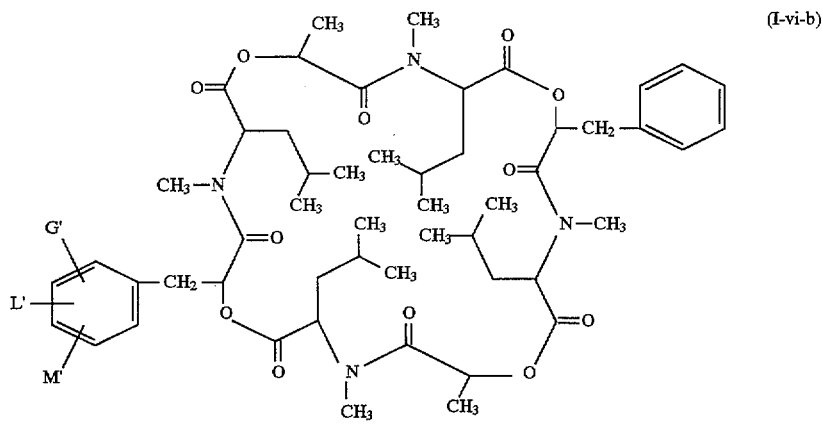

(I-vi-b)

wherein G', L' and M' denote independently a substituent, particularly a halo group, hydroxyl group, an alkoxy group, a lower alkenyloxy group, a phenyl-lower alkyl group, an alkylcarbonyloxy group, tetrahydropyranyloxy group or trityloxy group.

Examples of the PF1022 derivative of the formula (I) according to the first aspect of the present invention are shown below in Table 1. In Table 1, each Example number corresponds to the Example number of the corresponding compound whose Preparation Example will be described hereinafter.

In Table 1, Me stands for a methyl group, Bn a benzyl group, ChxyMe a cyclohexyl methyl group, i-Pr an isopropyl group, n-Bu an n-butyl group, sec-Bu a secondary butyl group and i-Bu an isobutyl group, respectively.

TABLE 1

| Example | Substance code | $R^1$ | $R^2$ | $R^3$ | $R^4$ | X | Y | Z | Q |
|---|---|---|---|---|---|---|---|---|---|
| 1 & 2 | PF1022-AHH | Me | ChxyMe | Me | Bn | Me | Me | Me | Me |
| 1 | PF1022-ADH | Me | ChxyMe | Me | ChxyMe | Me | Me | Me | Me |
| 1 | PF1022-BTH | ChxyMe | ChxyMe | ChxyMe | ChxyMe | Me | Me | Me | Me |
| 3 | PF1022-002 | Me | Me | Me | Me | Me | Me | Me | Me |
| 13 | PF1022-209 | Me | i-Pr | Me | i-Pr | Me | Me | Me | Me |
| 15 | PF1022-217 | Me | n-$C_{16}H_{13}$ | Me | n-$C_6H_{13}$ | Me | Me | Me | Me |
| 9 | PF1022-203 | i-Pr | Bn | i-Pr | Bn | Me | Me | Me | Me |
| 10 | PF1022-205 | sec-Bu | Bn | sec-Bu | Bn | Me | Me | Me | Me |
| 11 | PF1022-207 | n-Bu | Bn | n-Bu | Bn | Me | Me | Me | Me |
| 12 | PF1022-225 | Me | Bn | n-Bu | Bn | Me | Me | Me | Me |
| 14 | PF1022-216 | Me | n-$C_6H_{13}$ | Me | Bn | Me | Me | Me | Me |
| 16 | PF1022-218 | Me | Bn | Me | Bn | Me | H | Me | H |
| 17 | PF1022-219 | Me | Bn | Me | Bn | H | Me | H | Me |
| 4 | PF1022-003 | Me | Bn | Me | i-Bu | Me | Me | Me | Me |

TABLE 1-continued

[Structure of general formula (I) showing a cyclic depsipeptide with substituents R¹, R², R³, R⁴, X, Y, Z, Q]

| Example | Substance code | R¹ | R² | R³ | R⁴ | X | Y | Z | Q |
|---|---|---|---|---|---|---|---|---|---|
| 6 | PF1022E | Me | Bn | Me | p-hydroxybenzyl | Me | Me | Me | Me |
| 5 | PF1022-005 | Me | Bn | Me | p-methoxybenzyl | Me | Me | Me | Me |
| 7 | PF1022-201 | Me | p-benzyloxybenzyl | Me | p-benzyloxybenzyl | Me | Me | Me | Me |
| 8 | PF1022-202 | Me | p-hydroxybenzyl | Me | p-hydroxybenzyl | Me | Me | Me | Me |
| 18 | PF1022-215 | Me | Bn | Me | p-t-butoxybenzyl | Me | Me | Me | Me |
| 19 | PF1022-006 | Me | Bn | Me | p-stearoyloxybenzyl | Me | Me | Me | Me |
| 20 | PF1022-011 | Me | Bn | Me | 3,5-di-iodo-4-hydroxybenzyl | Me | Me | Me | Me |
| 21 | PF1022-012 | Me | Bn | Me | 3,5-di-iodo-4-methoxybenzyl | Me | Me | Me | Me |
| 22 | PF1022-013 | Me | Bn | Me | p-isobutyoxycarbonyloxybenzyl | Me | Me | Me | Me |
| 23 | PF1022-016 | Me | Bn | Me | p-ethoxybenzyl | Me | Me | Me | Me |
| 24 | PF1022-018 | Me | Bn | Me | p-n-propoxybenzyl | Me | Me | Me | Me |
| 25 | PF1022-019 | Me | Bn | Me | p-isopropoxybenzyl | Me | Me | Me | Me |
| 26 | PF1022-020 | Me | Bn | Me | p-allyloxybenzyl | Me | Me | Me | Me |
| 27 | PF1022-021 | Me | Bn | Me | p-n-butoxybenzyl | Me | Me | Me | Me |
| 28 | PF1022-022 | Me | Bn | Me | p-benzyloxybenzyl | Me | Me | Me | Me |
| 29 | PF1022-023 | Me | Bn | Me | 3,5-dichloro-4-hydroxybenzyl | Me | Me | Me | Me |
| 30 | PF1022-025 | Me | Bn | Me | 3,5-dibromo-4-hydroxybenzyl | Me | Me | Me | Me |
| 31 | PF1022-026 | Me | Bn | Me | 3,5-dibromo-4-methoxybenzyl | Me | Me | Me | Me |
| 32 | PF1022-029 | Me | Bn | Me | p-n-octyloxybenzyl | Me | Me | Me | Me |
| 33 | PF1022-224 | Me | Bn | Me | p-tetrahydropyranyloxybenzyl | Me | Me | Me | Me |
| 34 | PF1022-223 | Me | Bn | Me | p-trityloxybenzyl | Me | Me | Me | Me |

In Table 1, the substances (substance code: PF1022-AHH, -ADH and -BTH) of Example 1 are examples of the derivative represented by the general formula (I-i-a) or (I-i-b), while the substances (substance code: PF1022-209 and -217) of Example 13 and Example 15 are examples of the derivative represented by the general formula (I-ii). The substances (substance code: PF1022-203, -205, -207 and -225) of Examples 9, 10, 11 and 12 are examples of the derivative represented by the general formula (I-iii). The substance (substance code: PF1022-216) of Example 14 is an example of the derivative represented by the general formula (I-iv). The substances (substance code: PF1022-218 and -219) of Examples 16 and 17 are examples of the derivative represented by the general formula (I-v). The substances (substance code: PF1022-201 and -202) of Examples 7 and 8 are examples of the derivative represented by the general formula (I-vi-a). Furthermore, the substances (substance code: PF1022-005, PF1022E, PF1022-215, -006, -011, -012, -013, -016, -018, -019, -020, -021, -022, -023, -025, -026, -029, -224 and -223) of Examples 5, 6 and 18–34 are examples of the derivative represented by the general formula (I-vi-b).

Processes of preparing the PF1022 derivative of the general formula (I) according to the present invention will hereinafter be described.

(a) Preparation of the PF1022 substance or PF1022B substance by hydrogenation

Among the derivatives of the general formula (I) according to the present invention, hydrogenated derivatives or hydro-derivatives of the general formula (I-i-a) or (I-i-b) can each be synthesized by using, as a starting material, the PF1022 substance or PF1022B substance as prepared by a fermentative method.

Chemical modification, particularly hydrogenation, of a benzene ring such as a phenyl group is generally regarded to be more difficult than the other reactions such as nitration or acylation which is the reaction by an electrophilic substitution. In general, hydrogenation made at high temperature and under high pressure is widely made to reduce a phenyl group into a cyclohexyl group. The PF1022 substance has a complex chemical structure as occurred naturally. It is presumed that if the PF 1022 substance is subjected to hydrogenation under conventional conditions at high temperature and under high pressure, decomposition reaction can also be involved by hydrogenolysis. Procedures of hydrogenation under milder reaction conditions, that is, hydrogenation made at normal temperature under normal pressure are desirable for effecting the reduction of the phenyl groups in the PF 1022 substance. From such a viewpoint, the present inventors have proceeded with an investigation on the usability of various reducing catalysts. As a result, it has been found that a rhodium catalyst is most suitable for the hydrogenation of the phenyl groups in the side-chain benzyl groups of the PF1022 substance to form cyclohexyl groups.

Examples of reducing catalysts, which are usable in the process for preparing the invention derivative of the general formula (I-i-a) or (I-i-b) from the PF1022 substance by hydrogenation, include rhodium, and rhodium-carrier catalysts such as rhodium-carbon and rhodium-alumina, and cationic rhodium complexes such as tris(triphenylphosphine)rhodium. In practice, a rhodium-carbon catalyst is preferred. This hydrogenation process is able to minimize the hydrogen pressure and the extent of heating upon the catalytic reduction, but elevated pressure and heating to some extents are allow able so that the reaction time can be shortened and production of by-products can be suppressed. For a smooth progress of the reaction, it is desired to dissolve the starting materials in an inert solvent such as methanol, ethanol or ethyl acetate and then to conduct the reaction while stirring the resultant solution.

Isolation of the target product (I-i-a) or (I-i-b) after the reaction can be conducted by a well-known method, for example, filtration, column chromatography or a fractional crystallization method using an inert solvent.

(b) Preparation by a totally synthetic process

Derivatives of the general formula (I) according to the present invention can be prepared by a totally synthetic process, that is, by providing the following compounds (1), (2), (3), (4), (5) and (6) and then condensing them successively in proper combinations through an ester-bond or an amide-bond.

The starting materials to be employed are as follows:

Compound (1): N-methyl-L-leucine (structural formula: $(CH_3)_2$—CH—$CH_2$—CH(NH—$CH_3$)COOH, abbreviation: H-L-MeLeu-OH)

Compound (2): L-leucine (structural formula: $(CH_3)_2$—CH—$CH_2$—CH($NH_2$)COOH, abbreviation: H-L-Leu-OH)

Compound (3): D- or L-α-hydroxycarboxylic acid, preferably, D- or L-lactic acid or a lactic acid derivative having a desired substituent introduced at its β-carbon atom, each being represented by the following formula:

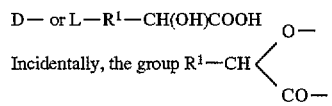

will hereinafter be abbreviated as $A^1$.

Compound (4): D- or L-α-hydroxycarboxylic acid represented by the following formula:

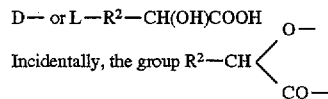

will hereinafter be abbreviated as $A^2$.

Compound (5): D- or L-α-hydroxycarboxylic acid represented by the following formula:

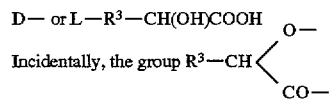

will hereinafter be abbreviated as $A^3$.

Compound (6): D- or L-α-hydroxycarboxylic acid represented by the following formula:

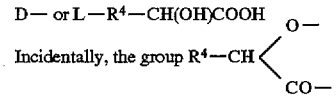

will hereinafter be abbreviated as $A^4$.

In the above formulas, $R^1$, $R^2$, $R^3$ and $R^4$ have the same meanings as $R^1$, $R^2$, $R^3$ and $R^4$ defined in connection with the general formula (I) given hereinbefore.

In the first step of the totally synthetic process, the carboxyl group of Compound (1) or (2) is reacted with the α-hydroxyl group of Compound (3), (4), (5) or (6). The following four Compounds (7)–(10) each having an amino group at one end thereof and a carboxyl group at the other end thereof can therefore be prepared as primary condensates containing the ester-linkage.

Compound (7): H-L-MeLeu(or Leu)-D-$A^1$-OH

Compound (8): H-L-MeLeu(or Leu)-D-$A^2$-OH

Compound (9): H-L-MeLeu(or Leu)-D-$A^3$-OH

Compound (10): H-L-MeLeu(or Leu)-D-$A^4$-OH

In the second and subsequent steps of the totally synthetic process, two of Compounds (7)–(10) are condensed with each other in proper combinations via an amide-bond, whereby Compound (11), Compound (12), Compound (13) and Compound (14) are synthetically prepared in the order as shown schematically in the below-described reaction route map B or C, or Compound (15) is synthetically obtained in the orders schematically shown in the hereinafter given reaction route map D. By cyclizing, via an amide-bond, chain-like Compound (13) or Compound (15) which has an amino group at one end thereof and a carboxyl group at the other end thereof, a cyclic PF1022 derivative of the general formula (I) can be prepared.

Compound (11): H-L-MeLeu(or Leu)-D-$A^1$-L-MeLeu(or Leu)-D-$A^2$-OH

Compound (12): H-L-MeLeu(or Leu)-D-$A^1$-L-MeLeu(or Leu)-D-$A^2$-L-MeLeu(or Leu)-D-$A^3$-OH Compound (13): H-L-MeLeu(or Leu)-D-$A^1$-L-MeLeu(or Leu)-D-$A^2$-L-MeLeu(or Leu)-D-$A^3$-L-MeLeu(or Leu)-D-$A^4$-OH Compound (14): H-L-MeLeu(or Leu)-D-$A^3$-L-MeLeu(or Leu)-D-$A^4$-OH Compound (15): H-(L-MeLeu(or Leu)-D-$A^1$-L-MeLeu(or Leu)-D-$A^2$)-OH Compounds (3), (4), (5) and (6), such a derivative of the formula (I) wherein $R^1$, $R^2$, $R^3$ and $R^4$ individually represent an isobutyl group can be obtained. For example, when 2-hydroxyoctanoic acid is used as Compound (4), such a

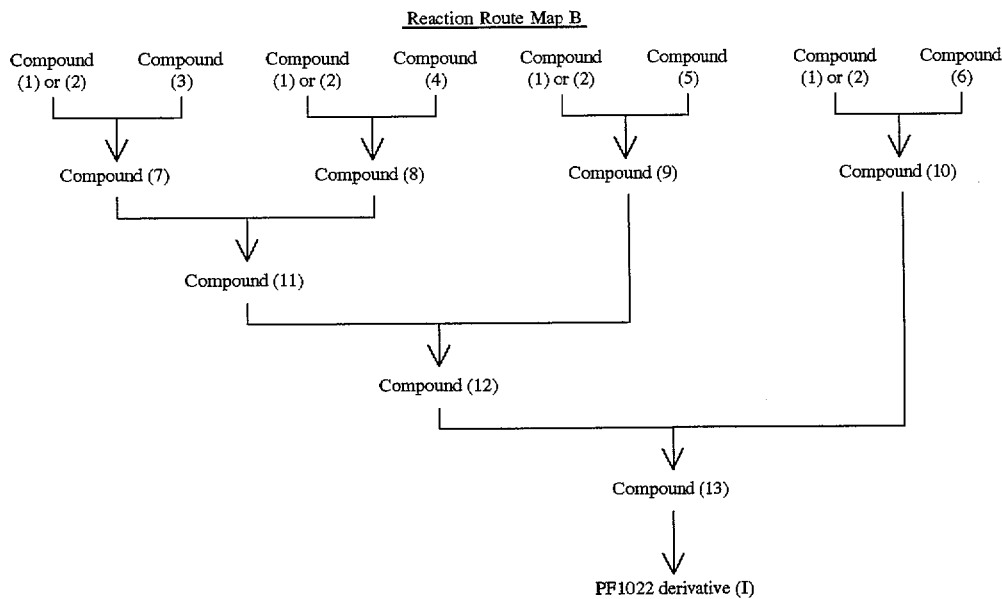

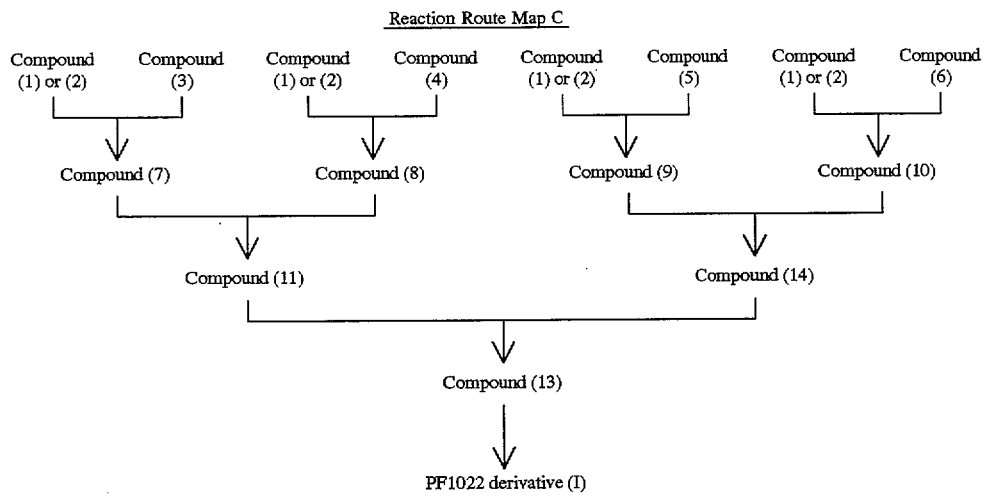

For instance, when lactic acid is employed as each of Compounds (3), (4), (5) and (6), such a derivative of the general formula (I), where $R^1$, $R^2$, $R^3$ and $R^4$ individually represent methyl group, can be obtained. When 2-hydroxyisovaleric acid is used as each of Compounds (3), (4), (5) and (6), such a derivative of the general formula (I), where $R^1$, $R^2$, $R^3$ and $R^4$ individually represent an isopropyl group, can be obtained. When 2-hydroxyhexanoic acid is employed as each of Compounds (3), (4), (5) and (6), such a derivative of the formula (I), where $R^1$, $R^2$) $R^3$ and $R^4$ individually represent a n-butyl group, can be obtained. When 2-hydroxy-3-methylpentanoic acid is employed as each of Compounds (3), (4), (5) and (6), such a derivative of the formula (I) wherein $R^1$, $R^2$, $R^3$ and $R^4$ individually represent a secondary butyl group can be obtained. When 2-hydroxy-4-methyl-n-valeric acid is employed as each of derivative of the formula (I) wherein $R^2$ represents n-$C_6H_{13}$ can be obtained. When phenyllactic acid and p-hydroxyphenyllactic acid are employed as Compounds (4) and (6), respectively, such a derivative of the formula (I) wherein $R^2$ and $R^4$ represent benzyl and p-hydroxybenzyl groups, respectively, can be obtained.

In general, the a-hydroxycarboxylic acid which is Compound (4), (5) or (6) can be prepared by reacting a corresponding α-amino acid with sodium nitrite to convert its amino group into a diazo group (—$N_2$), and then converting the diazo group to a hydroxyl group by acid treatment.

When the groups $R^1$ and $R^3$ of the PF1022 derivative having the general formula (I) are the same while the groups $R^2$ and $R^4$ are the same, that is to say, when the $R^1$ of the starting Compound (3) and the $R^3$ of Compound (5) are the same while the $R^2$ of the starting Compound (4) and the $R^4$ of Compound (6) are the same, it is only necessary to provide Compounds (3) and (4) as the starting α-hydroxycarboxylic acid for the preparation of such a PF1022 derivative in accordance with the totally synthetic process. Such target PF1022 derivative (I) (wherein $R^1=R^3$, and also $R^2=R^4$) can be prepared by using Leucine compound (1) or (2) in combination with Compound (3) or Compound (4), condensing them by esterification, preparing each of intermediates (7) and (8) with forming the amide-bond, producing the chain-like Compound (15) via Compounds (11), and then cyclizing Compound (15), in accordance with the order as illustrated in the below-described reaction route map D.

(6), that is, α-carboxyl-protected α-hydroxycarboxylic acids are employed. As a condensation method using the ester-bond, it is desired to conduct the condensation with employing Compounds (3)–(6), each of which has its α-hydroxyl group in the free form, in the presence of a condensation agent. When the carboxyl-protected Compound (3), (4), (5) or (6) is the D-isomer, its condensation is conducted in the presence of both DCC and an additive (a reagent, such as N-hydroxysuccinic acid imide, N-hydroxybenzotriazole or the like, which does not cause racemization in an ordinary peptide-forming reaction). When the carboxyl-protected Compound (3), (4), (5) or (6) is the L-isomer, on the other hand, condensation is conducted while inverting the confor-

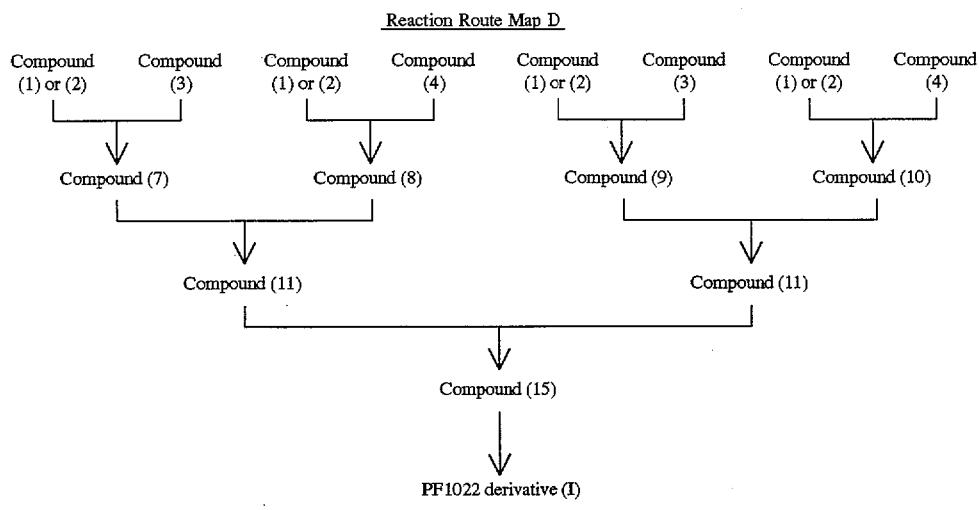

Reaction Route Map D

In the PF1022 derivative of the general formula (I) and also in the α-hydroxycarboxylic acid compounds (3)–(6) as the starting materials, $R^1$, $R^2$, $R^3$ and $R^4$ can each be a $C_1$–$C_{11}$ alkyl group. Specific examples of such an alkyl group include methyl, ethyl, propyl, (specifically, n-propyl, iso-propyl), butyl (specifically, n-methyl, iso-butyl, sec-butyl, tert-butyl), pentyl (specifically, n-pentyl, iso-pentyl, sec-pentyl, 1,2-dimethylpropyl, neo-pentyl, 1-ethylpropyl, 1,1-dimethylpropyl), hexyl, heptyl, octyl, nonyl and decyl groups. Preferred are lower ($C_1$–$C_6$) alkyl groups.

When, in the compound of the general formula (1) or in Compound (3), (4), (5) or (6), $R^1$, $R^2$, $R^3$ and $R^4$ each represents a substituted or unsubstituted phenyl or benzyl group, on the other hand, specific examples of such a group include phenyl; o-, m- and p-hydroxyphenyl; o-, m- and p-($C_{1-10}$)alkylphenyl; o-, m- and p-($C_{1-10}$)alkoxyphenyl; o-, m-, and p-halogeno(F, Cl, Br, I)phenyl. Other examples include benzyl; o-, m- and p-hydroxybenzyl; o-, m- and p-($C_{1-10}$)alkylbenzyl; o-, m- and p-($C_{1-10}$)alkoxybenzyl; and o-, m-, and p-halogeno(F, Cl, Br, I)benzyl. The number of the substituents on the phenyl nucleus of the benzyl group can be 1–4.

The process for preparation of the PF1022 derivative represented by the general formula (I) in accordance with the totally synthetic process will hereinafter be described with the above-described reaction route map (B) or (C). In brief, in the first step, Compounds (7), (8), (9) and (10) are prepared by condensing Compound (1) or (2) with Compound (3); Compound (1) or (2) with Compound (4); Compound (1) or (2) with Compound (5); and Compound (1) or (2) with Compound (6) via an ester-bond, respectively.

At this time, the amino-protected leucine compound (1) or (2),and α-carboxyl-protected Compounds (3), (4), (5) and mation of the α-hydroxyl group of Compound (3), (4), (5) or (6). The condensation method by the Cohen's reaction is desired because it does not cause racemization.

Furthermore, the amino-protected leucine compound (1) or (2) can be condensed, through an ester-bond, with a reactive derivative at the α-OH group of the carboxyl-protected Compound (3), (4), (5) and (6). In this method, when the α-carboxyl-protected compound (3), (4), (5) or (6) is the D-isomer, it is desired that the compound has been made reactive by substituting the α-hydroxyl group by a chlorine atom, a bromine atom or the like. When the compound is the L-isomer, it is desired that the α-hydroxyl group has been converted into a sulfonate ester such as tosylate, methanesulfonate or the like.

According to the above condensation method, there is prepared the ester-type compound (7), (8), (9) or (10) in which the carboxyl and amino groups are both protected. One of the protecting groups introduced in Compound (1) or (2) and Compounds (3)–(6), which are starting compounds employed for the preparation of the above compounds (7)–(10), should be preferentially removable.

Examples of such a carboxyl-protecting group include those removable under acid hydrolytic or reducing conditions, such as t-butyl, benzyl, p-methoxybenzyl, benzhydryl and trityl groups; and those removable under neutral conditions such as an allyl group.

Examples of the amino-protecting group include those removable under acid hydrolytic or reducing conditions such as benzyloxycarbonyl, t-butyloxycarbonyl, p-methoxybenzyloxycarbonyl and formyl groups; and those removable under neutral conditions and commonly used in peptide chemistry, such as an aryloxycarbonyl group.

It is necessary to remove the carboxyl-protecting group and the amino-protecting group preferentially and independently from each of the protected ester-type compounds (7), (8), (9) and (10) so obtained. When the carboxyl-protecting group is removable under reducing conditions, it is necessary to select as the amino-protecting group an amino-protecting group removable under acid hydrolytic conditions. The converse case is also feasible. When the amino-protecting group is removable under neutral conditions, for example, an aryloxycarbonyl group, it is necessary to select as the carboxyl-protecting group a carboxyl-protecting group removable under acid hydrolytic conditions. The converse case is also feasible.

With regard to a method for removal of the carboxyl-protecting group or amino-protecting group, when the protecting group is removable under acid hydrolytic conditions, it is treated with trifluoroacetic acid, methanesulfonic acid, trifluoromethanesulfonic acid or the like. Treatment with trifluoroacetic acid is most preferred. When it is removable under reducing conditions, treatment under catalytic reduction conditions using a palladium catalyst is desired. When the protecting group is removable under neutral conditions, for example, an aryl group, aryloxycarbonyl group or the like, it may be reacted with potassium 2-ethylhexanoate in the presence of zero-valence palladium catalyst for the deprotection.

In the next step, Compound (11) is prepared, as shown in the reaction route map B, by condensing, the deprotected Compound (7) with the deprotected Compound (8) through an amide-bond. As described above, it is possible to form an amide bond between the amino group of Compound (7) and the carboxyl group of Compound (8) or between the amino group of Compound (8) and the carboxyl group of Compound (7) when the condensation is done between Compounds (7) and (8). Compound (11) obtained by the condensation of Compounds (7) and (8) is condensed further with Compound (9). Here it is possible to form an amide-bond between the amino group of Compound (11) and the carboxyl group of Compound (9) or between the amino group of Compound (9) and the carboxyl group of Compound (11). Compound (12) obtained by the condensation of Compounds (11) and (9) is then condensed with Compound (10). In this condensation step, it is possible to form an amide-bond between the amino group of Compound (12) and the carboxyl group of Compound (10) or between the amino group of Compound (10) and the carboxyl group of Compound (12). As a result, Compound (13) can be prepared.

In the above respective condensation steps, the removal and fresh introduction of a protecting group are conducted appropriately as needed to obtain a desired amide-bond.

As described in the reaction route map C, Compound (9) can also be condensed with Compound (10). In this case, it is possible to form an amide-bond between the amino group of Compound (9) and the carboxyl group of Compound (10) or between the amino group of Compound (10) and the carboxyl group of Compound (9). Compound (11), which has been obtained by the condensation of Compounds (7) and (8), can be condensed with Compound (14), which has been obtained by the condensation of Compound (9) and Compound (10). In this case, it is possible to form an amide-bond between the amino group of Compound (11) and the carboxyl group of Compound (14) or between the amino group of Compound (14) and the carboxyl group of Compound (11). As described in the reaction route map D, Compound (15) can be prepared by bonding two molecules of Compound (11) together through an amide-bond.

By the intramolecular ring closure of Compound (13) or Compound (15) so obtained, a derivative of the general formula (I) can be prepared. This ring closure is effected by treating Compound (13) or Compound (15) using dicyclohexylcarbodiimide (DCC) or 1-(3-dimethylaminopropyl)-3-ethylcarbodiimide (EDCI) and an additive [N-hydroxysuccinic acid imide (HOSU), 1-hydroxybenzotriazole (HOBt), or the like] in combination.

Examples of solvents usable in the above ring-closure reaction include ether-solvents such as ether, tetrahydrofuran (THF) and 1,4-dioxane, and aprotic solvents such as N,N-dimethylformamide (DMF), acetonitrile and chloroform. Preferred is a mixed solvent of tetrahydrofuran and N,N-dimethylformamide. The ring-closure reaction can be carried out at 0°–50° C., preferably 20°–30° C.

The totally synthetic process as described above is suited for the preparation of the derivatives of the formulae (I-ii), (I-iii), (I-iv) and (I-v) among the derivatives of the general formula (I) according to the present invention. (c) Preparation by introduction of substituent(s) into the PF1022 or PF1022E substance Among the novel derivatives of the general formula (I), the derivatives of the formulas (I-vi-a) and (I-vi-b) can be prepared by introducing, in accordance with known chemical methods, various substituents for the hydrogen(s) on the benzene ring (phenyl group) of the benzyl group, that is, a side chain of the PF1022 substance or in the phenolic hydroxyl group on the p-hydroxyphenylmethyl group (namely, benzyl group), that is, a side chain of the PF1022 E substance [refer to Japanese Patent Application HEI 4-279094 (not yet laid open), and the synthetic Example which will be described subsequently in Example 6)].

Examples of the substituents, which may be introduced in the benzene ring, namely, the phenyl nucleus of the benzyl group of the PF1022 substance or in the phenolic hydroxyl group on the benzyl group of the PF1022E substance, include linear or branched alkyl groups, alkenyl groups, alkynyl groups, substituted or unsubstituted benzyl groups, diphenylmethyl group, triphenylmethyl group and acyl groups. Particularly preferred are alkanoyl, carbamoyl, methoxymethyl, methylthiomethyl and tetrahydropyranyl groups. Examples of the substituent(s) replaceable for the hydrogen(s) on the benzene ring include halogen atoms, as well as such substituents as replaceable for the hydrogen(s) on an aromatic ring by ordinary electrophilic substitution.

The above substituent-introducing reaction can be performed in an inert solvent by etherification, acylation, carbamoylation or the like. The etherification can be conducted by a reaction with diazomethane or diphenyldiazomethane, a reaction with isobutene or dihydropyrane in the presence of an acid catalyst, or a reaction with an alkyl halide, an alkenyl halide, an alkynyl halide, a benzyl halide, a substituted benzyl halide, or a triphenylmethyl chloride (namely, trityl chloride). While, the acylation can be conducted by a reaction with an acyl halide or alkyl chlorocarbonate in the presence of an organic base such as triethylamine or an inorganic base such as potassium carbonate. Most of the well-known reactions for the modification of a phenolic hydroxyl group can be applied to as such. To the phenolic hydroxyl group at the para position which is active to the electrophilic substituting reaction, the halogenation or other well-known electrophilic substitutions can also be applied.

Derivatives of the general formula (I) according to the present invention, namely, derivatives of the formulae (I-i-a), (I-i-b), (I-ii), (I-iii), (I-iv), (I-v), (I-vi-a) and (I-vi-b) all have useful anthelmintic activities and show a low acute toxicity to mammarian animals.

The novel PF1022 derivatives according to the present invention can be converted to their acid addition salts by reacting them with a pharmaceutically acceptable inorganic acid such as hydrochloric acid, sulfuric acid or phosphoric acid, or a pharmaceutically-acceptable organic acid such as acetic acid, propionic acid, citric acid or methanesulfonic acid. In addition, the PF1022 derivatives of the present invention or their salts can be formulated into anthelmintic compositions by mixing them with a pharmaceutically acceptable, solid or liquid carrier.

According to a second aspect of the present invention, therefore, there is provided an anthelmintic composition characterized in that the composition comprises a novel cyclodepsipeptide represented by the general formula (1) or its salt as an active ingredient.

The novel derivative of the general formula (I) according to the present invention or the composition containing the derivative can be administered to animals orally or parenterally, for example, rectally. Through a proper preliminary test, the dose of the derivative can be determined depending on the kind of a parasite to be eliminated, the kind of a host animal to be treated and various other factors. As a general guideline, when orally administered, for example, for the elimination of fowl roundworms, oral administration of the compound of the formula (I) at a dose of 0.05 mg/kg or greater, preferably 0.2 mg to 3 mg/kg is recognized to exhibit the anthelmintic action against parasites.

The compound of the general formula (I) of the present invention can be formulated into an anthelmintic composition just in the same manner as for the PF1022 substance, which is described in Japanese Patent Application Laid-Open No. HEI 3-35796 or European Patent Application Publication No. 0382173 A2.

Examples of the animal to which the PF1022 derivative of the formula (I) of this invention can be applied as an anthelmintic may include domestic animals, poultry, experimental animals and pets, such as swine, cattle, horses, rabbits, sheep, goats, domestic fowls, ducks, turkeys, mice, white rats, guinea pigs, monkeys, dogs, cats and small birds. Illustrative parasites on these animals include parasites on cattle and sheep such as twisted stomachworms, stomach-worms belonging to the genus Ostertagia, small hairworms, nematodes belonging to the genus Cooperia, nodularworms belonging to the genus Oesophagostomum, amphisomes, intestinal tapeworms (*Moniezia benedeni*), lung worms and liver flukes; parasites on swine such as roundworms, whip-worms and nodularworms; parasites on dogs such as roundworms, hookworms, whipworms and heart worms; parasites on cats such as roundworms and *Spirometra mansoni*; and parasites of chickens such as roundworms, hair-worms and cecal worms. The compound of the present invention is also effective for the elimination of parasites on human bodies such as roundworms, pinworms, hookworms (*Ancylostoma duodenale, Ancylostoma ceylanicum, Necator americanus*), oriental hairworms, strongyloides worms and whipworms.

The novel PF1022 derivative according to the present invention can be used for the treatment and prevention of parasitic infections. For the treatment, the derivative may be administered orally or parenterally. Upon oral administration, a liquid preparation of the derivative may be forcedly administered using a stomach catheter or the like, or administered after mixing it with daily feed or drinking water, or administered in an ordinary dosage form suitable for oral administration, such as tablets, capsules, pellets, boluses, powders or soft capsules. Upon parenteral administration, it may be administered subcutaneously, intramuscularly, intravenously, intraperitoneally or through a similar route by injecting the derivative of the formula (I) prepared in the form of a water-insoluble preparation in peanut oil, soybean oil or the like or in the form of a water-soluble preparation in glycerol, polyethylene glycol, etc.

For the prevention of parasitic infections, it is a common practice to administer the PF1022 derivative orally as a a mixture of it with daily feed. Although no limitation is imposed on the administration period in the case of preventive purposes, it is, in most cases, sufficient to administer it for about 2 months in the case of broiler chickens and for about 5 months in the case of swine.

The dose of the PF1022 derivative according to the present invention may vary depending on the kind of the animal to be treated, the kind of the parasite and the method of administration. For instance, when fowl roundworms are to be eliminated by oral administration of a liquid preparation using a stomach catheter, it can be administered at 0.05 mg/kg or more. For the preventive purposes, the derivative can be mixed with feed at a concentration of 1 ppm or higher, preferably 5 to 10 ppm and administered continuously.

Furthermore, a solution or suspension of the PF1022 derivative of the present invention in a liquid carrier can be administered to animals by subcutaneous or intramuscular injection, etc., For parenteral administration, non-aqueous formulations using a vegetable oil such as peanut oil or soybean oil are employed. Aqueous parenteral formulations which contain a water-soluble carrier such as glycerol or polyethylene glycol can also be employed for parenteral administration. These formulations generally contain the compound of the present invention in an amount of 0.1 to 10 wt. %. Even when the PF1022 derivative of the present invention is orally administered to mice at the dose of 300 mg/kg, normal body-weight gains are obtained without any abnormalities. This indicates the low toxicity of this substance.

The anthelmintic activities of the PF1022 derivative of the general formula (I) according to this invention will be described by the following Tests.

Test 1
Fowl Roundworm Eliminating Test

Fowls (three fowls per group), which had been artificially infected with fowl roundworms and whose infection therewith had been confirmed by scatoscopy, were used as experimental animals. Upon administration of each test substance, the test substance weighed in a dose (mg) accurately calculated on the basis of the body weight (kg) of each fowl was suspended in carboxymethylcellulose-containing water, and the resulting suspension was administered orally as a single dose unit using a stomach tube. After the administration, the worms eliminated from the fowls were counted daily. Seven days after the administration, the fowl was sacrificed and autopsied and the worms remaining in its intestinal tract were counted. The percent elimination was calculated in accordance with the following calculation equation:

$$\frac{\%}{\text{Elimination}} = \frac{\text{Number of worms eliminated during 7 days}}{\text{Number of worms eliminated during 7 days} + \text{Number of remaining worms}} \times 100(\%)$$

Test results are summarized in Table 2 shown below. Each test substance is indicated by the corresponding substance code name shown above in Table 1.

TABLE 2

| Test substance (Code name) | Dose (mg/kg) | % Elimination |
|---|---|---|
| PF1022 (Control) | 0.5 | 50–70 |
| PF1022 (Control) | 1.0 | 60–86 |
| PF1022 (Control) | 2.0 | 100 |
| Not treated | 0 | 0 |
| PF1022-AHH (Hexahydro derivative of Example 1) | 5 | 62 |
| PF1022-ADH (Dodecahydro derivative of Example 1) | 5 | 30 |
| PF1022-BTH (Tetracyclohexylmethyl derivative of Example 1) | 5 | 30 |
| PF1022-022 (Compound of Example 3) | 5 | 84 |
| PF1022-003 (Compound of Example 4) | 10 | 76 |
| PF1022 E (Compound of Example 6) | 0.5 | 70 |
| PF1022-005 (Compound of Example 5) | 0.5 | 73 |
|  | 1.0 | 89 |
|  | 2.0 | 100 |
| PF1022-016 | 0.5 | 55 |
|  | 1.0 | 61 |
|  | 2.0 | 100 |
| PF1022-020 | 1.0 | 54 |
|  | 2.0 | 100 |
| PF1022-021 | 1.0 | 41 |
|  | 2.0 | 90 |
| PF1022-022 | 1.0 | 40 |
|  | 2.0 | 93 |
| PF1022-215 | 1.0 | 37 |
|  | 2.0 | 98 |

Test 2
In vivo Anthelmintic Activity Test on Nematodes

To each sheep which had artificially been infected with *Trichostrongylus colubriformis* (hereinafter abbreviated as "T") and *Haemonchus contortus* (hereinafter abbreviated as "T'"), respectively, a test substance weighed in a dose accurately calculated from the weight (mg) of the sheep was orally administered in the form of a gelatin capsule.

The number of parasite's eggs excreted with feces from the sheep was counted quantitatively before and after the administration so that the degree of anthelmintic effects was determined. The anthelmintic effects are evaluated by rated numeral 0, 1, 2 or 3. The anthelmintic effects are rated "0" when there were no anthelmintic activities, "2" when excretion of parasite's eggs was observed, and "3" when excretion of parasite's eggs stopped, that is, parasitic worms were removed completely.

Table 3 shows the results of the test on anthelmintic activities against the above-described two types sheep parasitic worms.

TABLE 3

| Test substance | Parasitic worms | Dose (mg/kg) | Degree of effects |
|---|---|---|---|
| PF1022 (Control) | H | 0.05 | 3 |
| PF1022 (Control) | T | 0.5 | 3 |
| PF1022-201 | H | 0.25 | 3 |
| PF1022-201 | H | 0.1 | 1 |
| PF1022-215 | H | 0.25 | 3 |
| PF1022-219 | T | 0.5 | 3 |

Test 3

Anthelmintic effects of certain PF1022 derivatives on a rat intestinal nematode were tested in accordance with the following method.

Sixteen male Wistar rats were divided into eight groups (two rats per group), and about 2,000 larval worms of *Nippostrongylus brasillensis* were hypodermically inoculated per rat. Seven days after the inoculation, PF1022, PF1022E, PF1022-002, PF1022-003, PF1022-209, PF1022-218 and PF1022-219 were, as test substances, forcedly administered p.o. to the rats in the groups, respectively, in an amount of 10 mg/kg per rat. Upon administration, each test substance (8 mg) was dissolved in 0.2 ml of dimethyl sulfoxide and then, the resultant solution was diluted with distilled water to give a 2 ml suspension. Ten days after the inoculation, the rats were each subjected to autopsy and imaginal worms parasitic on the small intestines were counted.

As the test results, the average of remaining worms in each of the eight groups and the percent effectiveness of the test substance in each group as compared with that of the infected control group are shown in Table 4. PF1022 showed percent effectiveness of 80%, but PF1022-003 and PF1022-209 showed the effectivenesses of 66.1% and 59.3%, respectively.

TABLE 4

Anthelmintic effects of each derivative on *N. brasillensis*-infected rats

| Test substance (code name) | Dose (mg/kg) | Number of remaining worms (average value ± SD) | % Effectiveness |
|---|---|---|---|
| PF 1022 (control | | 403 ± 32.5 | 80.2 |
| PF 1022E | 10 | 2175 ± 134.4 | 0 |
| PF 1022-002 | 10 | 1976.5 ± 306.2 | 2.7 |
| PF 1022-003 | 10 | 689 ± 48.1 | 66.1 |
| PF 1022-209 | 10 | 827 ± 388.9 | 59.8 |
| PF 1022-218 | 10 | 2400 ± 362.0 | 0 |
| PF 1022-219 | 10 | 2084.5 ± 94.0 | 0 |
| Control infected | 0 | 2082 ± 297.0 | — |

Examples for preparing the novel derivatives of the general formula (I) according to this invention will be described specifically by the following Examples, in which the abbreviations have the following meanings:

Bn: benzyl group

Boc: t-butoxycarbonyl group

BH: benzhydryl group (diphenylmethyl group)

Cbz: carbobenzoxy group

All: allyl group (1-propenyl group)

HP: tetrahydropyranyl group

Tr: triphenylmethyl group (trityl group)

TYR: tyrosine residue

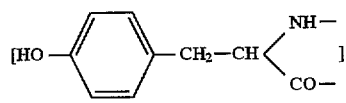

TYRA: p-hydroxyphenyllactic acid residue

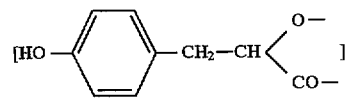

Lac: lactic acid residue

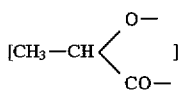

PhLac: phenyllactic acid residue

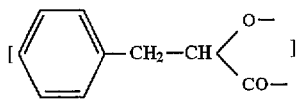

MeLeu: N-methylleucine residue

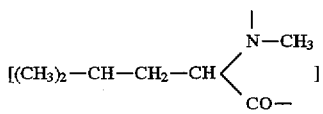

Leu: Leucine residue

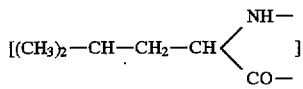

LEUA: 2-hydroxy-4-methyl-n-valeric acid residue synthesized from leucine

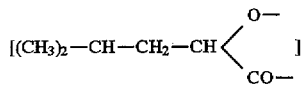

norLeu: norleucine residue

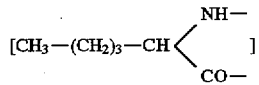

norLEAU: 2-hydroxy-L-hexanoic acid residue

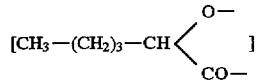

isoLEAU: 2-hydroxy-3-methyl-L-pentanoic acid residue

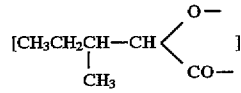

VALA: 2-hydroxyisovaleric acid residue

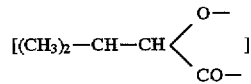

OctA: 2-hydroxyoctanoic acid residue

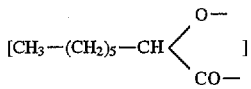

HOBt: 1-hydroxybenzotriazole
BOP-Cl: N,N-bis(2-oxo-3-oxazolidinyl)phosphinic acid chloride
DCC: dicyclohexylcarbodiimide
EDCI: 1-(3-dimethylaminopropyl)-3-ethylcarbodiimide
TFA: trifluoroacetic acid
THF: tetrahydrofuran
DMF: N,N-dimethylformamide
DMSO: dimethylsulfoxide
NMM: N-methylmorpholine
DEAD: diethyl azodicarbonate Illustrated in the following Examples 1–2 are preparation processes by hydrogenation.

EXAMPLE 1

Preparation of hydrogenation products of the PF1022 and PF1022 B substances

To 2.20 g of a mixture of the PF1022 and PF1022 B substances, 70 ml of ethanol and 30 ml of ethyl acetate were added to dissolve the former in the latter. A reaction mixture, which had been prepared by adding 1.0 g of 5% rhodium-carbon catalyst to the resulting solution, was stirred under hydrogen gas at 1 atmospheric pressure so that the mixture was subjected to catalytic reduction. Twenty two hours after the beginning of the stirring, that is, at the time when 222 ml of hydrogen had been consumed, the stirring was terminated and the catalyst was filtered off from the reaction mixture. The filtrate was concentrated under reduced pressure, whereby the residue was obtained in a colorless resin-like form. The residue was dissolved in 10 l of a hexane-ethyl acetate (1:1) mixed solvent, followed by subjecting the resulting solution to chromatography on a silica gel column packed with 1 kg of silica gel ("Silica Gel 601", product of Merck & CO.). Elution was then conducted using as eluents 0.9 l of hexane-ethyl acetate (2:1), 1.0 l of hexane-ethyl acetate (3:2) and 4.0 l of hexane-ethyl acetate (1:1), and the following four fractions were collected as eluates.

Fraction 1 (0.7 l): Partial hydrogenation products of PF1022B were contained therein;

Fraction 2 (0.9 l): Hydrogenation product of PF1022 was contained therein;

Fraction 3 (0.9 l): Partially hydrogenation products of PF1022 were contained therein; and Fraction 4 (1.5 l): A mixture of partial hydrogenation products of PF1022 and the starting material PF1022 was contained therein.

(1) Fraction 2 was concentrated under reduced pressure to obtain a colorless residue. To the residue, 10 ml of water were added, followed by stirring for 5 hours. The crystals so precipitated (448 mg) were collected by filtration.

In an NMR spectrum of this substance (in $CD_3OD$), no peak attributable to the aromatic hydrogens was observed. Further, in an EI mass spectrum, molecular ion peaks ($M^+$) at 960, 905 and a fragment peak at 864 were observed. In its UV spectrum (methanol solution), the maximum absorptions which had been observed at 263.6 nm and 257.6 nm for the PF1022 substance had disappeared. Said substance has thus been found to be dodecahydro-PF1022, that is, a compound (substance code: PF1022-ADH) of the general formula (I-i-a) where cyclohexylmethyl groups are present as $R^{2a}$ and $R^{4a}$, respectively.

Molecular formula: $C_{52}H_{88}N_4O_{12}$

Specific rotation: $[\alpha]_D$ −56.6° (c=0.15, methanol)

$^1$H-NMR spectrum (in deutero-methanol), δ (ppm): 0.84–1.08 27H(m) 1.17–2.08 38H(m) 1.42 3H(d,J=6.8) 2.87 3H(s) 2.97 3H(s) 3.07 3H(s) 3.17 3H(s) 4.81 1H(dd,J=4.1, 10.4) 5.19 1H(q,J=6.8) 5.29 1H(dd,J=4.1,11.5) 5.43–5.66 5H(m)

(2) To a colorless residue, which had been obtained by concentrating Fraction 3 under reduced pressure, 20 ml of hexane and 0.5 ml of methanol were added. The resulting mixture was allowed to stand, whereby colorless crystals precipitated. The crystals were collected by filtration in a yield of 457 mg. The substance so obtained was calculated to contain the five aromatic hydrogen atoms which are observed from its NMR spectrum (in $CD_3OD$). Further, on a UV spectrum, weakened maximum absorptions were observed at 263.6 and 257.6 nm. In an EI mass spectrum, on the other hand, the substance had molecular ion peaks at 954($M^+$), 899 and 858. The substance has been found to be hexahydro-PF1022 (substance code: PF1022-AHH), that is, a compound of the general the formula (I-i-a) where a benzyl group is present as $R^{2a}$ and a cyclohexylmethyl group as $R^{4a}$.

Molecular formula: $C_{52}H_{82}N_4O_{12}$

Specific rotation: $[\alpha]_D$ −79.6° (c=0.15, methanol)

$^1$H-NMR spectrum (in deutero-methanol), δ (ppm): 0.75–1.07 27H(m) 1.20–2.07 28H(m) 2.84, 2.89, 2.92, 2.95, 3.00, 3.07, 3.18 12H (each s, conformer) 3.05–3.22 2H(m) 4.75–4.82 1H(m) 5.14–5.32 2H(m) 5.36–5.85 5H(m) 7.25–7.34 5H(m)

(3) Fraction 1 was concentrated and the residue so obtained was dissolved in a solvent. As described above, the resulting solution was subjected to chromatography on a silica gel column, followed by elution with hexane-ethyl acetate (1:1). From eluate fractions, a hydrogenation product of the PF1022B substance was obtained. The solid so obtained was recognized to be a hydrogenation product (substance code: PF 1022-BTH) of the formula (I-i-b) in which the four benzyl groups of PF1022B substance had been reduced into four cyclohexylmethyl groups.

EXAMPLE 2

Preparation of dodecahydro-PF1022

To 500 mg of the PF1022 substance, 30 ml of ethanol and 250 mg of 5% rhodium-carbon were added, followed by catalytic reduction for two days under hydrogen gas at 1 atm. After a stop of the consumption of hydrogen was confirmed, the reaction was terminated. From the reaction mixture, the catalyst was removed using celite as a filtration assistant. The filtrate was concentrated under reduced pressure. The residue so obtained was added with water and small amounts of methanol and isopropyl ether, followed by stirring. The crystals so precipitated were collected by filtration in a yield of 499 mg.

The substance so obtained was recognized as dodecahydro PF1022 (namely, PF1022-ADH). Incidentally, as a result of thin-layer chromatography on silica gel (eluent: hexane-ethyl acetate, 1:1), no remainder of the starting substance PF1022 or hexahydro PF1022 was recognized.

Preparation of the derivatives of the general formulae (I-ii)–(I-v) by the totally synthetic process will be illustrated by the following Examples 3-4 and Examples 6–17.

EXAMPLE 3

Synthesis of cyclo-(L-MeLeu-D-Lac-)4 (code: PF1022-002)

a. Synthesis of Boc-L-MeLeu-D-Lac-OH

In 10 ml of methanol, 1.065 g (2.54 mmol) of Boc-L-MeLeu-D-Lac-OBn were dissolved, followed by the addition of 128 mg of 10% Pd—C. The resulting mixture was subjected to catalytic reduction under a hydrogen stream (for debenzylation). The reaction mixture obtained was filtered and then, the filtrate was concentrated, whereby 800 mg of the title compound were obtained (yield: 99%). The compound so obtained was fed to for use in the next reaction without purification.

b. Synthesis of H-L-MeLeu-D-Lac-OBn

In 5 ml of methylene chloride, 1.065 g (2.68 mol) of Boc-L-MeLeu-D-Lac-OBn were dissolved, followed by cooling to 50° C. To the resulting solution, 2 ml of TFA were added at the same temperature, followed by reaction at room temperature for 30 minutes (for removal of Boc). The reaction mixture obtained was concentrated and the concentrate was dissolved in 50 ml of ethyl acetate. The solution so obtained was washed with a saturated aqueous solution of sodium bicarbonate and a saturated aqueous solution of sodium chloride, followed by drying over sodium sulfate. The solvent was then distilled off from the dried solution to give 822 mg of the title compound (Yield: 100%). The compound so obtained was fed to for use in the next reaction without purification.

c. Boc-(-L-MeLeu-D-Lac-)$_2$-OBn

In 10 ml of THF, 800 mg (2.54 mmol) of the compound synthesized in procedure a) and 822 mg (2.68 mmol) of the compound synthesized in procedure b) were dissolved. To the resulting solution, 542 mg of HOBt, 0.3 ml of NMM and 0.86 g of DCC were added, followed by making condensation reaction at 4° C. for 2 days (for formation of amidobond). Insoluble matter was filtered off from the resulting reaction mixture, and the filtrate was then added with 50 ml of ethyl acetate and 30 ml of hexane. The resulting solution was washed with a 5% aqueous solution of potassium hydrogen sulfate, a saturated aqueous solution of sodium bicarbonate and a saturated aqueous solution of sodium chloride, followed by drying over sodium sulfate. After the solvent was distilled off from the dried solution, the residue was subjected to chromatography on a silica gel column (chloroform:ethyl acetate, 50:1) for making isolation and purification of the target compound. Thus, 1.20 g of the title compound were obtained (yield: 78%).

$[\alpha]_D^{21}$ : −44.7° (c=0.12, $CHCl_3$)

EI-MS m/s: 607 ($M^+$)

$^1$H-NMR($CDCl_3$) δ: 0.88(d,3H,J=6.4 Hz), 0.92(d,3H, J=6.4 Hz), 0.93(d,6H,J=6.4 Hz), 1.44 and 1.46(each s,9H), 1.51(d,3H,J=6.4 Hz), 1.53(d,3H, J=6.4 Hz), 1.40–1.84(m, 6H), 2.81,2.83,2.93 and 2.95(each s,6H), 4.74 and 4.93(dd and t,J=4,11 Hz, and J=8 Hz), 5.10 (q,1H,J=6.4 Hz), 5.12 (q,1H, J=12.2 Hz), 5.20(d,1H, J=12.2 Hz), 5.25–5.36(m, 2H), 7.30–7.39(m,5H).

d. Synthesis of Boc-(-L-MeLeu-D-Lac-)$_2$-OH

In a similar manner to the procedure a) of Example 3, 595 mg (0.98 mmol) of Boc-(-L-MeLeu-D-Lac-)$_2$-OBn were subjected to catalytic reduction for debenzylation, whereby 505 mg of the title compound were obtained (yield: 100%). The compound so obtained was fed to for use in the next reaction without purification.

e. Synthesis of H-(-L-MeLeu-D-Lac-)$_2$-OBn

In a similar manner to the procedure b) of Example 3, 634 mg (1.04 mmol) of Boc-(-L-MeLeu-D-Lac-)$_2$-OBn were subjected to the Boc-removing reaction, whereby 526 mg of the title compound were obtained (yield: 100%). The compound so obtained was provided for use in the next reaction without purification.

f. Boc-(-L-MeLeu-D-Lac-)$_4$-OBn

In 6 ml of THF, 505 mg (0.98 mmol) of the compound synthesized in the procedure d) and also 526 mg (1.04 mmol) of the compound synthesized in the procedure e) were dissolved. To the resulting solution, 204 mg of HOBt, 0.11 ml of NMM and 0.33 g of DCC were added, followed by making condensation reaction at 4° C. for 24 hours. The reaction mixture so obtained was subjected to a similar treatment to the procedure c) of Example 3, whereby 832 mg of the title compound were obtained (yield: 83%).

[α]$_D^{21}$ : −58.3° (c=0.28, CHCl$_3$)

EI-MS m/z: 1005 (M$^+$)

$^1$H-NMR(CDCl$_3$) δ: 0.86–1.03(10d,24H,J=6.4 and 6.7 Hz), 1.45 and 1.46(each s,9H), 1.38–1.58(m,16H), 1.64–1.85(m,8H), 2.83–3.11(each s, 12H), 4.45–4.56 and 4.74 (m and dd, 1H,J=4.1 and 11.1), 4.94(t,0.5H, J=8.1 Hz), 5.10(q,1H,J=7.1 Hz), 5.12(d,1H,J=12.2 Hz), 5.20(d,1H,J= 12.2 Hz), 5.13–5.40(m,5.5H), 7.30–7.39(m,5H).

g. Synthesis of cyclo-(-L-MeLeu-D-Lac-)$_4$

In a similar manner to the procedure b) of Example 3, 813 mg (0.89 mmol) of Boc-(-L-MeLeu-D-Lac-)$_4$-OBn were deprotected by reaction with TFA. The reaction mixture so obtained was post-treated similarly and the crude product so obtained was subjected to catalytic reduction and post-treatment similarly to procedure d) of Example 3.

In 200 ml of THF, the amino acid derivative, H-(L-MeLeu-D-Lac-)$_4$-OH so obtained was dissolved, followed by the addition of 0.55 g of HOBt and 0.18 ml of NMM. The resulting mixture was added to a suspension of 0.60 g of potassium chloride, 1.55 g of cesium chloride and 1.56 g of EDCl.HCl in DMF (200 ml)—THF (400 ml), followed by reaction for 5 days to effect the ring-closing reaction.

The resulting reaction mixture was added with 150 ml of ethyl acetate, followed by washing with 80 ml of water, 80 ml of a saturated aqueous solution of sodium bicarbonate, 80 ml of a 5% aqueous solution of potassium hydrogen sulfate and 80 ml of a saturated aqueous solution of sodium chloride and drying over sodium sulfate. The solvent was removed from the dried solution. The residue was subjected to chromatography on a silica gel column (chloroform:ethyl acetate=5:1→1:1) for the isolation and purification of the target compound, whereby 559 mg of the title compound were obtained (yield: 86%).

[α]$_D^{21}$ : −68.2° (c=0.15, methanol)

m.p. 168°–170° C.

FAB-MS m/z: 797(M$^+$)

$^1$H-NMR(CDCl$_3$) δ: 0.85 and 0.95(each d, 6H,J=6.6 Hz), 0.89 and 0.98(each d, 6H, J=6.8 Hz), 0.91 and 0.98(each d, 6H, J=6.8 Hz), 1.01 and 1.07(each d, 6H,J=6.6 Hz), 0.99(d, 3H,J=6.8 Hz), 1.36–1.51(m, 3H,J=6.4 Hz), 1.55–1.65(m, 1H), 1.42(d,3H,J=6.8 Hz), 1.44(d,3H,J=6.8), 1.45(d,3H,J= 6.8 Hz), 1.67–1.99(m,8H), 2.85(s,3H), 2.96(s,3H), 3.07(s, 3H), 3.16(s,3H), 4.78(dd,1H,J=4.3 and 11.1 Hz), 5.19(q,1H, J=6.8 Hz), 5.29(dd,1H,J=5.6 and 10.4 Hz), 5.44(dd,1H,J= 5.4 and 11.1 Hz), 5.48(dd,1H,J=5.8 and 10.0 Hz), 5.58(q, 1H,J=6.8 Hz), 5.64(q,1H,J=6.8 Hz), 5.69(q,1H, J=6.8 Hz)

EXAMPLE 4

Synthesis of cyclo-(-L-MeLeu-D-Lac-L-MeLeu-D-PhLac-L-MeLeu-D-Lac-L-MeLeu-D-LEUA-)
(Code: PF1022-003)

a. Synthesis of Boc-L-MeLeu-D-PhLac-L-MeLeu-D-Lac-OBn

In 15 ml of THF, 1.85 g (3 mmol) of Boc-L-MeLeu-D-PhLac-OH synthesized in a similar manner to the procedure a) of Example 3 and also 1.016 g (3.3 mmol) of H-L-MeLeu-D-Lac-OBn synthesized in the procedure b) of Example 3 were dissolved, followed by the addition of 1.5 ml of pyridine, 535 mg (3.6 mmol) of HOBt and 817 mg (3.6 mmol) of DCC under ice cooling. The resulting mixture was reacted for 15 hours, whereby the reactants were condensed by an amide-bond. Insoluble matter was removed from the reaction mixture, followed by post-treatment as in the procedure c) of Example 3. Subsequent to the removal of the solvent from the solution, the residue obtained was subjected to chromatography on a silica gel column (toluene:ethyl acetate 10:1→5:1) for isolation and purification, whereby 1.37 g of the title compound were obtained (yield: 67%). The compound so obtained was fed to for use in the next reaction without further purification.

b. Synthesis of H-L-MeLeu-D-PhLac-L-MeLeu-D-Lac-OBn

In a similar manner to the procedure e) of Example 3, 1.15 g of the title compound were obtained (yield: 98%) from 1.37 g (2 mmol) of the protected compound obtained above in the procedure a). The compound was fed to for use in the next reaction without further purification.

c. Synthesis of Boc-L-MeLeu-D-Lac-L-MeLeu-D-PhLac-L-MeLeu-D-Lac-OBn

In a similar manner to the procedure a) of Example 4, 1.15 g (1.97 mmol) of H-L-MeLeu-D-PhLac-L-MeLeu-D-Lac-OBn synthesized in the procedure b) of Example 4 and 720 mg (1.97 mmol) of Boc-L-MeLeu-D-Lac-OH synthesized in the procedure a) of Example 3 were condensed with each other by the amide-bond, whereby 1.30 g of the title compound were obtained (yield: 75%). The compound was fed to for use in the next reaction without further purification.

d. Synthesis of H-L-MeLeu-D-Lac-L-MeLeu-D-PhLac-L-MeLeu-D-Lac-OBn

In a similar manner to the procedure e) of Example 3, 1.30 g (1.47 mmol) of the protected compound obtained above in procedure c) were treated for removal of Boc therefrom, whereby 1.28 g of the title compound were obtained. The compound was fed to for use in the next reaction without further purification.

e. Synthesis of Boc-L-MeLeu-D-LEUA-L-MeLeu-D-Lac-L-MeLeu-D-PhLac-L-MeLeu-D-Lac-OBn In a similar manner to the procedure a) of Example 4, 1.28 g (1.47 mmol) of the crude product, H-L-MeLeu-D-Lac-L-MeLeu-D-PhLac-L-MeLeu-D-Lac-OBn synthesized above in the procedure d) of Example 4 and 590 mg (1.64 mmol) of Boc-L-MeLeu-D-LEUA-OH synthesized similarly to the procedure b) of Example 3 were condensed with each other, whereby 1.2 g of the title compound were obtained (yield: 73%). The compound was fed to for use in the next reaction without further purification.

f. Synthesis of cyclo-(-L-MeLeu-D-Lac-L-MeLeu-D-PhLac-L-MeLeu-D-Lac-L-MeLeu-D-LEUA-)

In a similar manner to the procedure g) of Example 3, 1.2 g (1.07 mmol) of the compound synthesized in the procedure e) of Example 4 were subjected to the deprotection and ring-closing reaction, whereby 433 mg of the title compound were obtained (yield: 44%).

[α]$_D^{21}$ : −66.2° (c=0.15, methanol)

FAB-MS m/s: 915(M$^+$)

$^1$H-NMR(CD$_3$OD) δ: 0.81 and 0.85(each d,6H,J=6.4 Hz), 0.86 and 0.95(each d,6H,J=6.6 Hz), 0.89 and 0.98(each d,6H,J=6.8 Hz), 0.91 and 0.98(each d,6H,J=6.8 Hz), 1.01 and 1.07(each d,6H,J=6.6 Hz), 0.99(d,3H, J=6.8 Hz), 1.36–1.65(m,6H), 1.44(d,3H,J=6.8 Hz), 1.45(d,3H,J=6.8 Hz), 1.67–99(m,8H), 2.85(s,3H), 2.96(s,3H), 3.07(s,2H), 3.16(s,3H), 4.78(dd,1H,J=4.3 and 11.1 Hz), 5.19(q,1H,J=6.8

Hz), 5.29(dd,1H,J=5.6 and 10.4 Hz), 5.44(dd,1H,J=5.4 and 11.1 Hz), 5.48(dd, 1H,J=5.8 and 10.0 Hz), 5.58(q,1H,J=6.8 Hz), 5.64(q, 1H,J=6.8 Hz), 5.69(q,1H,J=6.8 Hz), 7.23–7.34 (5H,m).

EXAMPLE 5

Synthesis of cyclo-(-L-MeLeu-D-Lac-L-MeLeu-D-PhLac-L-MeLeu-D-Lac-L-MeLeu-D-TYRA(OMe) (Code: PF1022-005)

In 3 ml of THF, 99.2 mg (0.103 mmol) of PF1022 E substance, which can also be expressed as "cyclo-(-L-MeLeu-D-Lac-L-MeLeu-D-PhLac-L-MeLeu-D-Lac-L-MeLeu-D-TYRA)", were dissolved, followed by ice cooling. Under a nitrogen stream, the resulting solution was added with 0.02 ml (0.32 mmol) of methyl iodide and 9 mg (60% in oil, 0.23 mmol) of sodium hydride were added, followed by reaction for 40 minutes (for O-methylation). The reaction mixture obtained was added with 20 ml of ethyl acetate, followed by washing with 10 ml of a saturated aqueous solution of sodium chloride and drying over magnesium sulfate. After removal of the solvent from the solution, the residue obtained was subjected to preparative TLC (chloroform:ethyl acetate=3:1) for making isolation and purification, whereby 88.4 mg of the title compound were obtained (yield: 88%).

$[\alpha]_D^{21}$ : −104° (c=0.13, methanol)

m.p. 103°–105° C. (recrystallized from MeOH-H$_2$O-AcOEt)

FAB-MS m/z: 979(M$^+$)

$^1$H-NMR(CD$_3$OD) δ: 0.78–1.05(each d,27H,J=6.4–7.0 Hz), 1.38(d,3H,J=7.0 Hz), 1.3–1.5(m,4H), 1.5–1.9(m,8H), 2.81(s,3H), 2.88(s,3H), 2.90(s,3H), 2.99(s,3H), 3.08(dd,1H, J=8.0 and 13.2 Hz), 3.09(dd,1H,J=7.8 and 13.2 Hz), 3.17 (dd,1H,J=7.3 and 13.2 Hz), 3.18(dd,1H, J=7.2 and 13.2 Hz), 3.30(s,3H), 4.78(dd,1H,J=4.3 and 11.1 Hz), 5.19(q,1H,J=6.8 Hz), 5.29(dd,1H,J=5.6 and 10.4 Hz), 5.44(dd,1H,J=5.4 and 11.1 Hz), 5.48(dd,1H, J=5.8 and 10.0 Hz), 5.58(q,1H,J=6.8 Hz), 5.64(q,1H, J=6.8 Hz), 5.69(q,1H,J=6.8 Hz), 6.80(d,2H, J=8.3 Hz), 7.20(d,2H, J=8.3 Hz), 7.24–7.34(5H,m).

EXAMPLE 6

Synthesis of the PF1022 E substance, that is, PF1022 E which may also be expressed as "cyclo-(-L-Meleu-D-Lac-L-MeLeu-D-TYRA-L-MeLeu-D-Lac-L-MeLeu-D-PhLac)"

a. Boc-L-MeLeu-D-Lac-L-MeLeu-D-TYRA(OBn)-L-MeLeu-D-Lac-L-MeLeu-D-PhLac-OBn

In 14 ml of THF were dissolved 1.40 g of Boc-L-Meleu-D-Lac-L-Meleu-D-TYRA(OBn)-OH, 1.16 g of H-L-Meleu-D-Lac-L-Meleu-D-PhLac-OBn and 247 mg of HOBT. The resulting solution was added with 410 mg of DCC under ice cooling, followed by stirring overnight at room temperature (for the condensation reaction). After the precipitate so obtained was removed by filtration, the filtrate was concentrated. The residue was added with 50 ml of ethyl acetate. The resulting mixture was washed successively with a 5% solution of sodium sulfite, a saturated aqueous solution of sodium bicarbonate and a saturated aqueous solution of sodium chloride and then dried over anhydrous magnesium sulfate, followed by filtration. The filtrate was concentrated and the residue was separated and purified by chromatography on a silica gel column (toluene:ethyl acetate=5:1), whereby 1.16 g of the title compound were obtained as a colorless oil (yield: 46.0%).

b. H-L-MeLeu-D-Lac-L-MeLeu-D-TYRA(OBn)-L-MeLeu-D-Lac-L-MeLeu-D-PhLac-OBn

In 11 ml of dichloromethane were dissolved Boc-L-MeLeu-D-Lac-L-MeLeu-D-TYRA(OBn)-L-MeLeu-D-Lac-L-MeLeu-D-PhLac-OBn (1.10 g). The resulting solution was added with 4 ml of TFA under ice cooling, followed by stirring at room temperature for one hour. The reaction mixture obtained was added with a small quantity of toluene and was then concentrated. Ethyl acetate (50 ml) was added to the concentrate, followed by washing successively with a saturated aqueous solution of sodium bicarbonate and water and drying over anhydrous magnesium sulfate. After filtration, the filtrate was concentrated and the residue was fed to as such, for use in the next reaction.

c. H-L-MeLeu-D-Lac-L-MeLeu-D-TYRA-L-MeLeu-D-Lac-L-MeLeu-D-PhLac-OH

In a mixed solution of 10 ml of methanol and 1 ml of water, 1.05 g of H-L-MeLeu-D-Lac-L-MeLeu-D-TYRA (OBn)-L-MeLeu-D-Lac-L-MeLeu-D-PhLac-OBn were dissolved. In a nitrogen atmosphere, the resulting solution was added with 100 mg of 10% Pd—C, followed by catalytic hydrogenation with hydrogen at room temperature under normal pressure for 5 hours. The catalyst was filtered off with using Hyflo Super Cel, and the filtrate was concentrated. The residue was fed to as such for use in the next reaction.

d. Cyclo-(-L-MeLeu-D-Lac-L-MeLeu-D-TYRA-L-MeLeu-D-Lac-L-MeLeu-D-PhLac) (namely, PF1022 E substance)

In a liquid mixture of 800 mg of THF and 240 ml of DMF, 477 mg of lithium chloride, 840 mg of potassium chloride, 610 mg of sodium chloride, 1.75 g of cesium chloride and 4.1 g of EDCI.HCL were added. To the resulting mixture, a solution of 1.01 g of H-L-MeLeu-D-Lac-L-MeLeu-D-TYRA-L-MeLeu-D-Lac-L-MeLeu-D-PhLac-OH, 720 mg of HOBt and 0.24 ml of NMM in 120 ml of THF was added, followed by stirring overnight. After the solvents were distilled off, 450 ml of ethyl acetate and 220 ml of water were added to the resulting residue. The resulting mixture was allowed to separate into two layers. The organic layer so obtained was washed successively with a saturated aqueous solution of sodium bicarbonate, a 5% solution of sodium sulfite and a saturated aqueous solution of sodium chloride, followed by drying over anhydrous magnesium sulfate and filtering the organic solution.

The filtrate was then concentrated. The residue so obtained was purified by chromatography on a silica gel column (chloroform:ethyl acetate=3:1) and then by reversed phase chromatography on a silylized silica,gel column (CH$_3$CN—H$_2$O=85:15), whereby 324 mg of the title compound were obtained as white powder (yield: 33%).

$[\alpha]_D^{25}$ : −100° (c=1.0, MeOH)

$^1$H-NMR(CD$_3$OD) δ: 0.78–1.00(m,24H,δ-Me(MeLeu)), 1.04, 1.05,1.38,1.39(each d, total 6H, β-Me(Lac)), 1.28–1.90(m,12H,β-CH$_2$,τ-H(MeLeu)), 2.82–3.00(m,12H, NMe), 2.93–3.20(m,4H,β-CH$_2$, (TYRA, PhLac)),4.76–5.81 (m,8H,α-H), each 2H, J=8.4, aromatic(TYRA)), 7.24

MS(EI): M$^+$=964

EXAMPLE 7

Synthesis of cyclo-(L-MeLeu-D-Lac-L-MeLeu-D-TYRA(OBn))$_2$ (code: PF1022-201)

a. Synthesis of O-benzyloxy-L-phenyllactic acid (H-L-TYRA(OBn)-OH, namely

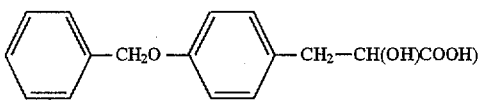

In a mixed solution of 75 ml of 1,4-dioxane and 50 ml of water, 5.46 g of O-benzyl-L-tyrosine (H-L-TYR(OBn)-OH) were suspended. To the resulting suspension, 25 ml of 2.4N hydrochloric acid were added under ice cooling to dissolve the latter in the former. The resulting solution was added with an aqueous solution of 4.14 g of sodium nitrite, and then with 75 ml of 1,4-dioxane, 15 ml of water and 10 ml of 2N aqueous hydrochloric acid, followed by reaction for 30 minutes (for diazotization of the amino group of tyrosine). The reaction mixture obtained was added with an aqueous solution of 1.38 g of sodium nitrite and 10 ml of 2N hydrochloric acid, followed by reaction at room temperature for 2 hours (for conversion of the diazo group into a hydroxyl group).

The resulting reaction mixture was added with 200 ml of ethyl acetate. The resulting mixture was allowed to separate into two layers. The water layer so obtained was extracted again with ethyl acetate. The ethyl acetate extract was combined with the organic layer, followed by washing twice with 50 ml portions of a 30% aqueous solution of sodium chloride, drying over anhydrous magnesium sulfate and then concentrating under reduced pressure, whereby 1.33 g of the title compound were obtained (yield: 24.3%).

$^1$H-NMR(DMSO-d$_6$) δ=2.78(ddd,2H,J=0,4,0.8,1.4,4.4,β-CH$_2$), 4.08(q,1H,J=0.4,0.8,α-H), 5.06(s,2H,C$\underline{H}_2$Ph), 7.01 (d×2,4H,J=0.8,C$_6$H$_4$), 7.41(m,5H,Ph)

b. Synthesis of H-L-TYRA(OBn)-OK (potassium O-benzyl-L-phenyllactate)

In a mixed solution of 5.5 ml of methanol and 7.65 ml of chloroform, 1.10 g of H-L-TYRA(OBn)-OH were dissolved under heating, followed by the addition of a solution (1 g/10 ml) of potassium 2-ethylhexanoate in ethyl acetate. When a precipitate started to appear, 15 ml of ethyl acetate were added further to the resulting solution, followed by stirring for 17 hours. The precipitate so obtained was collected by filtration, followed by washing with ethyl acetate and drying under reduced pressure, whereby 950 mg of the title compound were obtained (yield: 76.6%).

c: H-L-TYRA(OBn)-O-All (allyl O-benzyl-L-phenyllactate)

In 15 ml of DMF, 2.5 g of H-L-TYRA(OBn)-OK and 0.34 g of sodium bicarbonate were dissolved under ice cooling. To the resulting solution, 0.91 ml of allyl iodide was added and they were reacted at the same temperature for 12 hours. The reaction mixture was added with 75 ml of ethyl acetate, followed by washing once with 50 ml of water and twice with 50 ml portions of a 30% aqueous solution of sodium chloride, drying over anhydrous magnesium sulfate and then concentrating. The residue so obtained was purified by chromatography on a silica gel column (toluene:ethyl acetate=6:1), whereby 2.15 g of the title compound were obtained (yield: 86.0%).

$^1$H-NMR(CDCl$_3$): δ=3.00(ddd,2H,J=0.5,0.7,1.4,4.1,β-CH$_2$), 4.43(q,1H,J=0.4,0.7,α-H), 4.64(m,2H,CH$_2$(allyl)), 5.03(s,2H,C$\underline{H}_2$Ph), 5.32(m,2H,CH$_2$(Allyl)), 5.90(m,1H,CH(allyl)), 7.02(d×2,4H,J=0.9,C$_6$H$_4$), 7.37(m,5H,Ph)

d. Synthesis of Boc-L-MeLeu-D-TYRA(OBn)-O-All

In 8 ml of THF, 1.71 g of Boc-L-MeLeu-OH and 1.75 g of triphenylphosphine were dissolved. The resulting solution was added dropwise with a solution of 2.08 g of H-L-TYRA(OBn)-O-All and 1.09 ml of DEAD in 4 ml of THF under ice cooling, followed by reaction at the same temperature for 16 hours (for making condensation via an ester-bond). The reaction mixture obtained was concentrated and the residue was purified by chromatography on a silica gel column (toluene:ethyl acetate=20:1), whereby 3.51 g of the title compound were obtained (yield: 98.0%).

$^1$H-NMR(CDCl$_3$): δ=0.91(s×2,6H,δ-CH$_3$(Me-Leu)), 1.47 (s×2,9H,CH$_3$(Boc)), 1.38–1.64(m,3H,β-CH$_2$,γ-H(MeLeu), 2.72(d,3H,J=1.24,N—CH$_3$), 3.10(m,2H,β-CH$_2$(TYRA)), 4.59(m,2H,CH$_2$(allyl)), 4.7–5.0(m,1H,α-H(MeLeu)), 5.03 (s,2H,C$\underline{H}_2$Ph), 5.17–5.32(m,3H,α-H(TYRA), CH$_2$(allyl)), 5.83(m,1H,CH(allyl)), 7.02(d×2,4H,J=0.8,C$_6$H$_4$), 7.36(m, 5H,Ph)

e. Synthesis of H-L-MeLeu-D-TYRA(OBn)-O-All

In 15 ml of TFA, 3.49 g of Boc-L-MeLeu-D-TYRA(OBn)-O-All were dissolved, followed by reaction at 20° C. for 20 minutes (for removal of Boc). The resultant reaction solution was concentrated. Toluene was add to the concentrate, and TFA was removed azeotropically. The residue was dissolved in 50 ml of ethyl acetate. The resulting solution was washed successively with a 7% aqueous solution of sodium bicarbonate, water and a 30% aqueous solution of sodium chloride, each, in an amount of 50 ml, dried over anhydrous magnesium sulfate and concentrated under reduced pressure, whereby 2.68 g of the title compound were obtained (94.4%). The product so obtained was fed to as such for use in the next reaction.

f. Synthesis of Boc-L-MeLeu-D-Lac-L-MeLeu-D-TYRA(OBn)-O-All

In a mixed solution of 20 ml of THF and 2 ml of pyridine, 1.98 g of H-L-MeLeu-D-TYRA(OBn)-O-All and 2.47 g of Boc-L-MeLeu-D-Lac-OH were dissolved. The resulting solution was added with 0.96 g of HOBt and 1.13 g of DCC under ice cooling, followed by stirring at the same temperature for 16.5 hours. After the precipitate was filtered off, the filtrate was con centrated. The residue so obtained was purified by chromatography on a silica gel column (toluene:ethyl acetate=6:1), whereby 2.58 g of the title compound were obtained (yield: 77.4%).

g. Synthesis of H-L-MeLeu-D-Lac-L-MeLeu-D-TYRA(OBn)-O-All

In 6.5 ml of methylene chloride, 1.29 g of Boc-L-MeLeu-D-Lac-L-MeLeu-D-TYRA(OBn)-O-All were dissolved. TFA (6.45 ml) was added dropwise to the resulting solution under ice cooling, followed by stirring for 20 minutes. The reaction mixture was concentrated under reduced pressure. Toluene was added to the concentrate, and TFA was removed azeotropically. The residue was dissolved in ethyl acetate. The resulting solution was washed successively with a 7% aqueous solution of sodium bicarbonate, water and a 30% aqueous solution of sodium chloride, dried over anhydrous magnesium sulfate and then, concentrated, whereby 1.05 g of the title compound were obtained (yield: 94.0%). The product was fed to as such for use in the next reaction h. Synthesis of Boc-L-MeLeu-D-Lac-L-MeLeu-D-TYRA(OBn)-OH In 6.5 ml of methylene chloride, 1.29 g of Boc-L-MeLeu-D-Lac-L-MeLeu-D-TYRA(OBn)-O-All were dissolved, followed by the addition of 44 mg of triphenylphosphine. To the resulting solution, 8.7 mg of tetrakis (triphenylphosphine)palladium were added in a nitrogen atmosphere to dissolve the latter in the former. The resulting solution was added with 0.87 ml of 2N potassium 2-ethylhexanoate, followed by stirring for 5 minutes. The reaction mixture was concentrated and the residue was dissolved in ethyl acetate. The resulting solution was acidified with hydrochloric acid. The acidified solution was washed successively with water and a 30% aqueous solution of sodium chloride, dried over anhydrous sodium sulfate and then concentrated, whereby the title compound were obtained. The product so obtained was fed to as such, for use in the next reaction.

i. Synthesis of Boc-(L-MeLeu-D-Lac-L-MeLeu-D-TYRA (OBn))$_2$-O-All

In 16 ml of tetrahydrofuran, 1.51 g of Boc-L-MeLeu-D-Lac-L-MeLeu-D-TYRA(OBn)-OH, 1.04 g of H-L-MeLeu-D-Lac-L-MeLeu-D-TYR(OBn)-O-All, 260 mg of HOBt and 0.27 ml of triethylamine were dissolved. The resulting solution was added with 428 mg of DCC under ice cooling, followed by stirring for 13 hours (for making condensation). The precipitate obtained was filtered off and the filtrate was then concentrated. The residue was dissolved in ethyl acetate. The resulting solution was washed successively with 5% potassium bisulfate, a 7% aqueous solution of sodium bicarbonate and a 20% aqueous solution of sodium chloride, dried over anhydrous magnesium sulfate and then concentrated under reduced pressure. The residue was purified by chromatography on a silica gel column (toluene:ethyl acetate=4:1), whereby 950 mg of the title compound were obtained (yield: 44.4%).

j. Synthesis of Boc-(L-MeLeu-D-Lac-L-MeLeu-D-TYRA (OBn))$_2$-O-BH

In 4.75 ml of methylene chloride, 950 mg of Boc-(L-MeLeu-D-Lac-L-Me Leu-D-TYRA(OBn))$_2$-O-All were dissolved. The resulting solution was added with 18 mg of triphenylphosphine, followed by the addition of 4 mg of tetrakis(triphenylphosphine)palladium in a nitrogen atmosphere. After they were dissolved completely, 0.36 ml of 2N potassium 2-ethylhexanoate was added to the resulting solution, followed by stirring for 5 minutes.

The reaction mixture obtained was acidified with 2N hydrochloric acid, followed by washing successively with water and a 30% aqueous solution of sodium chloride and drying over anhydrous sodium sulfate. Subsequent to the removal of the anhydrous sodium sulfate by filtration, a solution of 196 mg of diphenyldiazomethane in ethyl acetate was added to the resulting filtrate. The resulting mixture was concentrated and the residue was purified by chromatography on a silica gel column (benzene:ethyl acetate=5:1), whereby 1.08 g of the title compound were obtained (yield: 100%).

k. Synthesis of H-(L-MeLeu-D-Lac-L-MeLeu-D-TYRA (OBn))$_2$-OH

In 5.4 ml of methylene chloride, 900 mg of Boc-(L-MeLeu-D-Lac-L-MeLeu-D-TYRA(OBn))$_2$-O-BH were dissolved. The resulting solution was added dropwise with 2.7 ml of TFA under ice cooling, followed by reaction at the same temperature for 1.5 hours. The reaction mixture was concentrated under reduced pressure. Toluene was added to the concentrate and TFA was removed azeotropically, whereby 1.12 g of the title compound were obtained. The compound so obtained was fed to as such for use in the next reaction.

l. Synthesis of cyclo-(L-MeLeu-D-Lac-L-MeLeu-D-TYRA (OBn))$_2$ (code: PF1022-201)

To a mixture of 263 mg of lithium chloride, 362 mg of sodium chloride, 463 mg of potassium chloride, 1.04 g of cesium chloride, 1.19 g of ED-CI.HCl, 650 ml of THF and 190 ml of DMF, there was added a solution of 734 mg of H-(L-MeLeu-D-Lac-L-MeLeu-D-TYRA(OBn))$_2$-OH, 419 mg of HOBt and 0.2 ml of NMM in 100 ml of THF. The resulting mixture was stirred at room temperature for 36 hours.

The reaction mixture was concentrated. The residue was then dissolved in 200 ml of ethyl acetate. The resulting solution was washed successively with water, a 7% aqueous solution of sodium bicarbonate, a 5% aqueous solution of potassium hydrogen sulfate and a 30% aqueous solution of sodium chloride, each in 200 ml-portions, dried over anhydrous sodium sulfate and then concentrated under reduced pressure. The residue so obtained was purified by chromatography on a silica gel column (chloroform:ethyl acetate= 3:1), whereby 436 mg of the title compound were obtained (yield: 60.5%).

$[\alpha]_D^{20}$ : −84.5° (c=1.0, Methanol)

$^1$H-NMR(CD$_3$OD) δ: 0.82–1.05(m,27H,δ-CH$_3$(MeLeu), β-CH$_3$(Lac)), 1.38(d,3H,J=0.7,β-CH$_3$(Lac)), 1.40–1.90(m, 12H,β-CH$_2$,γ-H(MeLeu)), 2.82,2.86,2.91, 2.99(each s,12H, N—CH$_3$), 2.90–3.20(m,4H,β-CH$_2$(TYRA)), 5.05(s,4H,C H$_2$Ph), 4.70–5.82(m,8H,α-H(MeLeu,TYRA, Lac)), 7.08(d× 2,8H,J=0.9,C$_6$H$_4$), 7.35(m,10H,Ph)

EXAMPLE 8

Synthesis of cyclo-(L-MeLeu-D-Lac-L-MeLeu-D-TYRA)$_2$ (code: PF1022-202)

In 3 ml of methanol, 271 mg of cyclo-(L-MeLeu-D-Lac-L-MeLeu-D-TYRA(OBn))$_2$ were dissolved. To the resulting solution, 27 mg of 10% Pd/C were added to conduct catalytic hydrogenation. About 30 minutes after the initiation of the catalytic hydrogenation, a white precipitate appeared. The precipitate so formed were dissolved in 0.75ml of THF and a small quantity of acetic acid as added thereto. The resulting solution was again subjected to the hydrogenation for 22 hours. The reaction mixture was added with 27 mg of 10% Pd/C and the hydrogenation was continued for further 30 hours. After the removal of the catalyst by filtration, the filtrate was concentrated under reduced pressure. The residue was purified by chromatography on a silica gel column (chloroform:ethyl acetate= 2:1→1:1), whereby 142 mg of the title compound were obtained as white powder (yield: 63.0%).

$[\alpha]_D^{20}$ : −110° (c=0.1, Methanol)

$^1$H-NMR(CD$_3$OD): δ=0.83–1.06(m,27H,δ-CH$_3$(MeLeu), β-CH$_3$(Lac)), 1.38(d,3H,J=0.6,β-CH$_3$(Lac)), 1.39–1.95(m, 12H,β-CH$_2$,γ-H(MeLeu)), 2.82,2.86,2.92, 2.99(each s,12H, N—CH$_3$), 2.70–3.15(m,4H,β-CH$_2$(TYRA)), 4.70–5.80(m, 8H,α-H(MeLeu,TYRA,Lac)), 6.91(d×2,8H, J=0.9,C$_6$H$_4$)

EXAMPLE 9

Synthesis of cyclo(L-MeLeu-D-VALA-L-MeLeu-D-PhLac)$_2$ (code: PF1022-203)

a. L-2-Hydroxyisovaleric acid

To a liquid mixture of 170 ml of water, 170 ml of acetic acid and 40 ml of 1,4-dioxane, were added 23.4 g (0.2 mol) of L-valine, followed by heating to 40° C. to dissolve the valine in, said liquid. To the resulting solution, a solution of 41.4 g of sodium nitrite in 50 ml of water was added dropwise. The resultant mixture was stirred and reacted at room temperature for 3 hours. Under ice cooling, the reaction mixture obtained was added to a liquid mixture of 300 ml of a saturated aqueous solution of sodium chloride and 750 ml of ethyl acetate. The resulting mixture was allowed to separate into two layers. The water layer so obtained was extracted four times with 100 ml-portions of ethyl acetate. The combined organic layers were dried over anhydrous magnesium sulfate. The magnesium sulfate was filtered off and the filtrate was concentrated under reduced pressure, whereby the title compound was obtained.

b. Diphenylmethyl L-2-hydroxyisovalerate (H-L-VALA-O-BH)

Ethyl acetate (300 ml) was added to the compound obtained in the procedure a) to dissolve the latter in the former. To the resulting solution, a solution of diphenyldiazomethane in ethyl acetate (38.8 g/400 ml) was added dropwise, followed by stirring overnight at room temperature. Acetic acid (30 ml) was added to the reaction mixture, followed by washing thrice with 300-ml portions of a saturated aqueous solution of sodium bicarbonate. The organic layer was dried over anhydrous magnesium sulfate, followed by filtration. The filtrate was concentrated under reduced pressure and the residue so obtained was then purified by chromatography on a silica gel column (toluene:ethyl acetate=20:1), whereby 28.3 g of the title compound were obtained as an oil (yield: 49.7%).

1H-NMR(CD$_3$OD): δ=0.76(d,3H,J=7.0,Me), 1.02(d,3H, J=7.0,Me), 2.67(d,J=6.2,OH), 6.96(s,1H,C$\underline{H}$Ph$_2$), 7.25–7.40 (m,10H,Ph)

c. Diphenylmethyl L-2-(p-tosyloxy)isovalerate

In 270 ml of dichloromethane, 26.8 g (94 mmol) of the compound obtained in the procedure b) were dissolved. To the resulting solution, 57.2 g of tosyl chloride and 32.4 ml of pyridine were added, followed by stirring overnight at room temperature. Dichloromethane and water (each 250 ml) were added to the reaction mixture. The resulting mixture was allowed to separate into two layers. The organic layer was washed successively with a 2% aqueous solution of sodium bicarbonate, 200 ml of water and 200 ml of water and then dried over anhydrous magnesium sulfate. The magnesium sulfate was removed from the organic layer by filtration. The filtrate was concentrated under reduced pressure, and the residue was then purified by chromatography on a silica gel column (toluene:ethyl acetate=10:1), whereby 29.5 g of the title compound were obtained as pale yellow crystals (yield: 69.9%).

$^1$H-NMR(CDCl$_3$): δ=2.37(s,3H,CH$_3$C$_6$H$_4$SO$_2$), 6.79(s, 1H, C$\underline{H}$Ph$_2$), 7.18(d,2H,J=8.4,C$\underline{H}_3$C$_6$H$_4$So$_2$), 7.22–7.35 (m,10H,Ph), 7.70(d,2H,J=8.4,CH$_3$C$_6\underline{H}_4$SO$_2$)

d. Boc-L-MeLeu-D-VALA-OBH

In 20 ml of DMSO, 4.90 g (20 mmol) of Boc-L-MeLeu-OH and 13.2 g of the compound (tosylate) obtained above in the procedure c) were dissolved under heating at 50° C., followed by the gradual addition of 5.52 g of potassium carbonate. The resulting mixture was stirred and reacted at 50° C. for 4.5 hours (for esterification). To the reaction mixture, ethyl acetate and water (each 50 ml) were added. The resulting mixture was allowed to separate into two layers. The water layer so obtained was extracted again with 50 ml of ethyl acetate. The combined organic layers (the extracts) were washed with a 10% aqueous solution of sodium chloride and then dried over anhydrous magnesium sulfate. After filtration, the filtrate was concentrated and the residue obtained was then purified by chromatography on a silica gel column (chloroform:ethyl acetate=50:1), whereby 3.75 g of the title compound were obtained as pale yellow crystals (yield: 36.6%).

[α]$_D$ : −57.1° (c=0.15, CHCl$_3$)

$^1$H-NMR(CDCl$_3$): δ=1.46(s,9H,t-Bu), 2.72(d,3H,NMe), 6.91(s,1H,C$\underline{H}$Ph$_2$), 7.26–7.34(m,10H,Ph)

e. Boc-L-MeLeu-D-VALA-OH

In a liquid mixture of 30 ml of methanol and 3 ml of water, 3.0 g (5.86 mmol) of the compound obtained above in the procedure d) were dissolved. The resulting solution was added with 300 mg of 10% Pd—C in a nitrogen atmosphere, followed by catalytic hydrogenation with hydrogen gas at room temperature under 1 atom., for 5 hours (for removal of benzhydryl group, BH). The catalyst was filtered off with aid of Hgflo Super Cel and the filtrate was concentrated. The concentrate was fed to as such for use in the next reaction.

f. H-L-MeLeu-D-PhLac-OBn

In 5 ml of dichloromethane, 4.51 g (9.33 mmol) of Boc-L-MeLeu-D-PhLac-OBn were dissolved. The resulting solution was added with 4 ml of TFA under ice cooling, followed by stirring at room temperature for 3 hours. The reaction mixture was added with a small quantity of toluene and concentrated. Ethyl acetate (75 ml) was then added to the concentrate. The resulting mixture was washed with a saturated aqueous solution of sodium bicarbonate and water, dried over anhydrous magnesium sulfate and then filtered. The filtrate was concentrated and the residue was fed as such for use in the next reaction.

g. Boc-L-MeLeu-D-VALA-L-MeLeu-D-PhLac-OBn

In a liquid mixture of 30 ml of THF and 3 ml of pyridine, 2.8 g of Boc-L-MeLeu-D-VALA-OH, 2.47 g of H-L-MeLeu-D-PhLac-OBn and 950 mg of HOBt were dissolved. The resulting solution was added with 1.452 g of DCC under ice cooling, followed by stirring overnight at room temperature. The precipitate was removed from the reaction mixture by filtration and the filtrate was concentrated. Ethyl acetate (280 ml) was then added to the residue. The resulting mixture was washed successively with 140 ml of a 5% solution of sodium sulfite, 140 ml of a saturated aqueous solution of sodium bicarbonate and 140 ml of a saturated aqueous solution of sodium chloride, dried over anhydrous magnesium sulfate and then filtered. The filtrate was concentrated. The concentrate obtained was then purified by chromatography on a silica gel column (toluene→toluene:ethyl acetate=10:1), whereby 3.20 g of the title compound were obtained as a colorless oil (yield: 74.2%).

[α]$_D$ : −38.5° (c=0.5, CHCl$_3$)

$^1$H-NMR(CDCl$_3$): δ=0.82–1.08(m,18H,δ-Me(MeLeu),γ-Me(VALA)), 1.43,1.45(each s,9H,t-Bu), 2.85,2.86(each s,each 3H,NMe), 7.16–7.36(m,10H,Ph)

h. H-L-MeLeu-D-VALA-L-MeLeu-D-PhLac-OBn

In 2 ml of dichloromethane, 1.1 g (1.74 mmol) of Boc-L-MeLeu-D-VALA-L-MeLeu-D-PhLac-OBn were dissolved. The resulting solution was added with 2 ml of TFA under ice cooling, followed by stirring at room temperature for 1.5 hours. The reaction mixture was added with a small quantity of toluene and concentrated. Ethyl acetate (50 ml) was then added to the concentrate. The resulting mixture was washed with a saturated aqueous solution of sodium bicarbonate and water, dried over anhydrous magnesium sulfate and then filtered. The filtrate was concentrated. The concentrate containing the title compound was fed to directly for use in the next reaction.

i. Boc-L-MeLeu-D-VALA-L-MeLeu-D-PhLac-OH

In a liquid mixture of 10 ml of methanol and 1 ml of water, 1.1 g (1.74 mmol) of Boc-L-MeLeu-D-VALA-L-MeLeu-D-PhLac-OBn were dissolved. The resulting solution was added with 110 mg of 10% Pd—C in a nitrogen atmosphere, followed by catalytic hydrogenation with hydrogen gas at room temperature under normal pressure for 2 hours. The catalyst was removed by filtration with aid of Hyflo Super Cel and the filtrate was concentrated. The residue was provided, as was, for use in the next reaction.

j. Boc-(L-MeLeu-D-VALA-L-MeLeu-D-PhLac)2-OBn

In 10 ml of THF, 990 mg of L-Boc-MeLeu-D-VALA-L-MeLeu-D-PhLac-OH, 987 mg of H-L-MeLeu-D-VALA-L-MeLeu-D-PhLac-OBn and 282 mg of HOBt were dissolved. The resulting solution was added with 431 mg of DCC under ice cooling, followed by stirring overnight at room temperature (for condensation reaction). The precipitate was filtered off and the filtrate was concentrated. Ethyl acetate (30 ml) was added to the concentrate. The resulting mixture was washed successively with a 5% solution of sodium sulfite, a saturated aqueous solution of sodium bicarbonate and a saturated aqueous solution of sodium chloride, dried over anhydrous magnesium sulfate and then filtered. The filtrate was concentrated. The residue so obtained was then purified by chromatography on a silica gel column (toluene:ethyl acetate=5:1), whereby 1.38 g of the title compound were obtained (yield: 67%).

$[\alpha]_D$ : −63.9° (c=0.1, CHCl$_3$)

k. H-(L-MeLeu-D-VALA-L-MeLeu-D-PhLac)$_2$-OBn

In 4 ml of dichloromethane, 1.20 g (1.02 mmol) of Boc-(L-MeLeu-D-VALA-L-MeLeu-D-PhLac)$_2$-OBn were dissolved. The resulting solution was added with 2 ml of TFA under ice cooling, followed by stirring at room temperature for one hour. The reaction mixture was added with a small quantity of toluene and concentrated. Ethyl acetate (30 ml) was then added to the concentrate. The resulting mixture was washed successively with a saturated aqueous solution of sodium bicarbonate and water, dried over anhydrous magnesium sulfate and filtered. The filtrate was concentrated and the residue so obtained was fed as such for use in the next reaction.

l. H-(L-MeLeu-D-VALA-L-MeLeu-D-PhLac)$_2$-OH

In a liquid mixture of 10 ml of methanol and 1 ml of water, 1.15 g of H-(L-MeLeu-D-VALA-L-MeLeu-D-PhLac)$_2$-OBn were dissolved, followed by the addition of 110 mg of 10% Pd—C in a nitrogen atmosphere. The resulting mixture was subjected to catalytic hydrogenation with hydrogen at room temperature under normal pressure for 2 hours. The catalyst was removed by filtration with aid of Hyflo Super Cel and the filtrate was concentrated. The residue was supplied as such for use in the next reaction.

m. Cyclo-(L-MeLeu-D-VALA-L-MeLeu-D-PhLac)$_2$ (code: PF1022-203)

To a liquid mixture of 680 ml of THF and 200 ml of DMF were added 390 mg of lithium chloride, 685 mg of potassium chloride, 537 mg of sodium chloride, 1.55 g of cesium chloride and 1.76 g of EDCl.HCl. To the resulting mixture, a solution of 910 mg of H-(L-MeLeu-D-VALA-L-MeLeu-D-PhLac)$_2$-OH, 620 mg of HOBt and 0.2 ml of NMM in 110 ml of THF was added, followed by stirring overnight at room temperature (for the ring-closing reaction).

After the solvents were distilled off from the reaction mixture, 230 ml of ethyl acetate and 110 ml of water were added to the residue. The resulting mixture was allowed to separate into two layers. The organic layer so obtained was washed successively with a saturated aqueous solution of sodium bicarbonate, a 5% solution of sodium sulfite and a saturated aqueous solution of sodium chloride, dried over anhydrous magnesium sulfate and then filtered. The filtrate was concentrated. The residue so obtained was purified by subjecting to chromatography on a silica gel column, whereby 645 mg of the title compound were obtained as colorless powder (yield: 56.5%).

$[\alpha]_D$ : −71.6° (c=0.2, MeOH)

$^1$H-NMR(CDCl$_3$): δ=0.79–1.01(m,36H,δ-CH$_3$(MeLeu), γ-CH$_3$(VALA)), 1.38(d,3H,J=0.6,β-CH$_3$(Lac)), 1.53– 2.05 (m,12H,β-CH$_2$,γ-H(MeLeu),β-H(VALA)), 2.60,2.79,2.82, 2.89,2.90,3.11(each s,12H,N—CH$_3$), 2.70–3.27(m,4H,β-CH$_2$(PhLac), 4.36–5.98 (m,8H,α-H(MeLeu,VALA,PhLac)), 7.24–7.28(m,10H,Ph)

MS(FD):M$^+$=1004

EXAMPLE 10

Synthesis of cyclo-(L-MeLeu-D-isoLEUA-L-MeLeu-D-PhLac)$_2$ (code: PF1022-205)

a. 2-Hydroxy-3-methyl-L-pentanoic acid (H-L-isoLEUA-OH, namely, CH$_3$CH$_2$CH(CH$_3$)—CH(OH)COOH)

In a liquid mixture of 500 ml of 1N hydrochloric acid and 50 ml of 1,4-dioxane, 25 g (0.2 mol) of L-isoleucine were dissolved under heating at 40° C., followed by cooling to room temperature. The resulting solution was added dropwise with an aqueous solution of sodium nitrite (39.5 g/50 ml), and they were stirred at room temperature for 5 hours. The resulting reaction mixture was added to an ice-cooled solution mixture of 300 ml of a saturated aqueous solution of sodium chloride and 750 ml of ethyl acetate. The resulting mixture was allowed to separate into two layers. The water layer was extracted four times with 100 ml portions of ethyl acetate. The combined organic layers were dried over anhydrous magnesium sulfate. After the magnesium sulfate was filtered off, the filtrate was concentrated under reduced pressure. The residue was supplied to as such for use in the next reaction.

b. Benzhydryl 2-hydroxy-3-methyl-L-pentanoate (H-L-isoLEUA-OBH)

In 300 ml of ethyl acetate, 2-hydroxy-3-methyl-L-pentanoic acid obtained in the above procedure was dissolved. A solution of diphenyldiazomethane in ethyl acetate (41.2 g/60 ml) was added dropwise to the resulting solution, followed by stirring overnight at room temperature. The resulting reaction mixture was added with 30 ml of acetic acid, followed by washing thrice with 300 ml portions of a saturated aqueous solution of sodium bicarbonate. The organic layer was dried over anhydrous magnesium sulfate and then filtered. The filtrate was concentrated under reduced pressure. The residue so obtained was purified by subjecting to chromatography on a silica gel column (toluene:ethyl acetate=20:1), whereby 9.97 g of the title compound were obtained as an oil (yield: 17%).

$^1$H-NMR(CDCl$_3$): δ=0.82(t,3H,J=7.3,δ-Me), 0.97(d,3H, J=6.6,γ-Me), 1.19(m,2H,CH$_2$), 1.90(m,1H,β-H), 2.70(d,1H, J=5.90,OH), 4.2(m,1H,α-H), 7.0(s,1H,CHPh$_2$), 7.26–7.40 (m,10H,Ph)

c. Boc-L-MeLeu-D-isoLEUA-OBH

In 30 ml of THF were dissolved 5.25 g of triphenylphosphine and 5.97 g (20 mmol) of H-L-isoLEUA-OBH. A solution of 5.89 g of Boc-L-MeLeu-OH and 3.78 ml of DEAD in 10 ml of THF was added dropwise to the resulting solution, followed by stirring overnight at room temperature. The precipitate was filtered off and 300 ml of ethyl acetate were added to the residue. The resulting mixture was washed successively with a saturated aqueous solution of sodium bicarbonate, a saturated aqueous solution of sodium chloride and water, followed by drying over anhydrous magnesium sulfate. After filtration, the filtrate was concentrated. The residue was purified by subjecting to chromatography on a silica gel column (toluene:ethyl acetate=50:1→10:1), whereby 7.01 g of the title compound were obtained as an oil (yield: 66.7%).

$^1$H-NMR(CDCl$_3$): δ=1.44(s,9H,t-Bu), 4.8,5.1(each m, 1H,α-H(MeLeu)), 5.14(t,1H,α-H(isoLEUA)), 6.96(s,1H,C HPh$_2$), 7.26–7.37(m,10H,Ph)

$[\alpha]_D$=−13.8° (c=0.55, CHCl$_3$)

d. Boc-L-MeLeu-D-isoLEUA-OH

In a liquid mixture of 50 ml of methanol and 5 ml of water, 5.26 g (10 mmol) of Boc-L-MeLeu-D-isoLEUA-OBH were dissolved. The resulting solution was added with 530 mg of 10% Pd—C in a nitrogen atmosphere, followed by catalytic hydrogenation with hydrogen at room temperature under normal pressure for 5 hours. The catalyst was filtered off with aid of Hyflo Super Cel, and the filtrate was concentrated. The residue was supplied as such for use in the next reaction.

e. H-L-MeLeu-D-PhLac-OBn

In 2 ml of dichloromethane, 2.90 g (6.0 mmol) of Boc-L-MeLeu-D-PhLac-OBn were dissolved. The resulting solution was added with 2 ml of TFA under ice cooling, followed by stirring at room temperature for 3 hours. The reaction mixture was added with a small quantity of toluene and concentrated. Ethyl acetate (50 ml) was added to the concentrate. The resulting mixture was washed successively with a saturated aqueous solution of sodium bicarbonate and water, dried over anhydrous magnesium sulfate and then filtered. The filtrate was concentrated and the residue obtained was supplied to as such for use in the next reaction.

f. Boc-L-MeLeu-D-isoLEUA-L-MeLeu-D-PhLac-OBn

In 30 ml of THF, 2.93 g of Boc-L-MeLeu-D-isoLEUA-OH, 2.14 g of H-L-MeLeu-D-PhLac-OBn and 904 mg of HOBt were dissolved. The resulting solution was added with 1.38 g of DCC under ice cooling, followed by stirring overnight at room temperature (for the condensation). After the precipitate was filtered off from the reaction mixture, the filtrate was concentrated. To the residue, 100 ml of ethyl acetate were added. The resulting mixture was washed successively with 100 ml of a 5% aqueous solution of sodium sulfite, 100 ml of a saturated aqueous solution of sodium bicarbonate and 100 ml of a saturated aqueous solution of sodium chloride, dried over anhydrous magnesium sulfate and filtered. The filtrate was then concentrated. The residue as obtained was purified by subjecting to chromatography on a silica gel column (toluene:ethyl acetate=10:1), whereby 1.80 g of the title compound were obtained as a colorless oil (yield: 47.9%).

g. H-L-MeLeu-D-isoLEUA-L-MeLeu-D-PhLac-OBn

In 2 ml of dichloromethane, 875 mg (1.2 mmol) of Boc-L-MeLeu-D-isoLEUA-L-MeLeu-D-PhLac-OBn were dissolved. The resulting solution was added with 2 ml of TFA under ice cooling, followed by stirring at room temperature for 1.5 hours. The reaction mixture was added with a small quantity of toluene and concentrated. Ethyl acetate (30 ml) was added to the concentrate. The resulting mixture was washed successively with a saturated aqueous solution of sodium bicarbonate and water, dried over anhydrous magnesium sulfate and then filtered. The filtrate was concentrated and the residue obtained was fed as such for use in the next reaction.

h. Boc-L-MeLeu-D-isoLEUA-L-MeLeu-D-PhLac-OH

In a liquid mixture of 10 ml of methanol and 1 ml of water, 875 mg (1.2 mmol) of Boc-L-MeLeu-D-isoLEUA-L-MeLeu-D-PhLac-OBn were dissolved. The resulting solution was added with 85 mg of 10% Pd/C under a nitrogen atmosphere, followed by catalytic hydrogenation with hydrogen at room temperature under normal pressure for 3 hours. The catalyst was filtered off with aid of Hyflo Super Cel and the filtrate was concentrated. The residue obtained was supplied as such for use in the next reaction.

i. Boc-(L-MeLeu-D-isoLEUA-L-MeLeu-D-PhLac)$_2$-OBn

In 10 ml of THF, 668 mg of Boc-L-MeLeu-D-isoLEUA-L-MeLeu-D-PhLac-OH, 732 mg of H-L-MeLeu-D-isoLEUA-L-MeLeu-D-PhLac-OBn and 194 mg of HOBt were dissolved. The resulting solution was added with 297 mg of DCC under ice cooling, followed by stirring overnight at room temperature (for the condensation). After the precipitate was filtered off, the filtrate was concentrated. Ethyl acetate (30 ml) was added to the residue. The resulting mixture was washed successively with a 5% aqueous solution of sodium sulfite, a saturated aqueous solution of sodium bicarbonate and a saturated aqueous solution of sodium chloride, dried over anhydrous magnesium sulfate and filtered. The filtrate was concentrated, followed by purifying the resultant residue by chromatography on a silica gel column (toluene:ethyl acetate=10:1→5:1), whereby 555 mg of the title compound were obtained as a colorless oil (yield: 37.3%).

j. H-(L-MeLeu-D-isoLEUA-L-MeLeu-D-PhLac)$_2$-OBn

In 2 ml of dichloromethane, 555 mg (0.45 mmol) of Boc-(L-MeLeu-D-isoLEUA-L-MeLeu-D-PhLac)$_2$-OBn were dissolved. The resulting solution was added with 2 ml of TFA under ice cooling, followed by stirring at room temperature for 1 hour. The reaction mixture was added with a small quantity of toluene and concentrated. Ethyl acetate (30 ml) was added to the concentrate. The resulting mixture was washed successively with a saturated aqueous solution of sodium bicarbonate and water, dried over anhydrous magnesium sulfate and filtered. The filtrate was then concentrated. The residue obtained was supplied as such for use in the next reaction.

k. H-(L-MeLeu-D-isoLEUA-L-MeLeu-D-PhLac)$_2$-OH

In a liquid mixture of 5 ml of methanol and 0.5 ml of water, 506 mg of H-(L-MeLeu-D-isoLEUA-L-MeLeu-D-PhLac)$_2$-OBn were dissolved. The resulting solution was added with 50 mg of 10% Pd—C under a nitrogen atmosphere, followed by catalytic hydrogenation with hydrogen at room temperature under normal pressure for 2 hours. The catalyst was filtered off with aid of Hyflo Super Cel and the filtrate was concentrated. The residue obtained was supplied as such for use in the next reaction.

l. Cyclo-(L-MeLeu-D-isoLEUA-L-MeLeu-D-PhLac)$_2$ (Code: PF1022-205)

To a liquid mixture of 400 ml of THF and 120 ml of DMF were added 216 mg of lithium chloride, 380 mg of potassium chloride, 298 mg of sodium chloride, 859 mg of cesium chloride and 977 mg of EDCLHCl. The resulting mixture was added at room temperature with a solution, which had been obtained in advance by dissolving 529 mg of H-(L-MeLeu-D-isoLEUA-L-MeLeu-D-PhLac)$_2$-OH, 345 mg of HOBt and 0.11 ml of NMM in 60 ml of THF, followed by stirring overnight (for the ring-closing reaction). After the solvent was distilled off, the residue was added with 230 ml of ethyl acetate and 110 ml of water. The resulting mixture was allowed to separate into two layers. The organic layer so obtained was washed successively with a saturated aqueous solution of sodium bicarbonate, a 5% aqueous solution of sodium sulfite and a saturated aqueous solution of sodium chloride, dried over anhydrous magnesium sulfate and then filtered. The filtrate was concentrated, followed by the purification of the residue by chromatography on a silica gel column (chloroform:ethyl acetate =10:1→5:1) and then by reversed phase chromatography on a silylized silica gel column (CH$_3$CN:H$_2$O=85:15→90:10). The purified product was lyophilized, whereby 134 mg of the title compound were obtained as white powder (yield: 29.0%).

$[\alpha]_D = -74°$ (c=0.37, MeOH)

MS(FD): M$^+$=1032

EXAMPLE 11

Synthesis of cyclo-(L-MeLeu-D-norLEUA-L-MeLeu-D-PhLac)$_2$ (Code: PF1022-207)

a. 2-Hydroxy-L-hexanoic acid (abbreviation: H-L-norLEUA-OH, namely, CH$_3$—(CH$_2$)$_3$—CH(OH)COOH)

In a liquid mixture of 140 ml of 1N—HCl and 10 ml of 1,4-dioxane, 9.18 g (70 mmol) of L-norleucine were dissolved. An aqueous solution of sodium sulfite (14.5 g/20 ml) was added dropwise to the resulting solution, followed by stirring at room temperature for 3 hours. After ice cooling, the resultant reaction mixture was added to a liquid mixture of 200 ml of a saturated aqueous solution of sodium chloride and 400 ml of ethyl acetate. The resulting mixture was allowed to separate into two layers. The water layer so obtained was extracted twice with 100 ml portions of ethyl acetate. The combined organic layers were dried over anhydrous magnesium sulfate. The magnesium sulfate was filtered off and the filtrate was concentrated under reduced pressure. The concentrate obtained was fed as such for use in the next reaction.

b. Benzhydryl 2-hydroxy-L-hexanoate (H-L-norLEUA-OBH)

In 90 ml of ethyl acetate, the 2-hydroxy-L-hexanoic acid (H-L-norLEUA-OH) was dissolved. A solution (15.1 g/30 ml) of diphenyldiazomethane in ethyl acetate was added dropwise to the resulting solution, followed by stirring overnight at room temperature. The reaction mixture was adjusted to pH 2 with 2N—HCl, followed by washing thrice with 200 ml portions of a saturated aqueous solution of sodium bicarbonate. The organic layer so obtained was dried over anhydrous magnesium sulfate and then filtered. The filtrate was thereafter concentrated under reduced pressure. The residue obtained was then purified by subjecting to chromatography on a silica gel column (toluene:ethyl acetate=20:1), whereby 11.35 g of the title compound were obtained as pale yellow crystals (yield: 54.7%).

$^1$H-NMR(CDCl$_3$): δ=0.85(t,3H,J=7.0,Me), 1.28–1.83(m, 6H,β-,γ-,δ-CH$_2$), 2.70(d,1H,J=6.2,OH), 4.30(dd,1H,J=2.9, 6.2,α-H), 6.95(s,1H,CHPh$_2$), 7.25– 7.38(m,10H,Ph)

c. Boc-L-MeLeu-D-norLEUA-OBH

In 30 ml of THF, 3.98 g of triphenylphosphine and 5.37 g of H-L-norLEUA-OBH were dissolved. To the resulting solution, a solution of 3.68 g of Boc-L-MeLeu-OH and 2.36 ml of DEAD in 10 ml of THF was added dropwise, followed by stirring overnight at room temperature. From the reaction solution obtained by this condensation reaction, the precipitate was filtered off. Ethyl acetate (200 ml) was added to the filtrate. The resulting mixture was washed successively with a saturated aqueous solution of sodium bicarbonate, a saturated aqueous solution of sodium chloride and water, dried over anhydrous magnesium sulfate and filtered. The filtrate was concentrated. The residue obtained was purified by subjecting to chromatography on a silica gel column (toluene:ethyl acetate=20:1→10:1), whereby 7.5 g of the title compound were obtained as an oil (yield: 95%).

$^1$H-NMR(CDCl$_3$): δ=0.82–0.94(m,9H,δ-Me(MeLeu), ε-Me(norLEUA)), 1.44(d,9H,t-Bu), 2.71(d,3H,NMe), 4.74–4.78, 4.98–5.02(each m, 1H,α-H(MeLeu)), 5.11(t,1H, α-H(norLEAU)), 6.96(s,1H,CHPh$_2$), 7.26–7.37(m,10H,Ph)

[α]$_D$ =–9.4° (c=0.55,CHCl$_3$)

d. Boc-L-MeLeu-D-norLEUA-OH

In a liquid mixture of 50 ml of methanol and 5 ml of water, 5.00 g (9.52 mmol) of Boc-L-MeLeu-D-norLEUA-OBH were dissolved. To the resulting solution, 500 mg of 10% Pd—C were added under a nitrogen atmosphere, followed by catalytic hydrogenation with hydrogen at room temperature under normal pressure for 2 hours. The catalyst was filtered off with aid of Hyflo Super Cel and the filtrate was concentrated. The residue obtained was fed as such for use in the next reaction.

d. H-L-MeLeu-D-PhLac-OBn

In 2 ml of dichloromethane, 2.41 g (5.0 mmol) of Boc-L-MeLeu-D-PhLac-OBn were dissolved. To the resulting solution, 2 ml of TFA were added under ice cooling, followed by stirring at room temperature for one hour. The reaction mixture was added with a small quantity of toluene and then concentrated. Ethyl acetate (50 ml) was added to the concentrate. The resulting mixture was washed successively with a saturated aqueous solution of sodium bicarbonate and water, dried over anhydrous magnesium sulfate and filtered. The filtrate was then concentrated and the residue obtained was fed as such for use in the next reaction.

e. Boc-L-MeLeu-D-norLEUA-L-MeLeu-D-PhLac-OBn

In 30 ml of THF, 3.0 g of Boc-L-MeLeu-D-norLEUA-OH, 2.19 g of H-L-MeLeu-D-PhLac-OBn and 924 mg of HOBt were dissolved. To the resulting solution, 1.41 g of DCC were added under ice cooling, followed by stirring overnight at room temperature. After the precipitate was filtered off, the filtrate was concentrated. The residue was added with 100 ml of ethyl acetate. The resulting mixture was washed successively with 100 ml of a 5% aqueous solution of sodium sulfite, 100 ml of a saturated aqueous solution of sodium bicarbonate and 100 ml of a saturated aqueous solution of sodium chloride, dried over anhydrous magnesium sulfate and then filtered. The filtrate was concentrated. The residue obtained was then purified by subjecting it to chromatography on a silica gel column (toluene:ethyl acetate=10:1), whereby 2.17 g of the title compound were obtained as a colorless oil (yield: 52.5%).

$^1$H-NMR(CDCl$_3$): δ=0.83–0.98(m,15H,δ-Me(MeLeu), ε-Me(norLEAU), 1.44(d,t-Bu), 2.80(m,6H,NMe), 7.13–7.36(m,10H,Ph)

f. H-L-MeLeu-D-norLEUA-L-MeLeu-D-PhLac-OBn

In 2 ml of dichloromethane, 985 mg (1.36 mmol) of Boc-L-MeLeu-D-norLEUA-L-MeLeu-D-PhLac-OBn were dissolved. TFA (2 ml) was added to the resulting solution under ice cooling, followed by stirring at room temperature for 30 minutes. The reaction mixture was added with a small quantity of toluene and then concentrated. Ethyl acetate (30 ml) was added to the concentrate. The resulting mixture was washed successively with a saturated aqueous solution of sodium bicarbonate and water, dried over anhydrous magnesium sulfate and then filtered. The filtrate was concentrated and the residue obtained was fed as such for use in the next reaction.

g. Boc-L-MeLeu-D-norLEUA-L-MeLeu-D-PhLac-OH

In a liquid mixture of 10 ml of methanol and 1 ml of water, 1.10 g (1.52 mmol) of Boc-L-MeLeu-D-norLEUA-L-MeLeu-D-PhLac-OBn were dissolved. The resulting solution was added with 110 mg of 10% Pd—C under a nitrogen atmosphere, followed by catalytic hydrogenation with hydrogen at room temperature under normal pressure for 4 hours. The catalyst was filtered off with aid of Hyflo Super Cel and the filtrate was concentrated. The residue obtained was fed as such for use in the next reaction.

h. Boc-(L-MeLeu-D-norLEUA-L-MeLeu-D-PhLac)$_2$-OBn

In 10 ml of THF, 892 mg of Boc-L-MeLeu-D-norLEUA-L-MeLeu-D-PhLac-OH, 800 mg of L-MeLeu-D-norLEUA-L-MeLeu-D-PhLac-OBn and 220 mg of HOBt were dissolved. The resulting solution was added with 337 mg of DCC under ice cooling, followed by stirring overnight at room temperature. The precipitate as formed was filtered off and the filtrate was concentrated. Ethyl acetate (30 ml) was added to the residue. The resulting mixture was washed successively with a 5% aqueous solution of sodium sulfite, a saturated aqueous solution of sodium bicarbonate and a saturated aqueous solution of sodium chloride, dried over anhydrous magnesium sulfate and then filtered. After the filtrate was concentrated, the residue as obtained was then purified by subjecting it to chromatography on a silica gel column (toluene:ethyl acetate=10:1→5:1, whereby 920 mg of the title compound were obtained as a colorless oil (yield: 54.5%).

[α]$_D$=–50.5° (c=0.3,CHCl$_3$)

i. H-(L-MeLeu-D-norLEUA-L-MeLeu-D-PhLac)$_2$-OBn

In 2 ml of dichloromethane, 920 mg (0.74 mmol) of Boc-(L-MeLeu-D-norLEUA-L-MeLeu-D-PhLac)$_2$-OBn were dissolved. The resulting solution was added with 1 ml of TFA under ice cooling, followed by stirring at room temperature for one hour. The reaction mixture was added with a small quantity of toluene and then concentrated, followed by the addition of 30 ml of ethyl acetate. The resulting mixture was washed successively with a saturated aqueous solution of sodium bicarbonate and water, dried over anhydrous magnesium sulfate and filtered. The filtrate was concentrated and the residue obtained was fed as such for use in the next reaction.

j. H-(L-MeLeu-D-norLEUA-L-MeLeu-D-PhLac)$_2$-OH

In a liquid mixture of 10 ml of methanol and 1 ml of water, 850 mg of H-(L-MeLeu-D-norLEUA-L-MeLeu-D-PhLac)$_2$-OBn were dissolved. The resulting solution was added with 10% Pd—C under a nitrogen atmosphere, followed by catalytic hydrogenation with hydrogen at room temperature under normal pressure for 2 hours. The catalyst was filtered off with aid of Hyflo Super Cel. The filtrate was then concentrated. The residue was supplied as such for use in the next reaction.

k. Cyclo-(L-MeLeu-D-norLEUA-L-MeLeu-D-PhLac)$_2$ (Code: PF1022-207)

In a liquid mixture of 500 ml of THF and 150 ml of DMF were dissolved 270 mg of lithium chloride, 4.7 g of potassium chloride, 370 mg of sodium chloride, 1.06 g of cesium chloride and 1.2 g of EDCI.HCl. The mixture so obtained was added with a solution of 633 mg of (L-MeLeu-D-norLEUA-L-MeLeu-D-PhLac)$_2$-OH, 426 mg of HOBt and 0.13 ml of NMM in 80 ml of THF, followed by stirring overnight at room temperature. After the solvents were distilled off, the residue was added with 150 ml of ethyl acetate and 80 ml of water. The resulting mixture was allowed to separate into two layers. The organic layer so obtained was washed successively with a saturated aqueous solution of sodium bicarbonate, a 5% aqueous solution of sodium sulfite and a saturated aqueous solution of sodium chloride, dried over anhydrous magnesium sulfate and then filtered. The filtrate was concentrated. The residue so obtained was purified by chromatography on a silica gel column (chloroform:ethyl acetate=10:1→5:1), whereby 274 mg of the title compound were obtained as pale yellowish white powder (yield: 35.8%).

$[\alpha]_D = -57.2°$ (c=0.1,MeOH)

$^1$H-NMR(CDCl$_3$): δ=0.79–1.04(m,30H,δ-Me(MeLeu), ε-Me(norLEAU)), 1.37–1.70(m,β-,γ-,δ-CH$_2$(norLEUA),β-CH$_2$, γ-H(MeLeu)), 2.72–3.20(m,12H,NMe), 4.88(d,4H,CH$_2$—Ph), 5.09–5.92(m,8H,α-H), 7.27–7.31(m,10H,Ph)

MS(FD): M$^+$=1032

EXAMPLE 12

Synthesis of cyclo-(L-MeLeu-D-Lac-L-MeLeu-D-PhLac-L-MeLeu-D-norLEUA-L-MeLeu-D-PhLac) (Code: PF1022-225)

a. Boc-L-MeLeu-D-Lac-L-MeLeu-D-PhLac-L-MeLeu-D-norLEUA-L-MeLeu-D-PhLac-OBn

In 20 ml of methylene chloride, 1.02 g of Boc-L-MeLeu-D-Lac-L-MeLeu-D-PhLac-OH and 0.98 g of H-L-MeLeu-D-norLEUA-L-MeLeu-D-PhLac-OBn were dissolved. The resulting solution was added with 0.74 ml of diisopropylethylamine and 0.52 g of BOP-Cl under ice cooling, followed by stirring at the same temperature for 16 hours (for the condensation). The reaction mixture was added with 50 ml of methylene chloride. The resulting mixture was then washed successively with a 5% aqueous solution of potassium bisulfate, a 7% aqueous solution of sodium bicarbonate and a 20% aqueous solution of sodium chloride, each 50 ml, dried over anhydrous magnesium sulfate and then concentrated under reduced pressure. The residue was purified by chromatography on a silica gel column (toluene:ethyl acetate=6:1→5:1), whereby 1.52 g of the title compound were obtained as white powder (yield: 80.5%).

$[\alpha]_D^{20}$ : −58.1° (c=0.21, CHCl$_3$)

$^1$H-NMR(CDCl$_3$): δ=0.70–1.00(m,27H,δ-Me(MeLeu),ε-ME(norLEAU)), 1.44(s,9H,t-Bu), 1.15–1.85(m,21H,β-Me (lac), β-CH$_2$,γ-H(MeLeu),β-CH$_2$,γCH$_2$,δ-CH$_2$ (norLEUA), 2.65–3.30(m,16H,N-Me,β-CH$_2$(PhLac)), 4.30–5.50(m.8H, α-H(MeLeu),α-H(PhLac),α-H(Lac),α-H(norLEAU)), 5.12 (d,2H,J=0.89,CH$_2$Ph), 7.10– 7.40 (m, 15H, Ph)

b. H-L-MeLeu-D-Lac-L-MeLeu-D-PhLac-L-MeLeu-D-norLEUA-L-MeLeu-D-PhLac-OBn

In 6 ml of methylene chloride, 1.48 g of Boc-L-MeLeu-D-Lac-L-MeLeu-D-PhLac-L-MeLeu-D-norLEUA-L-MeLeu- D-PhLac-OBn were dissolved. To the resulting solution, 3 ml of TFA were added dropwise under ice cooling, followed by reaction at room temperature for 30 minutes (for removal of Boc). The reaction mixture was concentrated, followed by the addition of toluene to and by azeotropical removal of TFA. The residue obtained was dissolved in 100 ml of ethyl acetate. The resulting solution was washed successively with a 7% aqueous solution of sodium bicarbonate and a 20% aqueous solution of sodium chloride, each 100 ml, dried over anhydrous magnesium sulfate and then concentrated under reduced pressure, whereby 1.37 g of the title compound were obtained as a colorless oil. This oil was provided without purification for use in the next reaction.

$^1$H-NMR(CDCl$_3$): δ=0.82–0.99(m,27H,δ-Me(MeLeu), ε-Me(norLEUA)), 1.20–1.81(m,21H,β-Me(Lac),β-CH$_2$ (MeLeu), γ-H(MeLeu),β-CH$_2$,γ-CH$_2$,δ-CH$_2$(norLEUA)), 2.73–3.35(m,16H,N-Me,β-CH$_2$(PhLac)), 5.06–5.55(m,8H, α-H(MeLeu),α-H(PhLac),α-H(Lac), α-H(norLEAU)), 5.12 (d,2H,J=0.89,CH$_2$Ph), 7.18– 7.37(m,15H,Ph)

c. H-L-MeLeu-D-Lac-L-MeLeu-D-PhLac-L-MeLeu-D-norLEUA-L-MeLeu-D-PhLac-OH

In 26 ml of methanol, 1.32 g of H-L-MeLeu-D-Lac-L-MeLeu-D-PhLac-L-MeLeu-D-norLEUA-L-MeLeu-D-PhLac-OBn were dissolved. To the resulting solution, 0.13 g of 10% palladium-carbon and a drop of acetic acid were added under a nitrogen atmosphere, followed by catalytic hydrogenation with hydrogen at room temperature under normal pressure for one hour.

The catalyst was filtered off and then, the filtrate was concentrated, whereby 1.21 g of the title compound were obtained as white powder. The compound was provided without purification for use in the next reaction.

$[\alpha]_D^{20}$ : −22.1° (c=0.21, CHCl$_3$)

$^1$H-NMR(CDCl$_3$): δ=0.70–1.05(m,27H,δ-Me(MeLeu),ε-ME(norLEAU)), 1.15–1.85(m,21H,β-Me(Lac),β-CH$_2$ (MeLeu),γ-H(MeLeu),β-CH$_2$,γCH$_2$,δ-CH$_2$(norLEUA), 2.40–3.15(m,16H,N-Me,β-CH$_2$(PhLac)), 5.05–5.70(m,8H, α-H(MeLeu),α-H(PhLac),α-H(Lac),α-H(norLEAU)), 7.25 (m,10H,Ph)

d. Cyclo-(L-MeLeu-D-Lac-L-MeLeu-D-PhLac-L-MeLeu-D-norLEUA-L-MeLeu-D-PhLac (Code: PF022-225)

In 165 ml of THF, 1.18 g of H-L-MeLeu-D-Lac-L-MeLeu-D-PhLac-L-MeLeu-D-norLEUA-L-MeLeu-D-PhLac-OH, 0.79 g of HOBt and 0.51 ml of NMM were dissolved. The resulting solution was added to a mixture of 0.50 g of lithium chloride, 0.68 g of sodium chloride, 0.87 g of potassium chloride, 1.97 g of cesium chloride, 2.24 g of EDCI-HCl, 1060 ml of THF and 307 ml of DMF, followed by stirring at room temperature for 16 hours (for the ring-closing reaction). The reaction mixture was concentrated and the residue obtained was dissolved in 120 ml of ethyl acetate. The resulting solution was washed successively with a 7% aqueous solution of sodium bicarbonate, a 5% aqueous solution of potassium bisulfate and a 20% aqueous solution of sodium chloride, each 120 ml, dried over anhydrous magnesium sulfate and then concentrated under reduced pressure. The residue was purified by chromatography on a silica gel column (toluene:ethyl acetate= 3:1→2:1), whereby 0.95 g of the title compound was obtained as white powder (yield: 82.0%).

$[\alpha]_D^{20}$ : −70.6° (c=0.23, CHCl$_3$)

$^1$H-NMR(CDCl$_3$): δ=0.80–1.05(m,27H,δ-Me(MeLeu),ε-Me(norLEAU)), 1.23–1.76(m,21H,β-Me(Lac),β-CH$_2$(MeLeu), γ-H(MeLeu),β-CH$_2$,γ-CH$_2$,δ-CH$_2$(norLEUA), 2.67–3.15(m,16H,N-Me,β-CH$_2$(PhLac)), 5.00–5.70(m,8H, α-H(MeLeu),α-H(PhLac),α-H(Lac),α-H

EXAMPLE 13

Synthesis of cyclo-(L-MeLeu-D-VALA-L-MeLeu-D-Lac)$_2$ (Code: PF-1022-209)

a. Boc-L-MeLeu-D-VALA-L-MeLeu-D-Lac-OBn

In 35 ml of THF, 2.22 g of Boc-L-MeLeu-D-VALA-OH, 2.22 g of H-L-MeLeu-D-Lac-OBn and 1.04 g of HOBt were dissolved. To the resulting solution, 1.59 g of DCC were added under ice cooling, followed by stirring at 5° C. for 47 hours. The precipitate so formed was filtered off and the filtrate was then concentrated. The residue was dissolved in 100 ml of ethyl acetate. The resulting solution was washed successively with 100 ml of a 7% aqueous solution of sodium bicarbonate and 100 ml of a 30% aqueous solution of sodium chloride, dried over anhydrous sodium sulfate and then concentrated. The residue was purified by chromatography on a silica gel column (toluene:ethyl acetate= 10:1→5:1), whereby 2.12 g of the title compound were obtained (yield: 52%).

$[\alpha]_D^{20}$ : −50° (c=0.17, CHCl$_3$)

$^1$H-NMR(CDCl$_3$): δ=0.87–1.02(m,18H,δ-Me(Me-Leu),γ-ME(VALA)), 1.45(m,9H,t-Bu), 1.51(d,3H,β-Me(Lac)), 1.41–1.74(m,7H,β-CH$_2$,γ-H(Me-Leu),β-H(VALA), 2.84(m, 3H,NMe), 2.97(d,3H,NMe), 5.15(d,2H,CH$_2$Ph), 5.01–5.23 (m,4H,α-H(MeLeu),α-H(VALA),α-H(Lac)), 7.35(s,5H,Ph)

b. Boc-L-MeLeu-D-VALA-L-MeLeu-D-Lac-OH

In 15 ml of methanol, 1.48 g of Boc-L-MeLeu-D-VALA-L-MeLeu-D-Lac-OBn were dissolved under a nitrogen atmosphere. To the resulting solution, 0.15 g of 10% Pd/C was added, followed by catalytic hydrogenation with hydrogen at room temperature under normal pressure for one hour. The catalyst was filtered off with aid of Hyflo Super Cel. The filtrate was concentrated, whereby the title compound was obtained as a colorless oil. The compound was provided without purification for use in the next reaction.

$^1$H-NMR(CDCl$_3$): δ=0.90–0.98(m,18H,δ-Me(MeLeu),γ-Me(VALA), 1.45(s,9H,t-Bu), 1.58(d,3H,β-Me(Lac)), 2.81 (s,3H,NMe), 3.06(d,3H,NMe), 4.91–5.30(m,4H,α-H (MeLeu), α-H(VALA),α-H(Lac))

c. H-L-MeLeu-D-VALA-L-MeLeu-D-Lac-OBn

In 8 ml of methylene chloride, 1.62 g of Boc-L-MeLeu-D-VALA-L-MeLeu-D-Lac-OBn were dissolved. To the resulting solution, 2.4 ml of TFA were added dropwise under ice cooling, followed by stirring at room temperature for one hour. The reaction mixture was concentrated, followed by adding toluene to the residue and by azeotropically distilling off TFA and toluene. The residue so obtained was dissolved in 80 my of ethyl acetate. The resulting solution was washed with 80 ml of a 7% aqueous solution of sodium bicarbonate and a 30% aqueous solution of sodium chloride, dried over anhydrous magnesium sulfate and then concentrated, whereby the title compound was obtained as a colorless oil.

The compound was provided without purification for use in the next reaction.

$^1$H-NMR(CDCl$_3$): δ=0.88–0.99(d×2,12H,δ-Me(MeLeu) ), 1.02(d,6H,γ-Me(VALA)), 2.37(s3H,NMe), 3.01(d,3H, NMe), 5.20(d,2H,CH$_2$Ph), 5.06–5.34(m,4H,α-H(MeLeu), α-H(VALA),α-H(Lac)), 7.35(s,5H,Ph)

d. Boc-(L-MeLeu-D-VALA-L-MeLeu-D-Lac)$_2$-OBn

In 28 ml of THF were dissolved 1.12 g of Boc-L-MeLeu-D-VALA-L-MeLeu-D-Lac-OH, 1.20 g of L-MeLeu-D-VALA-L-MeLeu-D-Lac-OBn, 0.33 g of HOBt and 0.30 ml of triethylamine. To the resulting solution, 0.55 g of DCC was added under ice cooling, followed by stirring at 5° C. for 2 days. After the precipitate was filtered off, the filtrate was concentrated. The residue was then dissolved in 75 ml of ethyl acetate. The resulting solution was washed successively with 75 ml of a 5% aqueous solution of potassium bisulfate, 75 ml of a 7% aqueous solution of sodium bicarbonate and 75 ml of a 30% aqueous solution of sodium chloride, dried over anhydrous magnesium sulfate and then concentrated. The residue was purified by chromatography on a silica gel column (toluene:ethyl acetate=5:1), whereby 1.40 g of the title compound were obtained as white prism crystals (yield: 64.0%).

$[\alpha]_D^{20}$ : −63.1° (c=0.2, CHCl$_3$)

$^1$H-NMR(CDCl$_3$): δ=0.87–0.95(m,24H,δ-Me(MeLeu)), 1.00(d,12H,γ-Me(VALA), 1.45(d,9H,t-Bu), 1.44–1.53(d×2, 6H,β-Me(Lac)), 1.50–1.76(m,12H,β-CH$_2$,γ-H(MeLeu)), 2.13(m,2H,β-H(VALA)), 2.83–3.12(m,12H,NMe), 5.15(d, 2H,CH$_2$Ph), 5.02–5.33(m,8H,α-H(MeLeu), α-H(VALA),α-H(Lac)), 7.36(s,5H,Ph)

e. H-(L-MeLeu-D-VALA-L-MeLeu-D-Lac)$_2$-OBn

In 8 ml of methylene chloride, 1.30 g of Boc-(L-MeLeu-D-VALA-L-MeLeu-D-Lac)$_2$-OBn were dissolved. To the resulting solution, 4 ml of TFA were added dropwise under ice cooling, followed by stirring at the same temperature for one hour. The reaction mixture was concentrated, followed by addition of toluene and by azeotropically distilling off TFA and toluene. The residue so obtained was dissolved in 65 ml of ethyl acetate. The resulting mixture was washed with 65 ml of a 7% aqueous solution of sodium bicarbonate and 35 ml of a 30% aqueous solution of sodium chloride, dried over anhydrous magnesium sulfate and then concentrated, whereby the title compound was obtained as white prism crystals. The compound was provided without purification for use in the next reaction.

$^1$H-NMR(CDCl$_3$): δ=0.87–1.04(m,36H,β-Me(MeLeu),γ-Me(VALA)), 1.45(d×2,6H,β-Me(Lac)), 1.70–1.80(m,12H, β-CH$_2$,γ-H(MeLeu)), 2.15(m,2H,β-H(VALA), 2.92–3.16 (m,12H,NMe), 5.17(d,2H,CH$_2$Ph), 5.02–5.37(m,8H,α-H (MeLeu), α-H(VALA),α-H(Lac)), 7.32(s,5H,Ph)

f. H-(L-MeLeu-D-VALA-L-MeLeu-D-Lac)$_2$-OH

In 12 ml of methanol, 1.15 g of H-(L-MeLeu-D-VALA-L-MeLeu-D-Lac)$_2$-OBn were dissolved under a nitrogen atmosphere. To the resulting solution, 0.12 g of 10% Pd/C was added, followed by catalytic hydrogenation with hydrogen at room temperature under normal pressure for 1.5 hours. The catalyst was filtered off with aid of Hyflo Super Cel. The filtrate was concentrated, whereby the title compound was obtained as a colorless oil. The compound was provided without purification for use in the next reaction.

$^1$H-NMR(CDCl$_3$): δ=0.85–1.06(m,36H,δ-Me(MeLeu),γ-Me(VALA)), 1.45(d,6H,β-Me(Lac)), 1.71–1.86(m,12H,β-CH$_2$, γ-H(MeLeu)), 2.20(m,2H,β-H(VALA)), 2.51–3.14(m, 12H,NMe), 5.16–5.28(m,8H,α-H(MeLeu), α-H(VALA), α-H(Lac))

g. Cyclo-(L-MeLeu-D-VALA-L-MeLeu-D-Lac)$_2$

In 140 ml of THF, 1.0 g of H-(L-MeLeu-D-VALA-L-MeLeu-D-Lac)$_2$, 0.77 g of HOBt and 0.51 ml of NMM were dissolved. The resulting solution was added to a solution, which had been prepared separately by dissolving 0.49 g of lithium chloride, 0.67 g of sodium chloride, 0.85 g of potassium chloride, 1.93 g of cesium chloride and 2.20 g of EDCI.HCl in a liquid mixture of 900 ml of THF and 260 ml of DMF. The resulting admixture was stirred at room temperature for 23 hours. The reaction mixture obtained was concentrated and the residue was dissolved in 100 ml of ethyl acetate. The resulting solution was washed successively with 100 ml of a 7% aqueous solution of sodium bicarbonate, 100 ml of a 5% aqueous solution of potassium bisulfate and 100 ml of a 30% aqueous solution of sodium chloride, dried over anhydrous magnesium sulfate and concentrated. The residue was purified by chromatography on a silica gel column (toluene:ethyl acetate=3:1), whereby 0.90 g of the title compound was obtained (yield: 92%).

$[\alpha]_D^{20}$ : −65.1° (c=0.1, MeOH)

$^1$H-NMR(CDCl$_3$): δ=0.86–1.08(m,36H,δ-Me(MeLeu),γ-Me(VALA)), 1.43(d,6H,β-Me(Lac)), 1.60–2.30(m,14H,β-CH$_2$, γ-H(MeLeu),β-H(VALA)), 2.86–3.22(m,12H,NMe), 4.82–5.90(m,8H,α-H(MeLeu), α-H(VALA),α-H(Lac))

EXAMPLE 14

Synthesis of cyclo-(L-MeLeu-D-OctA-L-MeLeu-D-Lac-L-MeLeu-D-PhLac-L-MeLeu-D-Lac) (Code: PF1022-216)

a. H-L-MeLeu-D-PhLac-L-MeLeu-D-Lac-OBn

In 2 ml of dichloromethane, 993 mg (1.45 mmol) of Boc-L-MeLeu-D-PhLac-L-MeLeu-D-Lac-OBn were dissolved. The resulting solution was added with 2 ml of TFA under ice cooling, followed by stirring at room temperature for one hour. The reaction mixture was added with a small quantity of toluene and concentrated. Ethyl acetate (25 ml) was then added to the concentrate. The resulting mixture was washed successively with a saturated aqueous solution of sodium bicarbonate and water, dried over anhydrous magnesium sulfate and filtered. The filtrate was concentrated and the residue was fed as such for use in the next reaction.

b. Boc-L-MeLeu-D-OctA-L-MeLeu-D-Lac-OH

In a liquid mixture of 10 ml of methanol and 1 ml of water, 984 mg (1.45 mmol) of Boc-L-MeLeu-D-OctA-L-MeLeu-D-Lac-OBn (wherein OctA represents the above-described 2-hydroxyoctanoic acid residue) were dissolved. The resulting mixture was added with 98 mg of 10% Pd—C under a nitrogen atmosphere, followed by catalytic hydrogenation with hydrogen at room temperature under normal pressure for 3 hours. The catalyst was filtered off with aid of Hyflo Super Cel and the filtrate was concentrated. The residue was provided, as such for use in the next reaction.

c. Boc-L-MeLeu-D-OctA-L-MeLeu-D-Lac-L-MeLeu-D-PhLac-L-MeLeu-D-Lac-OBn

In 20 ml of THF, 845 mg of Boc-L-MeLeu-D-OctA-L-MeLeu-D-Lac-OH, 844 mg of H-L-MeLeu-D-PhLac-L-MeLeu-D-Lac-OBn and 235 mg of HOBt were dissolved. The resulting solution was added with 359 mg of DCC under ice cooling, followed by stirring at room temperature for 4 hours. After the precipitate was filtered off, the filtrate was concentrated. Ethyl acetate (100 ml) was added to the residue. The resulting mixture was washed successively with a 5% aqueous solution of sodium sulfite, a saturated aqueous solution of sodium bicarbonate and a saturated aqueous solution of sodium chloride, dried over anhydrous magnesium sulfate and filtered. The filtrate was then concentrated. The residue obtained was then purified by subjecting it to chromatography on a silica gel column (toluene:ethyl acetate=10:1), whereby 1.14 g of the title compound were obtained as a colorless oil (yield: 68.4%).

$[\alpha]_D$=45.7° (c=0.1,MeOH)

d. H-L-MeLeu-D-OctA-L-MeLeu-D-Lac-L-MeLeu-D-PhLac-L-MeLeu-D-Lac-OBn

In 2 ml of dichloromethane, 1.13 g (0.984 mmol) of Boc-L-MeLeu-D-OctA-L-MeLeu-D-Lac-L-MeLeu-D-PhLac-L-MeLeu-D-Lac-OBn were dissolved. The resulting solution was added with 2 ml of TFA under ice cooling, followed by stirring at room temperature for 30 minutes. The reaction mixture was added with a small quantity of toluene and then concentrated. Ethyl acetate(30 ml) was added to the concentrate. The resulting mixture was washed successively with a saturated aqueous solution of sodium bicarbonate and water, dried over anhydrous magnesium sulfate and filtered. The filtrate was concentrated and the residue was fed as such for use in the next reaction.

e. H-L-MeLeu-D-OctA-L-MeLeu-D-Lac-L-MeLeu-D-PhLac-L-MeLeu-D-Lac-OH

In a liquid mixture of 10 ml of methanol and 1 ml of water, 1.140 g of H-L-MeLeu-D-OctA-L-MeLeu-D-Lac-L-MeLeu-D-PhLac-L-MeLeu-D-Lac-OBn were dissolved. The resulting solution was added with 114 mg of 10% Pd—C under a nitrogen atmosphere, followed by catalytic hydrogenation with hydrogen at room temperature under normal pressure for 2 hours. The catalyst was filtered off with aid of Hyflo Super Cel. The filtrate was then concentrated. The residue was provided, as such for use in the next reaction.

f. Cyclo-(L-MeLeu-D-OctA-L-MeLeu-D-Lac-L-MeLeu-D-PhLac-L-MeLeu-D-Lac) (Code: PF1022-216)

To a liquid mixture of 650 ml of THF and 195 ml of DMF, 417 mg of lithium chloride, 733 mg of potassium chloride, 575 mg of sodium chloride, 1.66 g of cesium chloride and 1.89 g of EDCI.HCl were added. The resulting mixture was added with a solution, which had been obtained in advance by dissolving 865 mg of H-L-MeLeu-D-OctA-L-MeLeu-D-Lac-L-MeLeu-D-PhLac-L-MeLeu-D-Lac-OH, 664 mg of HOBt and 0.22 ml of NMM in 100 ml of THF, followed by stirring overnight at room temperature.

After the solvent was distilled off from the reaction mixture, the residue was added with 400 ml of ethyl acetate and 400 ml of water. The resulting mixture was allowed to separate into two layers. The organic layer so obtained was washed successively with a saturated aqueous solution of sodium bicarbonate, a 5% aqueous solution of sodium sulfite and a saturated aqueous solution of sodium chloride, dried over anhydrous magnesium sulfate and then filtered. The filtrate was concentrated. The concentrate was purified by chromatography on a silica gel column (chloroform:ethyl acetate=10:1→4:1) and then by reversed phase chromatography on a silylized silica gel column (MeCN:H$_2$O=9:1), whereby 210 mg of the title compound were obtained as white powder.

$[\alpha]_D$=−73° (c=0.17,MeOH)

$^1$H-NMR(CDCl$_3$): δ=0.80–1.05(m,27H,Me(OctA),δ-Me (MeLeu)), 1.29–1.37(m,8H,ζ-,ε-,δ-,γ-,CH$_2$(OctA)), 1.41(d, 6H,β-Me(Lac)), 1.68–1.85(m,14H,β-CH$_2$,γ-H(MeLeu), β-CH$_2$(OctA)), 2.74–3.17(m,12H,NMe), 4.46–4.52, 5.07–5.71(m,8H,α-H(MeLeu,OctA,Lac)), 7.27(bs,5H,Ph)

MS(FD): M$^+$=942

EXAMPLE 15

Synthesis of cyclo-(L-MeLeu-D-OctA-L-MeLeu-D-Lac)$_2$ (Code: PF1022-217)

a. Benzhydryl 2-hydroxy-D-octanoate (H-D-OctA-OBH)

In 25.5 ml of ethyl acetate, 1.68 g of 2-hydroxy-D-octanoic acid were dissolved. To the resulting solution, a solution (2.14 g/19 ml) of diphenyldiazomethane in ethyl acetate was added dropwise at room temperature over one hour, followed by stirring for four hours. The reaction mixture was added with 0.63 ml of acetic acid,followed by stirring for three hours to decompose the excess of diphenyldiazomethane. The reaction solution was then adjusted to pH 6.5 with a 7% aqueous solution of NaHCO$_3$ under ice cooling. The so treated solution was allowed to separate into two layers. The organic layer so obtained was washed with water, dried over anhydrous magnesium sulfate and concentrated. The residue was purified by chromatography on a silica gel column (toluene:ethyl acetate=100:1→50:1), whereby 3.27 g of the title compound were obtained as white crystals (yield: 95.5%).

$[\alpha]_D^{20}$ : +22.0° (c=0.28, CHCl$_3$)

$^1$H-NMR(CDCl$_3$): δ=0.86(t,3H,Me), 1.23–1.42(m,8H,ζ-, ε-,δ-,γ-CH$_2$), 1.62–1.86(m,2H,β-CH$_2$), 2.75(d,1H,OH), 4.30 (m,1H,α-H), 6.95(s,1H,C$\underline{H}$Ph$_2$), 7.33(s,10H,Ph)

b. Boc-L-MeLeu-D-OctA-OBH

In 30 ml of pyridine, 2.46 g of Boc-L-MeLeu-OH were dissolved. The resulting solution was added with 3.27 g of H-D-OctA-OBH, 1.62 g of HOBt and 2.48 g of DCC under ice cooling, followed by stirring at the same temperature for 37 hours. After the precipitate was filtered off, the filtrate was concentrated. The residue was dissolved in 150 ml of ethyl acetate. The resulting solution was washed successively with 150 ml of a 5% aqueous solution of potassium bisulfate, 150 ml of a 7% aqueous solution of sodium bicarbonate and 150 ml of a 5% aqueous solution of sodium chloride, dried over anhydrous magnesium sulfate and then concentrated. The residue was purified by chromatography on a silica gel column (toluene:ethyl acetate=100:1→50:1), whereby 4.73 g of the title compound were obtained as a colorless oil (yield: 85.4%).

$[\alpha]_D^{20}$ : –8.5° (c=0.84, CHCl$_3$)

$^1$H-NMR(CDCl$_3$): δ=0.85(t,3H,Me(OctA)), 0.92(dd,6H, δ-Me(MeLeu)), 1.23(m,8H,ζ-,ε-,δ-,γ-CH$_2$(OctA)), 1.44(d, 9H,t-Bu), 2.72(d,3H,NMe), 4.74–5.02 (dd×2,1H,α-H (MeLeu)), 5.12(t,1H,OH(OctA)), 6.90(s,1H,C$\underline{H}$Ph$_2$), 7.32 (s,10H,Ph)

c. Boc-L-MeLeu-D-OctA-OH

In 47 ml of methanol, 4.66 g of Boc-L-MeLeu-D-OctA-OBH were dissolved under a nitrogen atmosphere. The resulting solution was added with 0.47 g of 10% Pd/C and a drop of acetic acid, followed by catalytic hydrogenation with hydrogen at room temperature under normal pressure for one hour. The catalyst was filtered off with aid of Hyflo Super Cel. The filtrate was concentrated, whereby the title compound was obtained as a colorless oil. The compound was provided without purification for use in the next reaction.

$^1$H-NMR(CDCl$_3$): δ=0.88(t,3H,Me(OctA)), 0.95(t,6H,δ-Me(MeLeu)), 1.28(m,8H,ζ-,ε-,δ-,γ-CH$_2$(OctA)), 1.45(d,9H, t-Bu), 2.81(s,3H,NMe), 4.80(dd×2,1H,α-H(MeLeu)), 5.01 (t,1H,α-H(OctA))

d. Boc-L-MeLeu-D-OctA-L-MeLeu-D-Lac-OBn

In 50 ml of tetrahydrofuran, 3.26 g of Boc-L-MeLeu-D-OctA-OH, 2.81 g of H-L-MeLeu-D-Lac-OBn and 1.37 g of HOBt were dissolved. The resulting solution was added with 2.08 g of DCC and 2.7 ml of pyridine under ice cooling, followed by stirring at room temperature for 40 hours. After the precipitate was filtered off, the filtrate was concentrated. The residue was dissolved in 300 ml of ethyl acetate. The resulting solution was washed successively with 300 ml of a 5% aqueous solution of potassium bisulfate, 300 ml of a 7% aqueous solution of sodium bicarbonate and 300 ml of a 20% aqueous solution of sodium chloride, dried over anhydrous magnesium sulfate and concentrated. The residue was purified by chromatography on a silica gel column (toluene:ethyl acetate=10:1), whereby 3.23 g of the title compound were obtained as white crystals (yield: 56.8%).

$[\alpha]_D^{20}$ : –37.9° (c=0.27, CHCl$_3$)

$^1$H-NMR(CDCl$_3$): δ=0.87–1.01(m,15H,Me(OctA),δ-Me (MeLeu)), 1.28(m,8H,ζ-,ε-,δ-,γ-CH$_2$(OctA)), 1.45(d,9H,t-Bu), 1.51(d,3H,β-Me(Lac)), 1.64–1.79(m,8H,β-CH$_2$, γ-H (MeLeu), β-CH$_2$(OctA)), 2.87(d,3H,NMe), 2.95(d,3H, NMe), 5.07–5.34 (m,6H,C$\underline{H}_2$Ph), α-H(MeLeu), α-H(OctA), α-H(Lac), 7.38(s,5H,Ph)

e. Boc-L-MeLeu-D-OctA-L-MeLeu-D-Lac-OH

In 10 ml of methanol, 990 mg of Boc-L-MeLeu-D-OctA-L-MeLeu-D-Lac-OBn were dissolved under a nitrogen atmosphere. The resulting solution was added with 99 mg of 10% Pd/C and a drop of acetic acid, followed by catalytic hydrogenation with hydrogen at room temperature under normal pressure for one hour. The catalyst was filtered off with aid of Hyflo Super Cel. The filtrate was then concentrated, whereby the title compound was obtained as a colorless oil. The compound was provided without purification for use in the next reaction.

$^1$H-NMR(CDCl$_3$): δ=0.84–0.92(m,15H,Me(OctA),δ-Me (MeLeu)), 1.23(m,8H,ζ-,ε-,δ-,γ-CH$_2$(OctA)), 1.41(d,9H,t-Bu), 1.43(d,3H,β-Me(Lac)), 1.62–1.72(m,8H,β-CH$_2$,γ-H (MeLeu),β-CH$_2$(OctA)), 2.77(s,3H,NMe), 3.97(d,3H, NMe), 4.80–5.32(m,4H,α-H(MeLeu), α-H(OctA),α-H (Lac))

f. H-L-MeLeu-D-OctA-L-MeLeu-D-Lac-OBn

In 1.5 ml of TFA, 962.4 mg of Boc-L-MeLeu-D-OctA-L-MeLeu-D-Lac-OBn were dissolved under ice cooling. The resulting solution was stirred at the same temperature for 30 minutes, followed by further stirring at room temperature for 30 minutes. The reaction mixture was concentrated. Toluene was then added to the concentrate, which was then azeotropically distilled to remove TFA. The residue obtained was dissolved in 75 ml of ethyl acetate. The resulting solution was washed successively with 75 ml of a 7% aqueous solution of sodium bicarbonate and 75 ml of a 30% aqueous solution of sodium chloride, dried over anhydrous magnesium sulfate and concentrated, whereby the title compound was obtained as a colorless oil. The compound was provided without purification for use in the next reaction.

$^1$H-NMR(CDCl$_3$): δ=0.85–0.99(m,15H,Me(OctA),δ-Me (MeLeu)), 1.27(m,8H,ζ-,ε-,δ-,γ-CH$_2$(OctA)), 1.46(d,6H,β-Me(Lac)), 1.66–1.82(m,8H,β-CH$_2$,γ-H(MeLeu), β-CH$_2$ (OctA)), 2.39(s,3H,NMe), 2.96(s,3H,NMe), 5.07–5.36(m, 2H,C$\underline{H}_2$Ph),α-H(MeLeu), α-H(OctA), α-H(Lac)), 7.37(s, 5H,Ph)

g. Boc-(L-MeLeu-D-OctA-L-MeLeu-D-Lac)$_2$-OBn

In 13 ml of THF, 857 mg of Boc-L-MeLeu-D-OctA-L-MeLeu-D-Lac-OH, 819 mg of H-L-MeLeu-D-OctA-L-MeLeu-D-Lac-OBn, 237 mg of HOBt and 0.24 ml of pyridine were dissolved. The resulting solution was added with 362 mg of DCC under ice cooling, followed by stirring at room temperature for 16 hours. The precipitate was filtered off and the filtrate was concentrated. The residue was dissolved in 75 ml of ethyl acetate. The resulting solution was washed successively with 75 ml of a 5% aqueous solution of potassium bisulfate, 75 ml of a 7% aqueous solution of sodium bicarbonate and 75 ml of a 20% aqueous solution of sodium chloride, dried over anhydrous magnesium sulfate and concentrated. The residue was purified by chromatography on a silica gel column (toluene:ethyl acetate=5:1), whereby 875 mg of the title compound were obtained as white crystals (yield: 53.8%).

$[\alpha]_D^{20}$ : –48.8° (c=0.1, CHCl$_3$)

$^1$H-NMR(CDCl$_3$): δ=0.85–1.01(m,30H,Me(OctA),δ-Me (MeLeu)), 1.28(bs,16H,ζ-,ε-,δ-,γ-CH$_2$(OctA)), 1.45(d,9H,t-Bu), 1.52(d,6H,β-Me(Lac)), 1.72–1.77(m,16H,β-CH$_2$,γ-H (MeLeu),β-CH$_2$(OctA)), 2.83–3.10(s,12H,N-Me), 5.14–5.30(m,10H,CH$_2$Ph),α-H(MeLeu), α-H(OctA),α-H (Lac)), 7.36(s,5H,Ph)

h. H-(L-MeLeu-D-OctA-L-MeLeu-D-Lac)$_2$-OBn

In 4.4 ml of methylene chloride, 870 mg of Boc-(L-MeLeu-D-OctA-L-MeLeu-D-Lac)$_2$-OBn were dissolved. The resulting solution was added dropwise with 26 ml of TFA under ice cooling, followed by stirring at room temperature for one hour. The reaction mixture was then concentrated. Toluene was added to the concentrate, which was azeotropically distilled to remove TFA therefrom. The residue so obtained was dissolved in 50 ml of ethyl acetate. The resulting solution was washed with 50 ml of a 7% aqueous solution of sodium bicarbonate and 50 ml of a 20% aqueous solution of sodium chloride, dried over anhydrous magnesium sulfate and concentrated, whereby the title compound was obtained as a colorless oil. The compound was provided without purification for use in the next reaction.

$^1$H-NMR(CDCl$_3$): δ=0.86–1.01(m,30H,Me(OctA),δ-Me (MeLeu)), 1.26(d,16H,ζ-,ε-,δ-,γ-CH$_2$(OctA)), 1.41–1.77(m, 22H,β-Me(Lac),β-CH$_2$,γ-H(MeLeu),β-CH$_2$(OctA)), 2.93(s, 6H,NMe), 3.10(d,6H,NMe), 5.20(d,2H,CH$_2$Ph), 5.08–5.35 (m,8H,α-H(MeLeu),α-H(OctA),α-H(Lac)), 7.35(s,5H,Ph)

i. H-(L-MeLeu-D-OctA-L-MeLeu-D-Lac)$_2$-OH

In 8 ml of methanol, 794.0 mg of H-(L-MeLeu-D-OctA-L-MeLeu-D-Lac)$_2$-OBn were dissolved under a nitrogen atmosphere. To the resulting solution, 80 mg of 10% Pd/C and a drop of acetic acid were added, followed by catalytic hydrogenation with hydrogen at room temperature under normal pressure for 1.5 hours. The catalyst was filtered off with aid of Hyflo Super Cel. The filtrate was concentrated, whereby the title compound was obtained as a colorless oil. The compound was provided without purification for use in the next reaction.

$^1$H-NMR(CDCl$_3$): δ=0.88–1.06(m,30H,Me(OctA),δ-CH$_3$ (MeLeu)), 1.26(bs,16H,ζ-,ε-,δ-,γ-CH$_2$(OctA)), 1.46(d,6H, β-Me(Lac),1.60–1.95(m,16H,β-CH$_2$,γ-H(MeLeu), β-CH$_2$ (OctA)), 3.02(t,6H,NMe), 3.08(d,6H,NMe), 4.50–5.44(m, 8H,α-H(MeLeu),α-H(OctA), α-H(Lac))

j. Cyclo-(L-MeLeu-D-OctA-L-MeLeu-D-Lac)$_2$

In 140 ml of THF, 1.00 g of H-(L-MeLeu-D-OctA-L-MeLeu-D-Lac)$_2$-OH, 0.77 g of HOBt and 0.51 ml of NMM were dissolved. The resulting solution was added to a mixture of 0.49 g of lithium chloride, 0.67 g of sodium chloride, 0.85 g of potassium chloride, 1.93 g of cesium chloride, 2.20 g of EDCI.HCl, 900 ml of THF and 260 ml of DMF, followed by stirring at room temperature for 23 hours. After the reaction mixture was concentrated, the residue was dissolved in 100 ml of ethyl acetate. The resulting solution was washed successively with 100 ml of a 7% aqueous solution of sodium bicarbonate, 100 ml of 5% potassium bisulfate and 100 ml of a 30% aqueous solution of sodium chloride, dried over anhydrous magnesium sulfate and concentrated. The residue was purified by chromatography on a silica gel column (toluene:ethyl acetate=3:1), whereby 0.90 g of the title compound was obtained (yield: 92%).

[α]$_D^{20}$ : −46.30 (c=0.1, MeOH)

$^1$H-NMR(CDCl$_3$): δ=0.84–1.06(m,30H,Me(OctA),δ-Me (MeLeu)), 1.29(bs,16H,ζ-,ε-,δ-,γ-CH$_2$(OctA)), 1.43(d,6H, β-Me(Lac),1.68–1.85(m,16H,β-CH$_2$,γ-H(MeLeu), β-CH$_2$ (OctA)), 2.87(d,6H,NMe), 3.08(d,6H,NMe), 5.41–5.53(m, 8H,α-H(MeLeu),α-H(OctA), α-H(Lac))

EXAMPLE 16

Synthesis of cyclo-(L-MeLeu-D-PhLac-L-Leu-D-Lac)$_2$ (Code: PF1022-218)

a. Boc-L-Leu-D-Lac-OBH

In 30 ml of THF, 5.13 g (20 mmol) of H-L-Lac-OBH and 10.5 g of triphenylphosphine were dissolved. To the resulting solution, a solution of 5.64 g of Boc-L-Leu-OH and 6.08 ml of DEAD in THF were added dropwise under ice cooling, followed by stirring at room temperature for 3 days. The reaction mixture was then concentrated. The precipitate was filtered off, followed by further concentration. Ethyl acetate (300 ml) was added to the residue. The resulting mixture was washed successively with a saturated aqueous solution of sodium bicarbonate, a saturated aqueous solution of sodium chloride and water, dried over anhydrous magnesium sulfate and filtered. The filtrate was then concentrated. The residue obtained was purified by subjecting it to chromatography on a silica gel column (toluene:ethyl acetate=20:1→10:1), whereby 9.57 g of the title compound were obtained in a stoichiometric yield (9.57 g).

$^1$H-NMR: δ=1.5(s,9H,t-Bu), 4.4(m.1H,CH), 4.9(d,1H,J= 6.3,CH), 5.2(d,2H,J=4.9,CH$_2$Ph), 7.26–7.30(m,10H,Ph)

b. Boc-L-Leu-D-Lac-OH

In a liquid mixture of 100 ml of methanol and 10 ml of water, 9.56 g (20.4 mmol) of Boc-L-Leu-D-Lac-OH were dissolved, followed by the addition of 956 mg of 10% Pd—C under a nitrogen atmosphere. The resulting mixture was subjected to catalytic hydrogenation with hydrogen: at room temperature under normal pressure for 2 hours. The catalyst was filtered off with aid of Hyflo Super Cel, and the filtrate was concentrated. The residue was provided, as such for use in the next reaction.

c. Boc-L-Leu-D-Lac-OBn

In 35 ml of DMSO, 5.0 g of Boc-L-Leu-D-Lac-OH were dissolved. To the resulting solution, 1.52 ml of benzyl bromide were added at 35° C. After the temperature was increased to 40° C., the resulting mixture was added with 2.94 g of potassium carbonate, followed by stirring at the same temperature for 5 hours. Ethyl acetate (200 ml) was added to the reaction mixture. The resulting mixture was washed successively with water and a 10% aqueous solution of sodium chloride, dried over anhydrous magnesium sulfate and filtered. The filtrate was then concentrated. The residue as obtained was purified by subjecting it to chromatography on a silica gel column, whereby 4.19 g of the title compound were obtained as a colorless oil (yield: 100%).

d. Boc-L-Leu-D-Lac-OH

In 4 ml of dichloromethane, 4.0 g (10.2 mmol) of Boc-L-Leu-D-Lac-OBn were dissolved. The resulting solution was added with 6 ml of TFA under ice cooling, followed by stirring at room temperature for 3 hours. A small quantity of toluene was added to the reaction mixture, followed by concentration. Ethyl acetate (200 ml) was added to the residue obtained. The resulting mixture was washed successively with a saturated aqueous solution of sodium bicarbonate and water, dried over anhydrous magnesium sulfate and filtered. The filtrate was then concentrated. The residue was provided, as such for use in the next reaction.

e. Boc-L-MeLeu-D-PhLac-OH

In a liquid mixture of 60 ml of methanol and 6 ml of water, 5.84 g (12 mmol) of Boc-L-MeLeu-D-PhLac-OBn were dissolved. To the resulting solution, 584 mg of 10% Pd—C were added under a nitrogen atmosphere, followed by catalytic hydrogenation with hydrogen at room temperature under normal pressure for 4 hours. The catalyst was filtered off with aid of Hyflo Super Cel. The filtrate was concentrated. The residue was provided, as such for use in the next reaction.

f. Boc-L-MeLeu-D-PhLac-L-Leu-D-Lac-OBn

In 50 ml of THF, 4.45 g of Boc-L-MeLeu-D-PhLac-OH, 2.87 g of H-L-Leu-D-Lac-OBn and 1.95 g of HOBt were dissolved. To the resulting solution, 2.97 g of DCC were added under ice cooling, followed by stirring at room temperature for 3 hours. After the precipitate was filtered off, the filtrate was concentrated. Ethyl acetate (100 ml) was added to the concentrate. The resulting mixture was washed successively with water, a saturated aqueous solution of sodium bicarbonate and a saturated aqueous solution of sodium chloride, dried over anhydrous magnesium sulfate and filtered. The filtrate was then concentrated. The residue obtained was purified by subjecting it to chromatography on a silica gel column (toluene:ethyl acetate=50:1→10:1), whereby 6.12 g of the title compound were obtained as a colorless oil (yield: 90%).

$^1$H-NMR: δ=0.85–0.91(m,12H,Me×4), 1.45(s,9H,t-Bu), 2.8(s,3H,NMe), 5.07–5.18(m,2H,C$\underline{H}_2$Ph), 7.19–7.39(m, 10H,Ph)

g. H-L-MeLeu-D-PhLac-L-Leu-D-Lac-OBn

In 3 ml of dichloromethane, 2.68 g (1.74 mmol) of Boc-L-MeLeu-D-PhLac-L-Leu-D-Lac-OBn were dissolved. To the resulting solution, 3 ml of TFA were added under ice cooling, followed by stirring at room temperature for 3 hours. A small quantity of toluene was added to the reaction mixture, followed by concentration. Ethyl acetate (50 ml) was added to the residue as obtained. The resulting mixture was washed with a saturated aqueous solution of sodium bicarbonate, dried over anhydrous magnesium sulfate and filtered. The filtrate was then concentrated. The residue was provided, as such for use in the next reaction.

h. Boc-L-MeLeu-D-PhLac-L-Leu-D-Lac-OH

In a liquid mixture of 30 ml of methanol and 3 ml of water, 2.68 g (4 mmol) of Boc-L-MeLeu-D-PhLac-L-Leu-D-Lac-OBn were dissolved. The resulting solution was added with 268 mg of 10% Pd—C under a nitrogen atmosphere, followed by catalytic hydrogenation with hydrogen at room temperature under normal pressure for 3 hours. The catalyst was filtered off with aid of Hyflo Super Cel. The residue was provided, as such for use in the next reaction.

i. Boc-(L-MeLeu-D-PhLac-L-Leu-D-Lac)$_2$-OBn

In 30 ml of THF, 2.20 g of Boc-L-MeLeu-D-PhLac-L-Leu-D-Lac-OH, 2.18 g of H-L-MeLeu-D-PhLac-L-Leu-D-Lac-OBn and 649 mg of HOBt were dissolved. The resulting solution was added with 990 mg of DCC under ice cooling, followed by stirring at room temperature for 4 hours. The precipitate was filtered off and the filtrate was concentrated. Ethyl acetate (100 ml) was added to the concentrate. The resulting mixture was washed successively with a 5% solution of sodium bisulfate, a saturated aqueous solution of sodium bicarbonate and a saturated aqueous solution of sodium chloride, dried over anhydrous magnesium sulfate and filtered. The filtrate was concentrated. Ethyl acetate (100 ml) was added to the concentrate. The resulting mixture was washed successively with a 5% solution of sodium bisulfate, a saturated aqueous solution of sodium bicarbonate and a saturated aqueous solution of sodium chloride, dried over anhydrous magnesium sulfate and filtered. The filtrate was concentrated. The residue as obtained was purified by chromatography on a silica gel column (toluene:ethyl acetate= 10:1), whereby 3.18 g of the title compound were obtained as a colorless oil (yield: 70.4%).

j. H-(L-MeLeu-D-PhLac-L-Leu-D-Lac)$_2$-OBn

In 6 ml of dichloromethane, 3.10 g (2.75 mmol) of Boc-(L-MeLeu-D-PhLac-L-Leu-D-Lac)$_2$-OBn were dissolved. To the resulting solution, 5 ml of TFA were added under ice cooling, followed by stirring at room temperature for one hour. A small quantity of toluene was added to the reaction mixture, followed by concentration. Ethyl acetate (100 ml) was added to the residue obtained. The resulting mixture was washed successively with a saturated aqueous solution of sodium bicarbonate and water, dried over anhydrous magnesium sulfate and filtered. The filtrate was then concentrated. The residue was provided, as such for use in the next reaction.

k. H-(L-MeLeu-D-PhLac-L-Leu-D-Lac)$_2$-OH

In a liquid mixture of 30 ml of methanol and 3 ml of water, 3.06 g of H-(L-MeLeu-D-PhLac-L-Leu-D-Lac)$_2$-OBn were dissolved. The resulting solution was added with 306 mg of 10% Pd—C under a nitrogen atmosphere, followed by catalytic hydrogenation with hydrogen at room temperature under normal pressure for 3 hours. The catalyst was filtered off with aid of Hyflo Super Cel, and the filtrate was concentrated. The residue obtained was provided as such for use in the next reaction.

l. Cyclo-(L-MeLeu-D-PhLac-L-Leu-D-Lac)$_2$ (code: PF1022-218)

To a liquid mixture of 1875 ml of THF and 563 ml of DMF, 1.16 g of lithium chloride, 2.05 g of potassium chloride, 1.6 g of sodium chloride, 4.62 g of cesium chloride and 5.262 g of EDCI.HCl were added. The resulting mixture was added at room temperature with a solution, which had been prepared separately by dissolving 2.47 g of H-(L-MeLeu-D-PhLac-L-Leu-D-Lac)$_2$-OH, 1.85 g of HOBt and 0.6 ml of NMM in 300 ml of THF. The admixture obtained was stirred overnight at room temperature. After the solvents were distilled off, the residue was added with 400 ml of ethyl acetate and 400 ml of water. The resulting mixture was allowed to separate into two layers. The organic layer so obtained was washed successively with a saturated aqueous solution of sodium bicarbonate, a 5% aqueous solution of sodium sulfite and a saturated aqueous solution of sodium chloride, dried over anhydrous magnesium sulfate and then filtered. The filtrate was concentrated, and the residue obtained was purified by chromatography on a silica gel column (chloroform:ethyl acetate=10:1), whereby 1.57 mg of the title compound were obtained as colorless powder (yield: 62%).

$[\alpha]_D$=−41° (c=0.5,MeOH)

$^1$H-NMR(CD$_3$OD): δ=0.83–0.94(m,24H,δ-Me(MeLeu, Leu), 1.39–1.42(bd,6H,Me(Lac)), 1.69–2.22(m,12H,β-CH$_2$, γ-H(MeLeu,Leu)), 2.93–3.34(m,10H,N-Me(MeLeu), CH$_2$ (PhLac), 3.74–3.77, 4.52–4.58, 4.80–4.85, 5.10–5.31(m,8H, α-H(MeLeu,Leu,PhLac,Lac)), 7.21–7.36(m,10H,Ph)

MS(FD): M$^+$=920

EXAMPLE 17

Synthesis of cyclo-(L-MeLeu-D-Lac-L-Leu-D-PhLac)$_2$ (Code: PF1022-219)

a. Boc-L-Leu-D-PhLac-OBn

In 30 ml of pyridine, 2.33 g of Boc-L-Leu-OH, 2.30 g of H-D-PhLac-OBn and 1.34 g of HOBt were dissolved. To the resulting solution, 2.23 g of DCC were added under ice cooling,and the mixture was stirred overnight. The precipitate was filtered off and the filtrate was added with 400 ml of ethyl acetate. The resulting mixture was washed with a 5% aqueous solution of potassium bisulfate, a saturated aqueous solution of sodium bicarbonate and a 5% aqueous solution of sodium chloride, dried over anhydrous magnesium sulfate and filtered. The filtrate was then concentrated. The residue obtained was then purified by subjecting to chromatography on a silica gel column (toluene:ethyl acetate=10:1), whereby 3.57 g of the title compound were obtained as an oil (yield: 84.5%).

$^1$H-NMR(CDCl$_3$):δ=0.69(d,3H,J=6.5,Me), 0.78(d,3H,J=6.5,Me), 1.43(s,9H,t-Bu), 2.35(s,1H,NH), 3.1–3.25(m,1H, CH), 4.36, 4.81(m,1H,CH), 5.14(s,2H,C$\underline{H}_2$Ph), 7.13–7.40 (m,10H,Ph)

b. H-L-Leu-D-PhLac-OBn

In 2 ml of dichloromethane, 3.14 g (6.7 mmol) of Boc-L-Leu-D-PhLac-OBn were dissolved. The resulting solution was added with 4 ml of TFA under ice cooling, followed by stirring at room temperature for 2 hours. A small quantity of toluene was added to the reaction mixture, followed by concentration. Ethyl acetate (50 ml) was added to the resultant residue. The resulting mixture was washed successively with a saturated aqueous solution of sodium bicarbonate and water, dried over anhydrous magnesium sulfate and filtered. The filtrate was then concentrated. The residue was provided, as such for use in the next reaction.

c. Boc-L-MeLeu-D-Lac-OH

In a liquid mixture of 30 ml of methanol and 3 ml of water, 2.85 g (7 mmol) of Boc-L-MeLeu-D-Lac-OBn were dissolved. To the resulting solution, 285 mg of 10% Pd—C were added under a nitrogen atmosphere, followed by catalytic hydrogenation with hydrogen at room temperature under normal pressure for 15 hours. The catalyst was filtered off with aid of Hyflo Super Cel. The filtrate was concentrated. The residue was provided, as such for use in the next reaction.

d. Boc-L-MeLeu-D-Lac-L-Leu-D-PhLac-OBn

In 30 ml of THF, 2.20 g of Boc-L-MeLeu-D-Lac-OH, 2.21 g of H-Leu-L-D-PhLac-OBn and 948 mg of HOBt were dissolved. The resulting solution was added with 1.73 g of DCC under ice cooling, followed by stirring at room temperature for 3 hours. After the precipitate was filtered off, the filtrate was concentrated. Ethyl acetate (100 ml) was added to the residue as obtained. The resulting mixture was washed successively with water, a saturated aqueous solution of sodium bicarbonate and a saturated aqueous solution of sodium chloride, dried over anhydrous magnesium sulfate and filtered. The filtrate was then concentrated. The residue obtained was then purified by subjecting it to chromatography on a silica gel column (toluene:ethyl acetate= 10:1→5:1), whereby 6.38 g of the title compound were obtained as a colorless oil (yield: 72.2%).

e. H-L-MeLeu-D-Lac-L-Leu-D-PhLac-OBn

In 3 ml of dichloromethane, 1.55 g (2.31 mmol) of Boc-L-MeLeu-D-Lac-L-Leu-D-PhLac-OBn were dissolved. To the resulting solution, 3 ml of TFA were added under ice cooling, followed by stirring at room temperature for 3 hours. A small quantity of toluene was added to the reaction mixture, followed by concentration. Ethyl acetate (50 ml) was added to the residue obtained. The resulting mixture was washed with a saturated aqueous solution of sodium bicarbonate, dried over anhydrous magnesium sulfate and filtered. The filtrate was then concentrated. The residue was fed to as such for use in the next reaction.

f. Boc-L-MeLeu-D-Lac-L-Leu-D-PhLac-OH

In a liquid mixture of 15 ml of methanol and 1.5 ml of water, 1.61 g (2.4 mmol) of Boc-L-MeLeu-D-Lac-L-Leu-D-PhLac-OBn were dissolved. The resulting solution was added with 160 mg of 10% Pd—C under a nitrogen atmosphere, followed by catalytic hydrogenation with hydrogen at room temperature under normal pressure for 3 hours. The catalyst was filtered off with aid of Hyflo Super Cel. The residue was fed to as such for use in the next reaction.

g. Boc-(L-MeLeu-D-Lac-L-Leu-D-PhLac)$_2$-OBn

In 20 ml of THF, 1.25 g of Boc-L-MeLeu-D-Lac-L-Leu-D-PhLac-OH, 1.29 g of L-MeLeu-D-Lac-L-Leu-D-PhLac-OBn and 373 mg of HOBt were dissolved. The resulting solution was added with 569 mg of DCC under ice cooling, followed by stirring at room temperature for 4 hours. After the precipitate was filtered off, the filtrate was concentrated. Ethyl acetate (100 ml) was added to the residue. The resulting mixture was washed successively with a 5% aqueous solution of sodium sulfite, a saturated aqueous solution of sodium bicarbonate and a saturated aqueous solution of sodium chloride, dried over anhydrous magnesium sulfate and filtered. The filtrate was then concentrated. The residue obtained was purified by subjecting it to chromatography on a silica gel column (toluene:ethyl acetate=3:1), whereby 1.29 g of the title compound were obtained as a colorless oil (yield: 49.7%).

h. H-(L-MeLeu-D-Lac-L-Leu-D-PhLac)$_2$-OBn

In 4 ml of dichloromethane, 1.28 g (1.13 mmol) of Boc-(L-MeLeu-D-Lac-L-Leu-D-PhLac)$_2$-OBn were dissolved. To the resulting solution, 2 ml of TFA were added under ice cooling, followed by stirring at room temperature for one hour. A small quantity of toluene was added to the reaction mixture, followed by concentration. Ethyl acetate (100 ml) was added to the residue obtained. The resulting mixture was washed successively with a saturated aqueous solution of sodium bicarbonate and water, dried over anhydrous magnesium sulfate and filtered. The filtrate was then concentrated. The residue was supplied as such for use in the next reaction.

i. H-(L-MeLeu-D-Lac-L-Leu-D-PhLac)$_2$-OH

In a liquid mixture of 10 ml of methanol and 1 ml of water, 1.22 g of H-(L-MeLeu-D-Lac-L-Leu-D-PhLac)$_2$-OBn were dissolved. To the resulting solution, 122 mg of 10% Pd—C were added under a nitrogen atmosphere, followed by catalytic hydrogenation with hydrogen at room temperature under normal pressure for 3 hours. The catalyst was filtered off with aid of Hyflo Super Cel. The filtrate was concentrated. The residue was supplied as such for use in the next reaction.

j. Cyclo-(L-MeLeu-D-Lac-L-Leu-D-PhLac)$_2$ (Code: PF 1022-219)

To a liquid mixture of 750 ml of THF and 225 ml of DMF were added 446 mg of lithium chloride, 786 mg of potassium chloride, 615 mg of sodium chloride, 1.7 g of cesium chloride and 2.02 g of EDCI.HCl. The resulting mixture was added with a solution, which had been prepared by dissolving 990 mg of H-(L-MeLeu-D-Lac-L-Leu-D-PhLac)$_2$-OH, 712 mg of HOBt and 0.23 ml of NMM in 120 ml of THF. The admixture so obtained was stirred overnight at room temperature. After the solvents were distilled off therefrom, the resultant residue was added with 200 ml of ethyl acetate and 100 ml of water. The resulting mixture was allowed to separate into two layers. The resulting organic layer was washed successively with a saturated aqueous solution of sodium bicarbonate, a 5% aqueous solution of sodium sulfite and a saturated aqueous solution of sodium chloride, dried over anhydrous magnesium sulfate and then filtered. The filtrate was concentrated. The residue obtained was then purified by subjecting it to chromatography on a silica gel column (chloroform:ethyl acetate=10:1), whereby 586 mg of the title compound were obtained as white powder (yield: 55.8%).

$[\alpha]_D=-94°$ (c=0.48, MeOH)

$^1$H-NMR(CD$_3$OD): δ=0.86–0.99(m,24H,δ-Me(MeLeu, Leu), 1.34–1.37(bd,6H,Me(Lac)), 1.70–2.27(m,12H,β-CH$_2$, γ-H(MeLeu)), 3.18–3.31(m,10H,N-Me(MeLeu), CH$_2$ (PhLac), 4.02–4.08, 4.55–4.62, 4.80–4.95, 5.45–5.55(m,8H, α-H(MeLeu,Leu,PhLac,Lac)), 7.12–7.22(,m,10H,Ph)

MS(FD): M$^+$=920

Illustrated in the following Examples 18–34 are processes for preparing the PF 1022 derivatives by introduction of substituent(s).

EXAMPLE 18

Preparation of cyclo-(L-MeLeu-D-PhLac-L-MeLeu-D-Lac-L-MeLeu-D-TYRA(O-t-Bu)-L-MeLeu-D-Lac) (code: PF 1022-215)

In methylene chloride (10 ml) placed in a tube, 701 mg of cyclo(L-MeLeu-D-PhLac-L-MeLeu-D-Lac-L-MeLeu-D-

TYRA-L-MeLeu-D-Lac) (namely, PF 1022E substance) were dissolved, followed by the addition of 1.4 ml of isobutene and 0.11 ml of concentrated sulfuric acid at −40° C. After tube sealing, the temperature of the resulting mixture was allowed to rise back to room temperature. The resulting mixture was stirred for 2 hours. The reaction mixture was ice-cooled and then adjusted to pH 9.0 with 0.6 ml of triethylamine, followed by concentration. The residue was dissolved in 70 ml of ethyl acetate, followed by washing successively with 70 ml of a 5% aqueous solution of potassium bisulfate and 70 ml of a 30% aqueous solution of sodium chloride, drying over anhydrous magnesium sulfate and concentration. The residue was purified by chromatography on a silica gel column (chloroform:ethyl acetate=4:1), whereby 578 mg of the title compound were obtained (yield: 77.6%).

$[\alpha]_D^{20}$ : −92.0° (c=0.1, MeOH)

$^1$H-NMR(CDCl$_3$): δ=0.80–1.05(m,24H,δ-Me(MeLeu)), 1.32(d,9H,t-Bu), 1.40(d,6H,β-Me(Lac)), 1.10–1.80(m,12H, β-CH$_2$,γ-H(MeLeu), 2.70–3.20(m,16H,NMe,β-CH$_2$(PhLac) ), 5.30–5.80(m,8H,α-H(MeLeu),α-H(PhLac),α-H(Lac)), 7.00(dd,4H,t-BuOC$_6$H$_4$), 7.26(d,5H,Ph)

EXAMPLE 19

Preparation of cyclo-(L-MeLeu-D-PhLac-L-MeLeu-D-Lac-L-MeLeu-D-TYRA(OCOC$_{17}$H$_{35}$)-L-MeLeu-D-Lac) (code: PF-1022-006)

In 1.8 ml of THF, 202 mg of the PF 1022E substance, 105 mg of stearic acid, 59.2 mg of HOBt and 0.05 ml of NMM were dissolved, followed by the addition of 82.3 mg of EDCI.HCl under ice cooling. The resulting mixture was stirred at 4° C. for 24 hours. The reaction mixture was diluted with 40 ml of ethyl acetate and 20 ml of hexane, followed by washing successively with 40 ml of water, 40 ml of a saturated aqueous solution of sodium bicarbonate and 40 ml of a saturated aqueous solution of sodium chloride, filtration using a small quantity of silica gel for chromatography, and drying over anhydrous magnesium sulfate. The solvent was distilled off under reduced pressure. The resulting white crystalline powder was purified by chromatography on a silica gel column (chloroform:hexane=1:1→chloroform:ethyl acetate=5:1), followed by crystallization from hexane-methanol-water, whereby 173 mg of the title compound were obtained as white crystals (m.p. 47°–48° C., yield: 67.1%).

$[\alpha]_D^{22}$ : −71° (c=0.15, MeOH)

$^1$H-NMR(CD$^3$OD): δ=0.79–1.28(m,60H,C$_{16}$H$_{33}$CH$_2$), 1.25–1.88(12H,β-CH$_2$,γH(MeLeu)), 1.38(d×2,3H,β-Me (Lac)), 2.27–2.56(m,2H,α-H,C$_{16}$H$_{33}$CH$_2$), 3.05–3.21(m,4H, β-CH$_2$ (PhLac,TYRA), 2.82–3.04(m,12H,NMe), 4.77–5.81 (m,8H,α-H), 7.04–7.35(m,9H,aromatic)

MS(FAB): (M+H)$^+$=1231

EXAMPLE 20

Preparation of cyclo-(L-MeLeu-D-PhLac-L-MeLeu-D-Lac-L-MeLeu-D-TYRA(3,5-diiode)-L-MeLeu-D-Lac) (Code: PF1022-011)

To a solution of 203 mg of the PF 1022E substance in 5 ml of methylene chloride, 130 mg of sodium acetate were added. The resulting mixture was ice-cooled, followed by the addition of 210 mg of iodine. After ice cooling for 30 minutes, the temperature of the reaction mixture was allowed to rise back to room temperature. Triethylamine (0.06 ml) was added to the reaction mixture, followed by stirring at the same temperature for 2.5 hours. The reaction mixture was added with 3 ml of a 10% aqueous solution of sodium thiosulfate, followed by the addition of 20 ml of water and 30 ml of chloroform. The resulting mixture was allowed to separate into two layers. The water layer was extracted with a liquid mixture of 20 ml of ethyl acetate and 8 ml of hexane. The combined organic layers were filtered using a small quantity of silica gel for chromatography, followed by drying over anhydrous sodium sulfate. The solvents were then distilled off under reduced pressure. The residue so obtained was purified by chromatography on a silica gel column (chloroform:ethyl acetate=5:1), whereby 109 mg of the title compound were obtained as crystals (m.p. 124–126° C., yield: 42.4%).

$[\alpha]_D^{20}$ : −92° (c=0.08, MeOH)

$^1$H-NMR(CD$_3$OD): δ=0.78–1.08(m,27H,γ-Me(MeLeu), β-Me(Lac)), 1.33–1.91(m,12H,β-CH$_2$,γ-H(MeLeu)), 1.39 (d×2,3H,β-Me(Lac)), 2.82–3.04(m,12H,NMe), 2.91–3.21 (m,4H,β-CH$_2$(PhLac,TYRA), 4.77–5.82(m,8H,α-H), 7.24–7.70(m,7H,aromatic)

MS(FAB): (M+H)$^+$=1217

EXAMPLE 21

Preparation of cyclo-(L-MeLeu-D-PhLac-L-MeLeu-D-Lac-L-MeLeu-D-TYRA(O-Me,3,5-di-I)-L-MeLeu-D-Lac) (Code: PF 1022-012)

In 2 ml of THF, 70 mg of the 3,5-diiodide of the PF 1022E substance were dissolved, followed by the addition of 0.02 ml of methyl iodide and 7 mg of 60% sodium hydride under ice cooling. The resulting mixture was stirred at 0° C. for 3.5 hours. The reaction mixture was diluted with 20 ml of ethyl acetate, followed by washing with 10 ml of a saturated aqueous solution of sodium chloride, filtering through a small quantity of silica gel for chromatography, and drying over anhydrous sodium sulfate. The solvent was then distilled off under reduced pressure. The residue so obtained was purified by preparative chromatography on a silica gel column (chloroform:ethyl acetate=3:1) and then, by chromatography on a silica gel column (chloroform:ethyl acetate=4:1), whereby 43.8 mg of the title compound were obtained as white powder (m.p. 108°–110° C., yield: 61.9%).

$[\alpha]_D^{20}$ : −98° (c=0.1, MeOH)

$^1$H-NMR(CD$_3$OD): δ=0.79–1.08(m,27H,γ-Me(MeLeu), β-Me(Lac)), 1.12–1.90(m,12H,β-CH$_2$,γ-H(MeLeu)), 1.38, 1.39(d×2,3H,β-Me(Lac)), 2.81–3.14(m,12H,NMe), 4.76–5.82(m,8H,α-H), 7.24–7.81(m,7H,aromatic)

MS(FAB): (M+H)$^+$=1231

EXAMPLE 22

Preparation of cyclo-(L-MeLeu-D-PhLac-L-MeLeu-D-Lac-L-MeLeu-D-TYRA(OCOO-isoBu)-L-MeLeu-D-Lac) (Code: PF 1022-013)

In a liquid mixture of 5 ml of ethyl ether and 5 ml of methylene chloride, 263 mg of Cbz-GABA (namely, γ-aminobutyric acid) were dissolved. To the resulting solution, 0.3 ml of triethylamine and 0.15 ml of isobutyl chloroformate were added under ice cooling. Five minutes after the addition, 640 mg of PF 1022E were added to the resulting mixture, which was then stirred for one hour under ice-cooling. The reaction mixture was diluted with ethyl acetate, followed by washing once with 50 ml of a 5% aqueous solution of potassium bisulfate and twice with 50 ml portions of a saturated aqueous solution of sodium bicarbonate, filtering through a small quantity of silica gel for chromatography, and drying over anhydrous sodium sulfate. The solvent was then distilled off under reduced pressure. The residue so obtained was purified by chromatography on a silica gel column (chloroform:ethyl acetate= 20:1→10:1→8:1), followed by crystallization from ether-hexane, whereby 414 mg of the title compound were obtained as prism crystals (m.p. 95–97° C., yield: 58.6%).

$^1$H-NMR(CDCl$_3$): δ=0.80–1.04(m,27H,γ-Me(MeLeu),β-Me(Lac)), 1.00(d,6H,J=6.7,γMe(isobutyl)), 1.40(d×2,3H,β-Me(Lac)), 1.42–1.79(m,12H,β-CH$_2$,γ-H(MeLeu)), 2.05(m, 1H,β-H(isobutyl)), 2.72–3.06(m,12H,NMe), 3.05–3.18(m, 4H,β-CH$_2$(PhLac,TYRA), 4.02(d×2,2H,α-CH$_2$(isobutyl)), 4.48–5.71(m,8H,α-H), 7.08–7.14,7.21–7.40(m,9H, aromatic)

MS(FAB): (M+H)$^+$=1065

EXAMPLE 23

Preparation of cyclo-(L-MeLeu-D-PhLac-L-MeLeu-D-Lac-L-MeLeu-D-TYRA(OEt)-L-MeLeu-D-Lac) (Code: PF 1022-016)

In 4 ml of THF, 153 mg of the PF 1022E substance were dissolved, followed by the addition of 0.02 ml of ethyl iodide and 15 mg of 60% sodium hydride under ice cooling. The resulting mixture was stirred at 0° C. for 30 minutes. The reaction mixture was diluted with 30 ml of ethyl acetate, followed by washing with a liquid mixture of a 20% aqueous solution of sodium chloride and 10 ml of a 10% aqueous solution of sodium thiosulfate, filtering through a small quantity of silica gel for chromatography, and drying over anhydrous sodium sulfate. The solvent was thereafter distilled off under reduced pressure. The residue so obtained was purified by chromatography on a silica gel column (chloroform: ethyl acetate=8:1→5:1), followed by lyophilization using 1,4-dioxane, whereby 158 mg of the title compound were obtained.

$[α]_D^{20}$ : −67° (c=0.11, CHCl$_3$)

$^1$H-NMR(CD$_3$OD): δ=0.78–1.05(m,27H,δ-Me(MeLeu), δ-Me(Lac)), 1.37(t,3H,Me(ethyl)), 1.38(d×2,3H,β-Me(Lac)), 1.46–1.90(m,12H,β-CH$_2$,γ-H(MeLeu)), 2.81–3.00(m, 12H,NMe), 3.01–3.20(m,4H,β-CH$_2$(PhLac,TYRA)), 4.00 (q,2H,CH$_2$(ethyl)), 4.76–5.81(m,8H,α-H), 6.85–7.33(m,9H, aromatic)

MS(FAB): (M+H)$^+$=993

EXAMPLE 24

Preparation of cyclo-(L-MeLeu-D-PhLac-L-MeLeu-D-Lac-L-MeLeu-D-TYRA(O-n-Pr)-L-MeLeu-D-Lac) (Code: PF 1022-018)

In 8 ml of THF, 217 mg of the PF 1022E substance were dissolved, followed by the addition of 0.2 ml of n-propyl iodide and 27 mg of 60% sodium hydride under ice cooling. The resulting mixture was stirred at 0° C. for 2 hours and then at room temperature for 4 hours. The reaction mixture was diluted with 50 ml of ethyl acetate, followed by washing with 30 ml of a saturated aqueous solution of sodium chloride, filtering through a small quantity of silica gel for chromatography and drying over anhydrous sodium sulfate. The solvent was then distilled off under reduced pressure. The residue so obtained was purified by chromatography on a silica gel column (chloroform:ethyl acetate=7:1→3:1), followed by lyophilization using 1,4-dioxane, whereby 107 mg of the title compound were obtained (yield: 47%).

$^1$H-NMR(CD$_3$OD): δ=0.78–1.11(m,30H,δ-Me(MeLeu), β-Me(Lac), OCH$_2$CH$_2$CH$_3$), 1.30–1.89(m,14H,β-CH$_2$,γ-H (MeLeu), OCH$_2$CH$_2$CH$_3$), 1.38, 1.39(d×2,J=7.0,3H,β-Me(Lac)), 2.82–3.00(m,12H,NMe), 2.92–3.21(m,4H,β-CH$_2$ (PhLac,TYRA), 3.90, 3.97(each t,2H,OCH$_2$CH$_2$CH$_3$), 4.75–5.83(m,8H,α-H), 6.85–7.33(m,9H,aromatic)

MS(FAB): (M+H)$^+$=1007

EXAMPLE 25

Preparation of cyclo-(L-MeLeu-D-PhLac-L-MeLeu-D-Lac-L-MeLeu-D-TYRA(O-iso-Pr)-L-MeLeu-D-Lac) (Code: PF 1022-019)

In 8 ml of THF, 206 mg of the PF 1022E substance were dissolved, followed by the addition of 0.2 ml of isopropyl iodide and 19 mg of 60% sodium hydride under ice cooling. The resulting mixture was stirred at 0° C. for 2 hours and then at room temperature for 4 hours. The reaction mixture was diluted with 50 ml of ethyl acetate, followed by washing successively with 12 ml of a saturated aqueous solution of sodium chloride and 28 ml of a 5% aqueous solution of sodium thiosulfate, filtering through a small quantity of silica gel for chromatography, and drying over anhydrous sodium sulfate. The solvent was distilled off under reduced pressure. The residue so obtained was purified by chromatography on a silica gel column (chloroform:ethyl acetate= 8:1→4:1), followed by lyophilization using 1,4-dioxane, whereby 108 mg of the title compound were obtained (yield: 50%).

$^1$H-NMR(CD$_3$OD): δ=0.78–1.06(m,27H,γ-Me(MeLeu), β-Me(Lac), 1.29, 1.30(d×2,6H,Me(isopropyl), 1.38, 1.39(d× 2,3H,β-Me(Lac)), 1.45–1.89(m,12H,β-CH$_2$,γ-H(MeLeu)), 2.82–3.00(m,12H,NMe), 2.91–3.21(m,4H,β-CH$_2$(PhLac, TYRA), 4.55(m,1H,CH(iso-propyl)), 4.74–5.82(m,8H,α-H), 6.84–7.34(m,9H,aromatic)

MS(FAB): (M+H)$^+$=1007

EXAMPLE 26

Preparation of cyclo-(L-MeLeu-D-PhLac-L-MeLeu-D-Lac-L-MeLeu-D-TYRA(O-All)-L-MeLeu-D-Lac) (Code: PF 1022-020)

In 8 ml of THF, 206 mg of the PF 1022E substance were dissolved, followed by the addition of 0.18 ml of allyl iodide and 20 mg of 60% sodium hydride under ice cooling. The resulting mixture was stirred at 0°C. for one hour. The reaction mixture was diluted with 50 ml of ethyl acetate, followed by washing with 30 ml of a saturated aqueous solution of sodium chloride, filtering through a small quantity of silica gel for chromatography, and drying over anhydrous sodium sulfate. The solvent was distilled off under reduced pressure. The residue so obtained was purified by chromatography on a silica gel column (chloroform:ethyl acetate=7:1→4:1), followed by crystallization from ether-hexane, whereby 158 mg of the title compound were obtained (yield: 73.8%).

$^1$H-NMR(CD$_3$OD): δ=0.78–1.07(m,27H,γ-Me(MeLeu), β-Me(Lac), Me(Lac), 1.30–1.90(m,12H,β-CH$_2$,γ-H (MeLeu)), 1.38, 1.39(d×2,3H,β-Me(Lac)), 2.81–3.00(m, 12H,NMe), 2.90–3.20(m,4H,β-CH$_2$(PhLac,TYRA), 4.52 (m,2H,allyl), 4.74–5.17, 5.44–5.82(m,8H,α-H), 5.20–5.25, 5.34–5.41, 6.05(each m,each 1H,allyl), 6.88–7.35(m,9H, aromatic)

MS(FAB): (M+H)$^+$=1005

EXAMPLE 27

Preparation of cyclo-(L-MeLeu-D-PhLac-L-MeLeu-D-Lac-L-MeLeu-D-TYRA(O-n-Bu)-L-MeLeu-D-Lac) (Code: PF 1022-021)

In 8 ml of THF, 204 mg of the PF 1022E substance were dissolved, followed by the addition of 0.24 ml of n-butyl iodide and 16 mg of 60% sodium hydride under ice cooling. The resulting mixture was stirred at 0° C. for one hour and then at room temperature for one hour. The reaction mixture was diluted with 50 ml of ethyl acetate, followed by washing with 30 ml of a saturated aqueous solution of sodium chloride, filtering through a small quantity of silica gel for chromatography, and then drying over anhydrous sodium sulfate. The solvent was then distilled off under reduced pressure. The residue so obtained was purified by chromatography on a silica gel column (chloroform:ethyl acetate= 8:1→4:1), followed by lyophilization using 1,4-dioxane, whereby 159 mg of the title compound were obtained (yield: 73.7%).

$^1$H-NMR(CD$_3$OD): δ=0.77–1.05(m,30H,δ-Me(MeLeu), β-Me(Lac), Me(butyl)), 1.28–1.90(m,16H,β-CH2,γ-H (MeLeu), OCH$_2$CH$_2$CH$_2$CH$_3$), 1.38, 1.39(d×2,3H,β-Me (Lac)), 2.82–3.00(m,12H,NMe), 2.92–3.20(m,4H,β-CH2PhLac,TYRA), 3.94(m,1H,OCH$_2$CH$_2$CH$_2$CH$_3$), 4.75–5.81(m,8H,α-H), 6.85–7.33(m,9H,aromatic)

MS(FAB): (M+H)$^+$=1021

EXAMPLE 28

Preparation of cyclo-(L-MeLeu-D-PhLac-L-MeLeu-D-Lac-L-MeLeu-D-TYRA(OBn)-L-MeLeu-D-Lac) (Code: PF 1022-022)

In 9 ml of THF, 305 mg of the PF 1022E substance were dissolved, followed by the addition of 0.07 ml of benzyl iodide and 28 mg of 60% sodium hydride under ice cooling. The resulting mixture was stirred at 0° C. for 1.5 hours. The reaction mixture was diluted with 50 ml of ethyl acetate, followed by washing with 40 ml of a saturated aqueous solution of sodium chloride, filtering through a small quantity of silica gel for chromatography, and drying over anhydrous sodium sulfate. The solvent was then distilled off under reduced pressure. The residue so obtained was purified by chromatography on a silica gel column (chloroform:ethyl acetate=10:1), followed by lyophilization using a liquid mixture of 1,4-dioxane and water, whereby 320 mg of the title compound were obtained (yield: 95.8%).

$^1$H-NMR(CD$_3$OD): δ=0.78–1.06(m,27H,δ-Me(MeLeu), β-Me(Lac)), 1.25–1.90(m,12H,β-CH$_2$,γ-H(MeLeu)), 1.38, 1.39(d×2,3H,β-Me(Lac)), 2.82–3.00(m,12H,NMe), 2.86–3.20(m,4H,β-CH$_2$(PhLac,TYRA)), 4.74–4.78, 5.17–5.82(m,8H,α-H), 5.05(s,2H,CH$_2$Ph), 6.95–7.50(m, 14H,aromatic)

MS(FAB): (M+H)$^+$=1055

EXAMPLE 29

Preparation of cyclo-(L-MeLeu-D-PhLac-L-MeLeu-D-Lac-L-MeLeu-D-TYRA(3,5-di-Cl)-L-MeLeu-D-Lac) (Code: PF 1022-023)

In 15 ml of methylene chloride, 301 mg of the PF 1022E substance were dissolved, followed by the addition of 0.22 ml of t-butyl hypochlorite under ice cooling. The resulting mixture was stirred at the same temperature for 40 minutes. The reaction mixture was added with 30 ml of a 5% aqueous solution of sodium thiosulfate and 30 ml of methylene chloride. The resulting mixture was allowed to separate into two layers. The organic layer so obtained was filtered through a small quantity of silica gel for chromatography, followed by drying over anhydrous sodium sulfate. The solvent was then distilled off under reduced pressure. The residue so obtained was purified by chromatography on a silica gel column (chloroform:ethyl acetate=8:1→4:1), whereby 120 mg of the title compound were obtained (yield: 37.2%).

$^1$H-NMR(CD$_3$OD): δ=0.78–1.07(m,27H,δ-Me(MeLeu), β-Me(Lac)), 1.26–1.90(m,12H,β-CH$_2$,γ-H(MeLeu)), 1.40, 1.41(d×2,3H,β-Me(Lac)), 2.80–3.18(m,12H,NMe), 2.80–3.20(m,4H,β-CH$_2$(PhLac,TYRA)), 4.78–5.85(m,8H, α-H), 7.24–7.35(m,7H,aroma-tic)

MS(FAB): (M+H)$^+$=1033, 1035

EXAMPLE 30

Preparation of cyclo-(L-MeLeu-D-PhLac-L-MeLeu-D-Lac-L-MeLeu-D-TYRA(3,5-di-Br)-L-MeLeu-D-Lac) (Code: PF 1022-025)

In 20 ml of methylene chloride, 406 mg of the PF 1022E substance were dissolved. The resulting solution was added with 0.12 ml of triethylamine and 0.07 ml of bromine under ice cooling, followed by stirring at 0° C. for 20 minutes. The reaction mixture was added with 40 me of chloroform and 30 ml of a 5% aqueous solution of sodium thiosulfate. The resulting mixture was allowed to separate into two layers. The water layer so obtained was extracted with a liquid mixture of 20 ml of ethyl acetate and 10 ml of hexane. The combined organic layers were filtered through a small quantity of silica gel for chromatography, followed by drying over anhydrous sodium sulfate. The solvent was then distilled off under reduced pressure. The residue so obtained was purified by chromatography on a silica gel column (chloroform:ethyl acetate=9:1→7:1), whereby 420 mg of the title compound were obtained (yield: 89.0%).

[α]: −90° (c=0.2, MeOH)

$^1$H-NMR(CD$_3$OD): δ=0.78–1.07(m,27H,δ-Me(MeLeu), β-Me(Lac)), 1.38(d,J=6.7,β-Me(Lac)), 1.28–1.91(m,12H,β-CH$_2$,γ-H(Me- Leu)), 2.82–3.01(m,12H,NMe), 2.92–3.21(m, 4H,β-CH$_2$(PhLac,TYRA), 4.77–5.82(m,8H,α-H), 7.26–7.46(m,7H,aromatic)

MS(FAB):(M+H)$^+$=1121, 1123, 1125

EXAMPLE 31

Preparation of cyclo-(L-MeLeu-D-PhLac-L-MeLeu-D-Lac-L-MeLeu-D-TYRA(3,5-di-Br,O-Me)-L-MeLeu-D-Lac) (Code: PF 1022-026)

In 8 ml of THF, 200 mg of the 3,5-dibromide of the PF 1022E substance were dissolved. The resulting solution was added with 0.1 ml of methyl iodide and 16 mg of 60% sodium hydride under ice cooling, followed by stirring at 0° C. for 1.5 hours. The reaction mixture was diluted with 50 ml of ethyl acetate, followed by washing with 30 ml of a saturated aqueous solution of sodium chloride, filtering through a small quantity of silica gel for chromatography, and drying over anhydrous sodium sulfate. The solvents were then distilled off under reduced pressure. The residue so obtained was purified by chromatography on a silica gel column (chloroform:ethyl acetate=10:1), whereby 108 mg of the title compound were obtained (yield: 53.1%).

¹H-NMR(CD₃OD): δ=0.78–1.08(m,27H,δ-Me(MeLeu), β-Me(Lac)), 1.28–1.90(m,12H,δ-Me(MeLeu),β-Me(Lac)), 1.28–1.90(m,12H,β-CH₂,γ-H(MeLeu)), 1.38, 1.39(d×2,J= 6.7,β-Me(Lac)), 2.81–3.13(m,12H,NMe), 2.90–3.20(m,4H, β-CH₂(PhLac,TYRA)), 4.77–5.82(m,8H,α-H), 7.24–7.59 (m,7H,aromatic)

MS(FAB):(M+H)⁺=1135, 1137, 1139

EXAMPLE 32

Preparation of cyclo-(L-MeLeu-D-PhLac-L-MeLeu-D-Lac-L-MeLeu-D-TYRA(O-Oct)-L-MeLeu-D-Lac) (Code: PF 1022-029)

In 5 ml of THF, 253 mg of the PF 1022E substance were dissolved. The resulting solution was added with 2.4 ml of octyl iodide and 23 mg of 60% sodium hydride under ice cooling, followed by stirring at 0° C. for one hour. The reaction mixture was diluted with 40 ml of ethyl acetate and 10 ml of hexane, followed by washing with 30 ml of a saturated aqueous solution of sodium chloride, filtering through a small quantity of silica gel for chromatography and drying over anhydrous sodium sulfate. The solvents were then distilled off under reduced pressure. The residue so obtained was purified by chromatography on a silica gel column (chloroform:ethyl acetate=20:1→10:1→5:1), whereby 199 mg of the title compound were obtained (yield: 70.6%).

EXAMPLE 33

Preparation of cyclo-(L-MeLeu-D-PhLac-L-MeLeu-D-Lac-L-MeLeu-D-TYRA(O-THP)-L-MeLeu-D-Lac) (Code: PF 1022-224)

In 5 ml of methylene chloride, 202 mg of the PF 1022E substance were dissolved. The resulting solution was added with 4.5 mg of p-toluenesulfonic acid hydrate and 0.04 ml of 2,3-dihydropyran, followed by stirring at room temperature for 40 minutes. The reaction mixture was added with 0.01 ml of triethylamine, followed by concentration. The residue so obtained was purified by chromatography on a silica gel column (ethyl acetate:hexane=1:1), whereby 200 mg of the title compound were obtained (yield: 91%).

¹H-NMR(CDCl3): δ=0.79–1.05(m,27H,δ-Me(MeLeu),β-Me(Lac)), 1.23–2.05(m,18H,β-CH₂,γ-H(MeLeu), OCH₂ (CH₂)₃(THP)), 1.40(d,J=6.7,β-Me(Lac)), 2.72–3.01(s×10, 12H,NMe), 3.02–3.18(m,4H,β-CH₂(PhLac,TYRA), 3.57–3.62, 3.85–3.91(m,each 1H,OCH₂CH₂(THP)), 4.47–5.70(m,9H,α-H,OCHO(THP)), 6.94–6.99, 7.11–7.15, 7.21–7.31(m,9H,aromatic)

MS(FAB):(M+H)⁺=1049

EXAMPLE 34

Preparation of cyclo-(L-MeLeu-D-PhLac-L-MeLeu-D-Lac-L-MeLeu-D-TYRA(O-Tr)-L-MeLeu-D-Lac) (Code: PF 1022-223)

In 16 ml of methylene chloride, 410 mg of the PF 1022E substance were dissolved. The resulting solu- tion was added with 210 mg of trityl chloride, 0.08 ml of triethylamine and 16 mg of 4-dimethylaminopyridine, followed by stirring at room temperature for 24 hours. The reaction mixture was diluted with 8 ml of toluene, followed by purification by chromatography on a silica gel column (ethyl acetate:hexane=2:1), whereby 287 mg of the title compound were obtained as white powder (yield: 56%).

m.p. 109°–115° C. (dec.)

¹H-NMR(CD₃OD): δ=0.78–1.05(m,27H,δ-Me(MeLeu), β-Me(Lac)), 1.24–1.80(m,12H,β-CH₂,γ-H(MeLeu)), 1.40 (d,3H,J=7,β-Me(Lac)), 2.51–3.01(s×10,12H,NMe), 2.77–3.18(m,4H,β-CH₂(PhLac,TYRA)), 4.41–5.70(m,8H, α-H), 6.57–6.62, 6.81–6.84, 7.18–7.31, 7.41–7.45(m,24H, aromatic)

MS(FAB):(M+H)⁺=1207

INDUSTRIAL FIELD OF UTILIZATION OF INVENTION

The PF 1022 derivatives represented by the general formula (I) which are provided herein by the present invention each has anthelmintic activities against various parasitic worms which are parasitic on human bodies, domestic animals and companion animals. They are therefore useful as anthelmintic agent for prevention or treatment of parasitic infections.

We claim:

1. A cyclodepsipeptide represented by the following general formula:

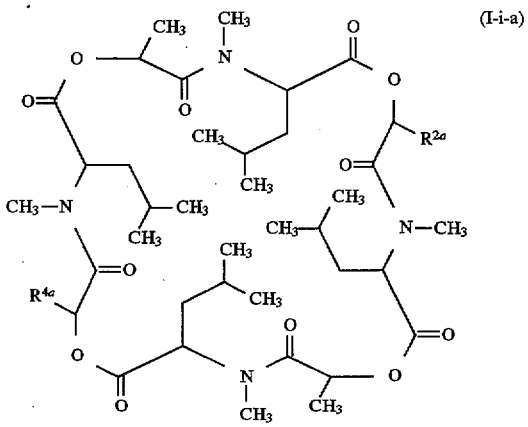

wherein R²ᵃ and R⁴ᵃ are each a cyclohexylmethyl group or benzyl group, provided that at least one of R²ᵃ and R⁴ᵃ is a cyclohexylmethyl group.

2. A cyclodepsipeptide represented by the following general formula:

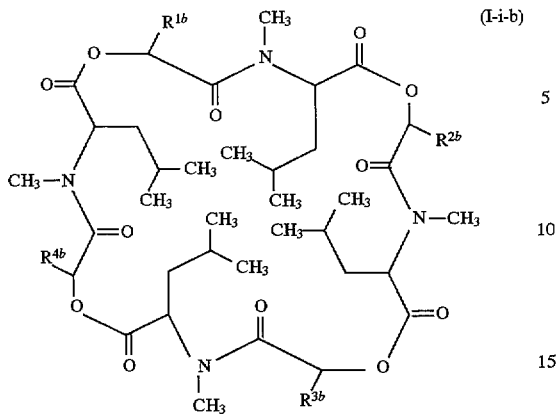

wherein $R^{1b}$, $R^{2b}$, $R^{3b}$ and $R^{4b}$ are each a cyclohexylmethyl group or benzyl group, provided that at least one of $R^{1b}$, $R^{2b}$, $R^{3b}$ and $R^{4b}$ is a cyclohexylmethyl group.

3. A cyclodepsipeptide represented by the following general formula:

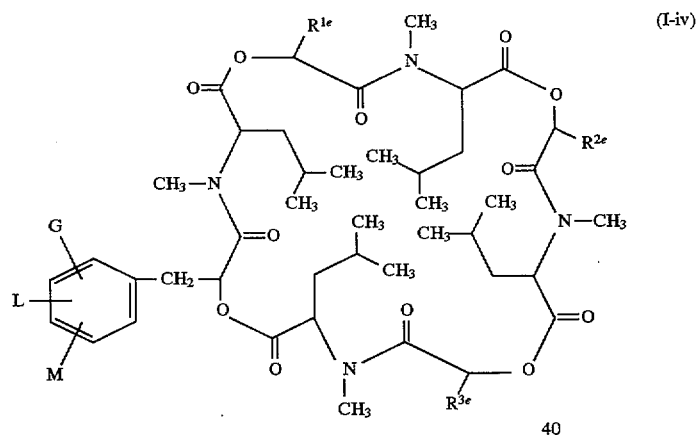

wherein $R^{1e}$, $R^{2e}$ and $R^{3e}$ are each a linear or branched alkyl group containing 1 to 11 carbon atoms, and may be the same or different from each other, and G, L and M denote independently a hydrogen, a halo group, hydroxyl group, an alkoxy group, a lower alkenyloxy group, a phenyl-lower alkoxy group, an alkylcarbonyloxy group, tetrahydropyranyloxy group or trityloxy group.

4. A cyclodepsipeptide represented by the following general formula:

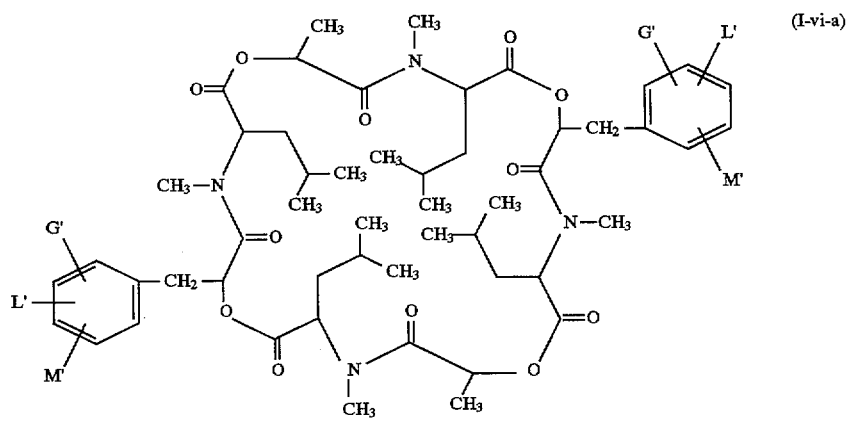

wherein G', L' and M' denote independently a substituent chosen from a halo group, hydroxyl group, alkoxy group, lower alkenyloxy group, phenyl-lower alkoxy group, alkylcarbonyloxy group, tetrahydropyranyloxy group or trityloxy group.

5. A cyclodepsipeptide represented by the following general formula:

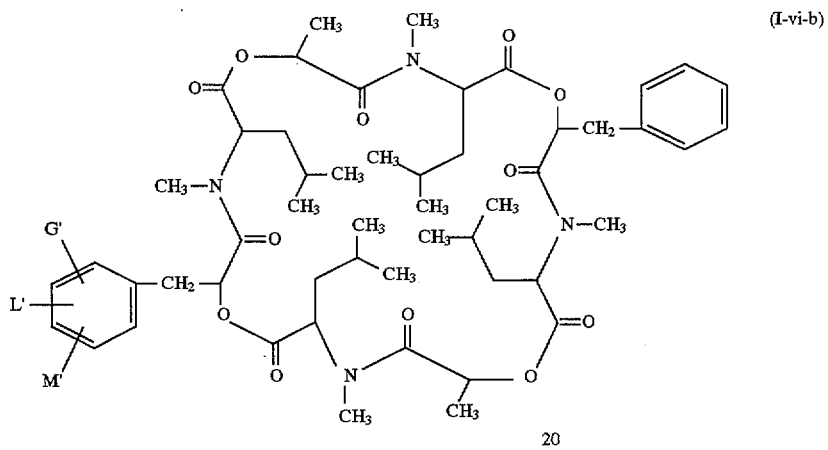

wherein G', L' and M' denote independently a substituent chosen from a halo group, hydroxyl group, alkoxy group, lower alkenyloxy group, phenyl-lower alkyl group, alkylcarbonyloxy group, tetrahydropyranyloxy group or trityloxy group.

6. A cyclodepsipeptide, PF 1022E substance represented by the following formula:

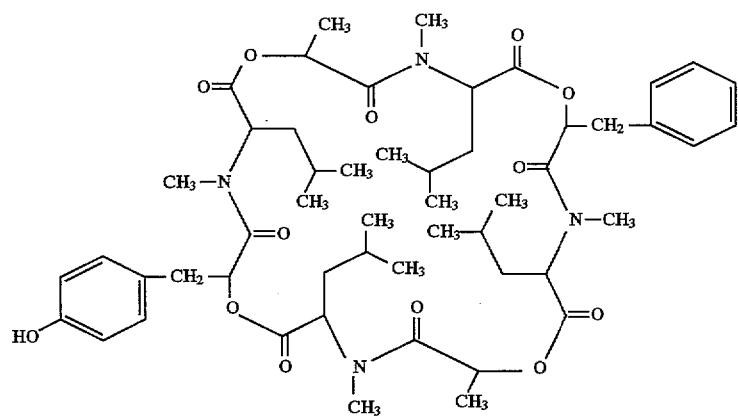

7. An anthelmintic composition, characterized in that the composition comprises, as the active ingredient, a cyclodepsipeptide which is the hydrogenated derivative of the PF 1022 substance represented by the formula (I-i-a) as defined in claim 1.

8. An anthelmintic composition, characterized in that the composition comprises, as the active ingredient, a cyclodepsipeptide which is the hydrogenated derivative of the PF 1022 B substance represented by the formula (I-i-b) as defined in claim 2.

9. An anthelmintic composition, characterized in that the composition comprises, as the active ingredient, a cyclodepsipeptide represented by the formula (I-iv) as defined in claim 3.

10. An anthelmintic composition, characterized in that the composition comprises, as the active ingredient, a cyclodepsipeptide represented by the formula (I-vi-a) as defined in claim 4.

11. An anthelmintic composition, characterized in that the composition comprises, as the active ingredient, a cyclodepsipeptide represented by the formula (I-vi-b) as defined in claim 5.

12. An anthelmintic composition, characterized in that the composition comprises, as the active ingredient, a cyclodepsipeptide which is the hydrogenated derivative of the PF 1022E substance as defined in claim 6.

* * * * *